US012390462B2

(12) United States Patent
Xiong et al.

(10) Patent No.: US 12,390,462 B2
(45) Date of Patent: Aug. 19, 2025

(54) MUSCARINIC ACETYLCHOLINE M1 RECEPTOR ANTAGONISTS

(71) Applicant: Contineum Therapeutics, Inc., San Diego, CA (US)

(72) Inventors: Yifeng Xiong, San Diego, CA (US); Jeffrey Roppe, Temecula, CA (US); Austin Chih-Yu Chen, San Diego, CA (US); Yalda Bravo, San Diego, CA (US); Thomas Schrader, San Diego, CA (US); Jill Melissa Baccei, San Diego, CA (US)

(73) Assignee: Contineum Therapeutics, Inc., San Diego, CA (US)

( * ) Notice: Subject to any disclaimer, the term of this patent is extended or adjusted under 35 U.S.C. 154(b) by 67 days.

(21) Appl. No.: 18/225,992

(22) Filed: Jul. 25, 2023

(65) Prior Publication Data

US 2023/0364082 A1    Nov. 16, 2023

Related U.S. Application Data

(62) Division of application No. 17/103,455, filed on Nov. 24, 2020, now Pat. No. 11,752,149.

(60) Provisional application No. 62/942,665, filed on Dec. 2, 2019.

(51) Int. Cl.
*A61K 31/4995*  (2006.01)
*A61K 31/501*   (2006.01)
*A61K 45/06*    (2006.01)
*C07D 487/08*   (2006.01)

(52) U.S. Cl.
CPC ........ *A61K 31/4995* (2013.01); *A61K 31/501* (2013.01); *A61K 45/06* (2013.01); *C07D 487/08* (2013.01)

(58) Field of Classification Search
CPC ................................................. A61K 31/4995
See application file for complete search history.

(56) References Cited

U.S. PATENT DOCUMENTS

| | | | |
|---|---|---|---|
| 4,803,203 A | 2/1989 | Caprathe et al. |
| 4,873,331 A | 10/1989 | Childers, Jr. et al. |
| 5,089,497 A | 2/1992 | Jaen et al. |
| 5,846,514 A | 12/1998 | Foster |
| 6,334,997 B1 | 1/2002 | Foster |
| 7,071,335 B2 | 7/2006 | Kyle et al. |
| 8,648,074 B2 | 2/2014 | Li et al. |
| 8,906,924 B2 | 12/2014 | Baroni et al. |
| 8,999,974 B2 | 4/2015 | Morita et al. |
| 9,446,030 B2 | 9/2016 | Dooley |
| 9,592,288 B2 | 3/2017 | Schultz |
| 9,616,052 B2 | 4/2017 | Dooley |
| 10,464,919 B2 | 11/2019 | Lee |
| 10,550,105 B2 | 2/2020 | Vasbinder et al. |
| 10,596,378 B2 | 3/2020 | Rustick |
| 11,512,090 B2 | 11/2022 | Xiong et al. |
| 11,752,149 B2 | 9/2023 | Xiong et al. |
| 12,054,487 B2 | 8/2024 | Schrader |
| 12,180,243 B2 | 12/2024 | Zhao et al. |
| 2006/0233843 A1 | 10/2006 | Conn et al. |
| 2007/0129378 A1 | 6/2007 | Siddiqui et al. |
| 2013/0178458 A1 | 7/2013 | Lindsley et al. |
| 2013/0289019 A1 | 10/2013 | Chau |
| 2018/0258085 A1 | 9/2018 | Brown et al. |
| 2020/0181166 A1 | 6/2020 | Lindsley |
| 2020/0231592 A1 | 7/2020 | Lindsley et al. |
| 2021/0061779 A1 | 3/2021 | Wipf |
| 2021/0113532 A1 | 4/2021 | Sidrauski |
| 2021/0137910 A1 | 5/2021 | Jones |
| 2021/0155629 A1 | 5/2021 | Schrader et al. |
| 2021/0161889 A1 | 6/2021 | Xiong et al. |
| 2021/0186963 A1 | 6/2021 | Wipf |
| 2022/0332721 A1 | 10/2022 | Xiong |
| 2023/0089921 A1 | 3/2023 | Baccei et al. |
| 2023/0364082 A1 | 11/2023 | Xiong |
| 2024/0217981 A1 | 7/2024 | Roppe |
| 2025/0026758 A1 | 1/2025 | Schrader et al. |

FOREIGN PATENT DOCUMENTS

| | | |
|---|---|---|
| CN | 107663159 A | 2/2018 |
| CN | 108349936 A | 7/2018 |
| EP | 2675893 | 12/2013 |
| EP | 3171867 | 5/2017 |
| JP | 2008507575 A | 3/2008 |
| JP | 2009520689 A | 5/2009 |
| JP | 2021523104 A | 9/2021 |
| JP | 2021536505 A | 12/2021 |
| WO | WO-97/23482 A1 | 7/1997 |
| WO | 200200651 A2 | 1/2002 |

(Continued)

OTHER PUBLICATIONS

International Search Report mailed on Jul. 15, 2022, for PCT Application No. PCT/US2022/024684, filed on Apr. 13, 2022, 2 pages.
Jicha. G. et al. (Feb. 2019). "Hippocampal Sclerosis, Argyrophilic Grain Disease, and Primary Age-Related Tauopathy," Continuum 25(1):208-233.
Klein J. (Apr. 29, 2020). "Can a person prevent multiple sclerosis?" *Medical News Today* 9 pages.
Liu, X. et al. (2019). "Parkinsonism Caused by Viral Encephalitis Affecting the Bilateral Substantia Nigra," *Clin Neuroradiol* 29(3):571-573.
Smith, S. et al. (Aug. 3, 2022). "Prevention and Management Strategies for Diabetic Neuropathy" *Life(Basel)* 12(8):1185.
Teylan, M. et al. (Jul. 2019). "Clinical diagnoses among individuals with primary age-related tauopathy versus Alzheimer's neuropathology," *Lab Invest* 99:1049-1055.

(Continued)

*Primary Examiner* — Yong S. Chong
(74) *Attorney, Agent, or Firm* — Morrison & Foerster LLP

(57) ABSTRACT

Provided herein are compounds which are useful as antagonists of the muscarinic acetylcholine receptor $M_1$ (mAChR $M_1$); synthetic methods for making the compounds; pharmaceutical compositions comprising the compounds; and methods of treating neurological and psychiatric disorders associated with muscarinic acetylcholine receptor dysfunction using the compounds and compositions.

6 Claims, No Drawings

(56) References Cited

FOREIGN PATENT DOCUMENTS

| | | |
|---|---|---|
| WO | WO-2006/010751 A1 | 2/2006 |
| WO | 2007064732 A1 | 6/2007 |
| WO | WO-2007/077508 A2 | 7/2007 |
| WO | WO-2007/077508 A3 | 7/2007 |
| WO | 2009117421 A2 | 9/2009 |
| WO | 2011080445 A1 | 7/2011 |
| WO | 2012020567 A1 | 2/2012 |
| WO | 2012112933 A1 | 8/2012 |
| WO | WO-2013/103931 A1 | 7/2013 |
| WO | 2016014117 A1 | 1/2016 |
| WO | 2016084866 A1 | 6/2016 |
| WO | 2016107602 A1 | 7/2016 |
| WO | 2017066705 A1 | 4/2017 |
| WO | 2017079641 A1 | 5/2017 |
| WO | 2017165822 A1 | 9/2017 |
| WO | 2017223474 A1 | 12/2017 |
| WO | WO-2018/089433 A1 | 5/2018 |
| WO | 2018160891 A1 | 9/2018 |
| WO | 2019073251 A1 | 4/2019 |
| WO | 2019126559 A1 | 6/2019 |
| WO | WO-2019/158572 A1 | 8/2019 |
| WO | 2019173790 A1 | 9/2019 |
| WO | 2019179515 A1 | 9/2019 |
| WO | WO-2019/212937 A1 | 11/2019 |
| WO | WO-2019/241131 A1 | 12/2019 |
| WO | 2020021021 A1 | 1/2020 |
| WO | WO-2020/051153 A1 | 3/2020 |
| WO | 2020123675 A1 | 6/2020 |
| WO | 2020231806 A1 | 11/2020 |
| WO | 2020231808 A1 | 11/2020 |
| WO | 2020257180 A1 | 12/2020 |
| WO | 2021071806 A1 | 4/2021 |
| WO | 2021071837 A1 | 4/2021 |
| WO | WO-2021/071843 A1 | 4/2021 |
| WO | 2021094210 A1 | 5/2021 |
| WO | 2022221450 A1 | 10/2022 |
| WO | 2024088408 A1 | 5/2024 |
| WO | 2024094170 A1 | 5/2024 |
| WO | 2024169895 A1 | 8/2024 |
| WO | 2024217531 A1 | 10/2024 |

OTHER PUBLICATIONS

Written Opinion mailed on Jul. 15, 2022, for PCT Application No. PCT/US2022/024684, filed on Apr. 13, 2022, 3 pages.
Zuev, D. et al. (2005). "Stereoselective synthesis of new conformationally restricted analogues of a potent CGRP receptor antagonist," Organic Letters 7(12):2465-2468.
Bender, A.M. et al. (Aug. 1, 2017, e-published May 15, 2017). "Discovery and optimization of 3-(4-aryl/heteroarylsulfonyl)piperazin-1-yl)-6-(piperidin-1-yl)pyridazines as novel, CNS penetrant pan-muscarinic antagonists," Bioorg Med Chem Lett 27(15):3576-3581.
Extended European Search Report mailed on May 6, 2022, for EP Patent Application No. 19857624.1, 8 pages.
Extended European Search Report mailed on Oct. 10, 2023, for EP Patent Application No. 20875038.0, 7 pages.
International Search Report mailed Oct. 18, 2019, for PCT Application No. PCT/US2019/036345, filed Jun. 10, 2019, 4 pages.
International Search Report mailed on Nov. 21, 2019, for PCT Application No. PCT/US2019/049374, filed Sep. 3, 2019, 3 pages.
International Search Report mailed on Dec. 29, 2020 for PCT Application No. PCT/US2020/054412, filed Oct. 6, 2020, 3 pages.
Manetti, D. et al. (May 18, 2000). "Design, synthesis, and preliminary pharmacological evaluation of 1, 4-diazabicyclo[4.3.0]nonan-9-ones as a new class of highly potent nootropic agents," Journal of Medicinal Chemistry 43(10):1969-1974.
Melancon, B.J. et al. (Jan. 15, 2012, e-published Dec. 6, 2011). "Development of a more highly selective M1 antagonist from the continued optimization of the MLPCN Probe ML012," Bioorg Med Chem Lett 22(2):1044-1048.

Melancon, B.J. et al. (Aug. 1, 2012, e-published Jun. 15, 2012). "Development of novel M1 antagonist scaffolds through the continued optimization of the MLPCN probe ML012," Bioorg Med Chem Lett 22(15):5035-5040.
PubChem CID 70746046, (Create Date Mar. 4, 2013), located at <https://pubchem.ncbi.nlm.nih.gov/compound/70746046>, 5 pages.
PubChem CID 101131894, (Create Date Dec. 17, 2015), located at <https://pubchem.ncbi.nlm.nih.gov/compound/101131894>, 7 pages.
PubChem CID 101131895, (Create Date Dec. 17, 2015), located at <https://pubchem.ncbi.nlm.nih.gov/compound/101131895>, 8 pages.
PubChem CID 102350371, (Create Date Dec. 25, 2015), located at <https://pubchem.ncbi.nlm.nih.gov/compound/102350371>, 7 pages.
Sheffler, D.J. et al. (Aug. 2009, e-published Apr. 30, 2009). "A novel selective muscarinic acetylcholine receptor subtype 1 antagonist reduces seizures without impairing hippocampus-dependent learning," Mol Pharmacol 76(2):356-368.
Weaver, C. D. et al. (2009). "Discovery and development of a potent and highly selective small molecule muscarinic acetylcholine receptor subtype I (mAChR 1 or M1) antagonist in vitro and in vivo probe," Current Topics in Medicinal Chemistry 9(13):1217-1226.
Written Opinion mailed Oct. 18, 2019, for PCT Application No. PCT/US2019/036345, filed Jun. 10, 2019, 6 pages.
Written Opinion mailed on Nov. 21, 2019, for PCT Application No. PCT/US2019/049374, filed Sep. 3, 2019, 4 pages.
Written Opinion mailed on Dec. 29, 2020 for PCT Application No. PCT/US2020/054412, filed Oct. 6, 2020, 3 pages.
Ablordeppey, S. Y. et al. (Aug. 1, 2008). "Identification of A Butyrophenone Analog as a Potential Atypical Antipsychotic Agent: 4-[4-(4-Chlorophenyl)-1,4-diazepan-1-yl]-1-(4-fluorophenyl)butan-1-one," Bioorg Med Chem. 16(15):7291-7301.
Berge, S. M. et al. (Jan. 1977). "Pharmaceutical Salts," Journal of Pharmaceutical Sciences 66(1):19 pages.
Busch-Petersen, J. et al. (2011, e-pub. Sep. 23, 2011). "Inhaled Long-Acting Muscarinic Antagonists in Chronic Obstructive Pulmonary Disease," Future Medical Chemistry 3(13):1623-1634.
CAS Registry No. 2249464-92-2, entered STN Nov. 18, 2018, 1 page.
Cheng, H. et al. (Nov. 25, 2006). "Expression of mACh Receptor m1-m5 Subunits in the Vestibular Endorgans of Rat," Journal of Clinical Otorhinolaryngology 20(22): 1027-1029. (English Translation of Abstract only).
Dean, D.C. (Jul. 2000). "Recent Advances in the Synthesis and Applications of Radiolabeled Compounds for Drug Discovery and Development," Current Pharm. Des. 6(10):113, TOC Only, 2 pages.
Evans, A.E. (Mar. 1981, e-pub. Jan. 9, 2007). "Synthesis of Radiolabelled Compounds," J Radio Anal. Chem. 64(1-2):9-32.
FDA Center for Drug Evaluation and Research. (2009). "Application No. 22-527," Pharmacology Review (s), 252 pages.
Fleisher, D. et al. (May 22, 1996). "Improved Oral Drug Delivery: Solubility Limitations Overcome by the Use of Prodrugs," Advanced Drug Delivery Reviews 19(2):115-130.
Frothingham, S. et al. (Nov. 10, 2022). "The Possibility of Multiple Sclerosis Prevention," Healthline, located at https://www.healthline.com/health/multiple-sclerosis-prevention, last visited on Jan. 6, 2025, 18 pages.
Kabalka, G.W. et al. (1989). "The Synthesis of Radiolabeled Compounds via Organometallic Intermediates," Tetrahedron 45(21):6601-6621.
Lochner, M. et al. (Sep. 2016, e-pub. Apr. 20, 2016). "The Muscarinic Antagonists Scopolamine and Atropine are Competitive Antagonists at 5-HT3 Receptors," Neuropharmacology 108:220-228.
Schrader, T. O. et al. (Dec. 24, 2020, e-pub. Jan. 14, 2021). "Discovery of PIPE-359, a Brain-Penetrant, Selective M1 Receptor Antagonist with Robust Efficacy in Murine MOG-EAE," ACS Med Chem Lett 12(1):155-161.
U.S. Appl. No. 16/827,546, filed Mar. 23, 2020, for Rustick et al. (Copy not submitted herewith pursuant to the waiver of 37 C.F.R. 1.98(a)(2)(iii) issued by the Office on Sep. 21, 2004).
U.S. Appl. No. 18/747,272, filed Jun. 18, 2024, for Schrader et al. (Copy not submitted herewith pursuant to the waiver of 37 C.F.R. 1.98(a)(2)(iii) issued by the Office on Sep. 21, 2004).

(56) References Cited

OTHER PUBLICATIONS

U.S. Appl. No. 19/030,481, filed Jan. 17, 2025, for Baccei et al. (Copy not submitted herewith pursuant to the waiver of 37 C.F.R. 1.98(a)(2)(iii) issued by the Office on Sep. 21, 2004).
Zhao, M. et al. (Jul. 23, 1998). "A Novel Chromium Trioxide Catalyzed Oxidation of Primary Alcohols to the Carboxylic Acids," Tetrahedron Letters 39(30):5323-5326.
Zipp, G. G. et al. (Aug. 15, 2014, e-pub. Jul. 1, 2014). "Novel Inhibitors of the High-Affinity L-Proline Transporter as Potential Therapeutic Agents for the Treatment of Cognitive Disorders," Bioorg Med Chem Lett. 24(16):3886-3890.

MUSCARINIC ACETYLCHOLINE M1 RECEPTOR ANTAGONISTS

CROSS REFERENCE TO RELATED APPLICATIONS

This application is a divisional of U.S. application Ser. No. 17/103,455 filed Nov. 24, 2020, which claims priority to U.S. Provisional Application No. 62/942,665, filed Dec. 2, 2019, which are hereby incorporated by reference in their entirety and for all purposes.

BACKGROUND

The human muscarinic acetylcholine receptor $M_1$ (mAChR $M_1$) is a protein of 479 amino acids encoded by the CHRM1 gene. The mAChR $M_1$ is one of five members of the family of muscarinic acetylcholine receptors ($M_1$-$M_5$), which are widely expressed throughout the body where they have varying roles in cognitive, sensory, motor, and autonomic functions. The $M_1$ mAChR is found in both the central and peripheral nervous systems, particularly in the cerebral cortex and sympathetic ganglia. Based on the potential role of mAChR $M_1$ in seizure activity and motor control, highly selective mAChR $M_1$ antagonists may have potential utility in the treatment of some epileptic disorders, as well as certain movement disorders, including Parkinson's disease, dystonia, and fragile X syndrome.

BRIEF SUMMARY

This disclosure provides, for example, compounds and compositions which are antagonists of the muscarinic acetylcholine $M_1$ receptor (mAChR $M_1$), and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of muscarinic acetylcholine M1 receptor activity in patients.

In one aspect is provided a compound of Formula (IA) or (IB):

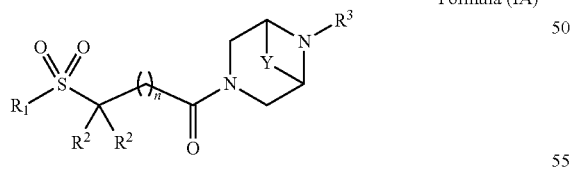

Formula (IA)

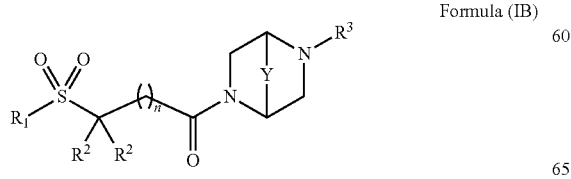

Formula (IB)

wherein:

Y is —$CH_2$—, —$CH_2CH_2$—, or —$CH_2OCH_2$—;

$R^1$ is

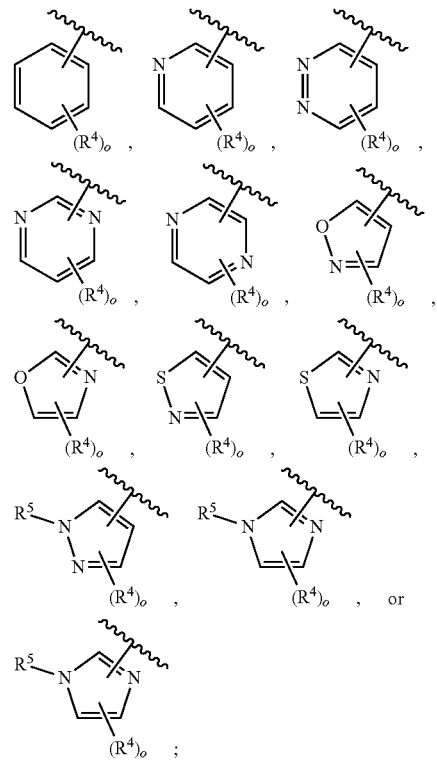

each $R^2$ is independently selected from hydrogen, deuterium, or $C_{1-6}$ alkyl;

$R^3$ is

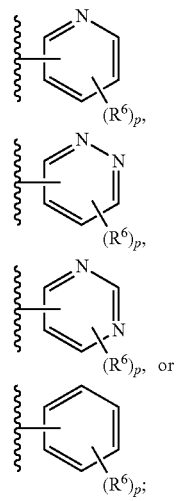

each $R^4$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^5$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each $R^6$ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3;

or a pharmaceutically acceptable salt or solvate thereof, provided that the aforementioned combinations do not violate the rules of valency known to those skilled in the art.

In one aspect is provided a compound of Formula (IIA) or (IIB):

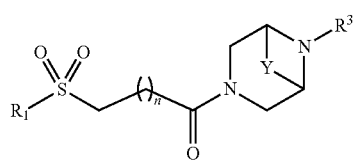

Formula (IIA)

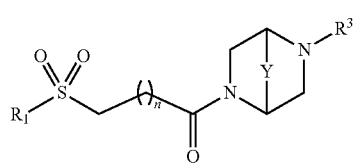

Formula (IIB)

wherein:

Y is —CH$_2$—, —CH$_2$CH$_2$—, or —CH$_2$OCH$_2$—;

$R^1$ is

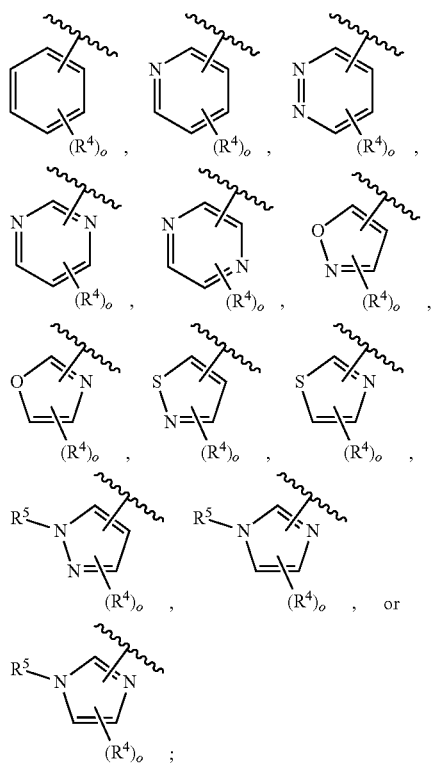

$R^3$ is

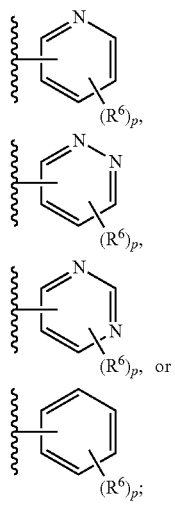

each $R^4$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^5$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each $R^6$ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3;

or a pharmaceutically acceptable salt or solvate thereof, provided that the aforementioned combinations do not violate the rules of valency known to those skilled in the art.

In another aspect is provided a compound of Formula (III):

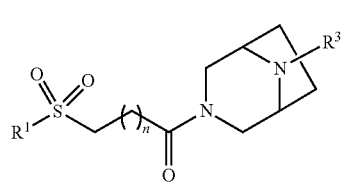

Formula (III)

wherein:

$R^1$ is

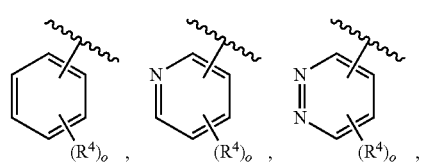

-continued

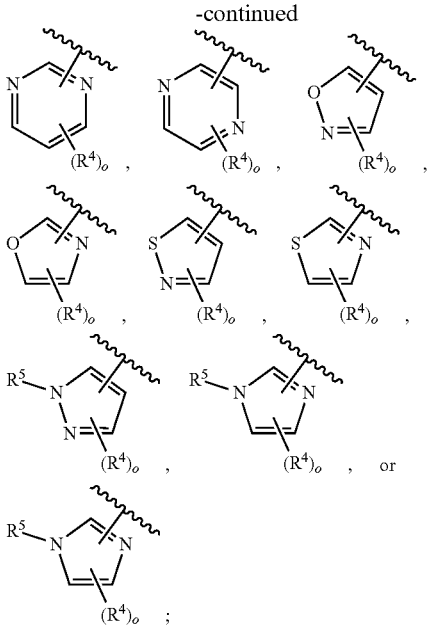

$R^3$ is

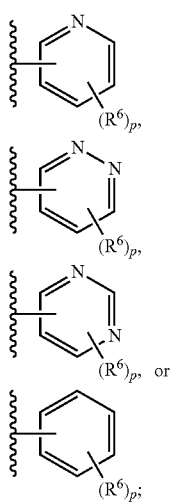

each $R^4$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^5$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each $R^6$ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3;

or a pharmaceutically acceptable salt or solvate thereof, provided that the aforementioned combinations do not violate the rules of valency known to those skilled in the art.

In some embodiments of a compound of Formula (IA), (IB), (IIA), (IIB), or (III), or a pharmaceutically acceptable salt or solvate thereof, $R^1$ is

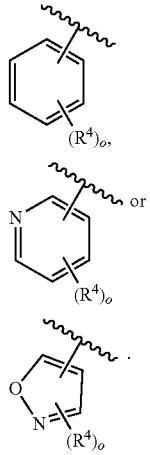

In some embodiments of a compound of Formula (IA), (IB), (IIA), (IIB), or (III), or a pharmaceutically acceptable salt or solvate thereof, $R^3$ is

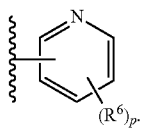

In some embodiments of a compound of Formula (IA), (IB), (IIA), (IIB), or (III), or a pharmaceutically acceptable salt or solvate thereof, $R^3$ is

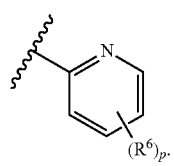

In some embodiments of a compound of Formula (IA), (IB), (IIA), (IIB), or (III), or a pharmaceutically acceptable salt or solvate thereof, $R^3$ is

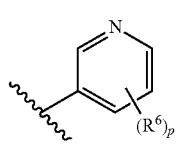

In some embodiments of a compound of Formula (IA), (IB), (IIA), (IIB), or (III), or a pharmaceutically acceptable salt or solvate thereof, $R^3$ is

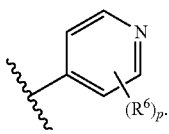

In some embodiments of a compound of Formula (IA), (IB), (IIA), (IIB), or (III), or a pharmaceutically acceptable salt or solvate thereof, $R^3$ is

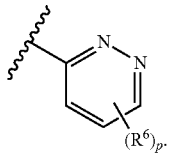

In some embodiments of a compound of Formula (IA), (IB), (IIA), (IIB), or (III), or a pharmaceutically acceptable salt or solvate thereof, $R^3$ is

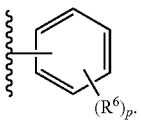

In some embodiments of a compound of Formula (IA), (IB), (IIA), (IIB), or (III) or a pharmaceutically acceptable salt or solvate thereof, each $R^4$ is independently selected from halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, or $C_{1-6}$ alkylhydroxyl. In some embodiments of a compound of Formula (IA), (IB), (IIA), (IIB), or (III), or a pharmaceutically acceptable salt or solvate thereof, each $R^6$ is independently selected from halogen, cyano, $C_{1-6}$ alkyl, or $C_{1-6}$ haloalkyl. In some embodiments of a compound of Formula (IA), (IB), (IIA), (IIB), or (III), or a pharmaceutically acceptable salt or solvate thereof, n is 2. In some embodiments of a compound of Formula (IA), (IB), (IIA), (IIB), or (III), or a pharmaceutically acceptable salt or solvate thereof, n is 1.

Any combination of the groups described above or below for the various variables is contemplated herein. Throughout the specification, groups and substituents thereof are chosen by one skilled in the field to provide stable moieties and compounds.

In another aspect is a pharmaceutical composition comprising a compound of Formula (IA), (IB), (IIA), (IIB), or (III), a pharmaceutically acceptable salt or solvate thereof, and at least one pharmaceutically acceptable excipient.

In another aspect is a method of treating a neurodegenerative disorder in a subject in need thereof, comprising administering to subject a therapeutically effective amount of a compound of Formula (IA), (IB), (IIA), (IIB), or (III), or a pharmaceutically acceptable salt or solvate thereof.

In another aspect is a method of treating neuropathy in a subject in need thereof, comprising administering to subject a therapeutically effective amount of a compound of Formula (IA), (IB), (IIA), (IIB), or (III), or a pharmaceutically acceptable salt or solvate thereof. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is peripheral neuropathy. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is diabetic neuropathy.

In another aspect is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the peripheral nervous system.

In some embodiments of the methods described herein, the method further comprises the administration of one or more immunomodulatory agents. In some embodiments, the one or more immunomodulatory agents are selected from: an IFN-β1 molecule, or the like; a corticosteroid, or the like; a polymer of glutamic acid, lysine, alanine and tyrosine or glatiramer, or the like; an antibody or fragment thereof against alpha-4 integrin or natalizumab, or the like; an anthracenedione molecule or mitoxantrone, or the like; a S1P1 functional modulator or fingolimod, or the like; a NRF2 functional modulator or dimethyl fumarate, or the like; an antibody to the alpha subunit of the IL-2 receptor of T cells (CD25) or daclizumab, or the like; an antibody against CD52 or alemtuzumab, or the like; an antibody against CD20 or ocrelizumab, or the like; and an inhibitor of a dihydroorotate dehydrogenase or teriflunomide, or the like.

In another aspect is a method of modulating muscarinic acetylcholine receptor $M_1$ activity in a subject comprising administering to the subject a compound of Formula (IA), (IB), (IIA), (IIB), or (III), or a pharmaceutically acceptable salt or solvate thereof. In some embodiments, the compound of Formula (IA), (IB), (IIA), (IIB), or (III), or a pharmaceutically acceptable salt or solvate thereof, acts as a selective $M_1$ antagonist.

DETAILED DESCRIPTION

This disclosure is directed, at least in part, to compounds capable of inhibiting the muscarinic acetylcholine $M_1$ receptor.

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

I. Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents). Similarly, $C_{1-x}$ includes $C_{1-2}$, $C_{1-3}$ ... $C_{1-x}$. $C_{1-x}$ refers to the number of carbon atoms that make up the moiety to which it designates (excluding optional substituents).

"Amino" refers to the —$NH_2$ radical.
"Cyano" refers to the —CN radical.
"Hydroxyl" refers to the —OH radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl or $C_{1-15}$ alkyl). In certain embodiments, an alkyl comprises one to thirteen carbon atoms (e.g., $C_1$-$C_{13}$ alkyl or $C_{1-13}$ alkyl). In certain embodiments, an alkyl comprises one to eight carbon atoms (e.g., $C_1$-$C_8$ alkyl or $C_{1-8}$ alkyl). In other embodiments, an alkyl comprises one to six carbon atoms (e.g., $C_1$-$C_6$ alkyl or $C_{1-6}$ alkyl). In other embodiments, an alkyl comprises one to five carbon atoms (e.g., $C_1$-$C_5$ alkyl or $C_{1-5}$ alkyl). In other embodiments, an alkyl comprises one to four carbon atoms (e.g., $C_1$-$C_4$ alkyl or $C_{1-4}$ alkyl). In other embodiments, an alkyl comprises one to three carbon atoms (e.g., $C_1$-$C_3$ alkyl or $C_{1-3}$ alkyl). In other embodiments, an alkyl comprises one to two carbon atoms (e.g., $C_1$-$C_2$ alkyl or $C_{1-2}$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl or $C_{5-15}$ alkyl). In other embodiments, an alkyl comprises five to eight carbon atoms (e.g., $C_5$-$C_8$ alkyl or $C_{5-8}$ alkyl). In other embodiments, an alkyl comprises two to five carbon atoms (e.g., $C_2$-$C_5$ alkyl or $C_{2-5}$ alkyl). In other embodiments, an alkyl comprises three to five carbon atoms (e.g., $C_3$-$C_5$ alkyl or $C_{3-5}$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halogen, cyano, nitro, oxo, thioxo, imino, oximo, trimethylsilyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halogen, cyano, nitro, oxo, thioxo, imino, oximo, trimethylsilyl, —$SR^a$, —$OC(O)$—$R^f$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halogen, cyano, nitro, oxo, thioxo, imino, oximo, trimethylsilyl, —OR', —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halogen, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl (optionally substituted with one or more halogen groups), aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused, bridged or spirocyclic ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl or $C_{3-8}$ cycloalkyl). In other embodiments, a cycloalkyl comprises three to seven carbon atoms (e.g., $C_3$-$C_7$ cycloalkyl or $C_{3-7}$ cycloalkyl). In other embodiments, a cycloalkyl comprises three to six carbon atoms (e.g., $C_3$-$C_6$ cycloalkyl or $C_{3-6}$ cycloalkyl). In other embodiments, a cycloalkyl comprises three to five carbon atoms (e.g., $C_3$-$C_5$ cycloalkyl or $C_{3-5}$ cycloalkyl). In other embodiments, a cycloalkyl comprises three to four carbon atoms (e.g., $C_3$-$C_4$ cycloalkyl or $C_{3-4}$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, bicyclo[1.1.1]pentanyl, spiro[3.3]heptanyl, spiro[4.4]nonanyl, and the like. Unless otherwise stated specifically in the specification, the term "cycloalkyl" is meant to include cycloalkyl radicals optionally substituted by one or more substituents independently selected from alkyl, alkenyl, alkynyl, halogen, haloalkyl, cyano, nitro, aryl, aralkyl, aralkenyl, aralkynyl, cycloalkyl, heterocycloalkyl, heteroaryl, heteroarylalkyl, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)N($R^a$)$_2$ (where t is 1 or 2), where each $R^a$ is independently hydrogen, alkyl, haloalkyl, cycloalkyl, cycloalkylalkyl, aryl (optionally substituted with one or more halogen groups), aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Cycloalkoxy" refers to a radical bonded through an oxygen atom of the formula —O— cycloalkyl, where cycloalkyl is as defined above.

"Halo" or "halogen" refers to bromo, chloro, fluoro or iodo substituents.

"Haloalkyl" refers to an alkyl radical, as defined above, that is substituted by one or more halogen radicals, as defined above.

"Haloalkoxy" refers to an alkoxy radical, as defined above, that is substituted by one or more halogen radicals, as defined above.

"Halocycloalkyl" refers to a cycloalkyl radical, as defined above, that is substituted by one or more halogen radicals, as defined above.

"Halocycloalkoxy" refers to an alkoxy radical, as defined above, that is substituted by one or more halogen radicals, as defined above.

"Alkylhydroxyl" refers to an alkyl radical, as defined above, that is substituted by one or more hydroxyl radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halogen, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)N$(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tOR^a$ (where t is 1 or 2), —$R^b$—S(O)$_tR^a$ (where t is 1 or 2) and —$R^b$—S(O)$_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tOR^a$ (where t is 1 or 2), —$R^b$—S(O)$_tR^a$ (where t is 1 or 2) and —$R^b$—S(O)$_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

"Optional" or "optionally" means that a subsequently described event or circumstance may or may not occur and that the description includes instances when the event or circumstance occurs and instances in which it does not. For example, "optionally substituted aryl" means that the aryl radical is or is not substituted and that the description includes both substituted aryl radicals and aryl radicals having no substitution.

"A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

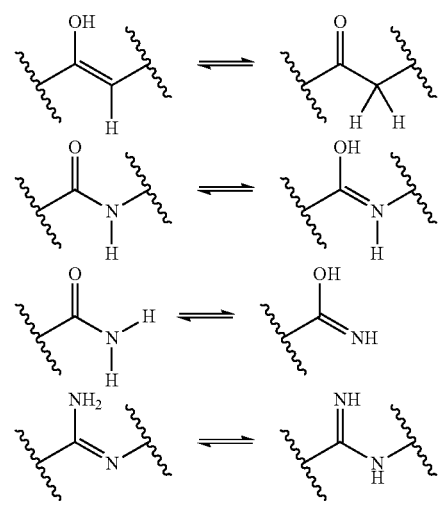

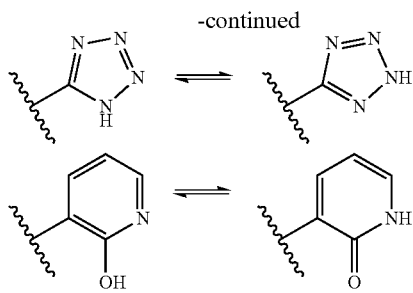

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al, "Pharmaceutical Salts," *Journal of Pharmaceutical Science*, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dib enzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, for example, Bundgard, H., *Design of Prodrugs*, Amsterdam: Elsevier, 1985.). Discussions of prodrugs can also be found in Higuchi, T. et al., "Pro-drugs as Novel Delivery Systems," *A.C.S. Symposium Series*, Vol. 14, and in Roche, E. B., ed. *Bioreversible Carriers in Drug Design*, Oxford: Pergamon Press, 1987.

The term "prodrug" is also meant to include any covalently bonded carriers, which release the active compound in vivo when such prodrug is administered to a mammalian subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol in the active compounds and the like.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. "Hydrates" are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The terms "allosteric site" and "allosteric binding site" refer to a ligand binding site that is topographically distinct from the orthosteric binding site.

The terms "orthosteric site" and "orthosteric binding site" refer to the primary binding site on a receptor that is recognized by an endogenous ligand or agonist for the receptor. For example, the orthosteric site on the muscarinic acetylcholine $M_1$ receptor is the site that acetylcholine binds.

The term "ligand" refers to a natural or synthetic molecule that is capable of binding to or associating with a receptor to form a complex and mediate, prevent, or modify a biological effect. The term "ligand" is meant to encompass allosteric modulators, inhibitors, activators, agonists, antagonists, natural substrates, and analogs of natural substrates.

The terms "natural ligand" and "endogenous ligand" refer to a naturally occurring ligand which binds to a receptor.

The term "mAChR $M_1$ receptor antagonist" refers to any exogenously administered compound or agent that is capable of partially or completely inhibiting, or reversing, the effect of an agonist (e.g. acetylcholine) on the mAChR $M_1$ receptor. The term is inclusive of compounds or agents characterized or described as antagonists, partial antagonists, and negative allosteric modulators. For example, mAChR $M_1$ receptor antagonists can mediate their effects by binding to the orthosteric site or to allosteric sites, or they may interact at unique binding sites not normally involved in the biological regulation of the receptor's activity. Thus, a mAChR $M_1$ receptor antagonist directly or indirectly inhibits the activity of the mAChR $M_1$ receptor in the presence or in the absence of acetylcholine, or another agonist, in an animal, in particular a mammal, for example a human. In various aspects, a mAChR $M_1$ receptor antagonist decreases the activity of the mAChR $M_1$ receptor in a cell in the presence of extracellular acetylcholine. In some embodiments, a compound that is a "mAChR $M_1$ receptor antagonist" includes a compound that is a "mAChR $M_1$ receptor competitive antagonist," a "mAChR $M_1$ receptor noncompetitive antagonist," a "mAChR M1 receptor partial antagonist," or a "mAChR $M_1$ receptor negative allosteric modulator."

The term "mAChR $M_1$ receptor competitive antagonist" refers to any exogenously administered compound or agent that is capable of binding to the orthosteric site of mAChR $M_1$ receptors without activating the receptor. Thus, a competitive antagonist can interact with a mAChR $M_1$ receptor and compete with the endogenous ligand, acetylcholine, for binding to the receptor and decrease the ability of the receptor to transduce an intracellular signal in response to endogenous ligand binding.

The term "mAChR $M_1$ receptor noncompetitive antagonist" refers to any exogenously administered compound or agent that binds to site that is not the orthosteric binding site of mAChR $M_1$ receptors, and is capable of partially or completely inhibiting, or reversing, the effect of an agonist (e.g., acetylcholine) on the mAChR $M_1$ receptor. Thus, a non-competitive antagonist can interact with a mAChR $M_1$ receptor and decrease the binding of the endogenous ligand, acetylcholine, to the receptor and/or decrease the ability of the receptor to transduce an intracellular signal in response to endogenous ligand binding.

The term "mAChR $M_1$ partial antagonist" refers to any exogenously administered compound or agent that can bind to an orthosteric or an allosteric site, but the effect of binding is to only partially block effect of mAChR $M_1$ receptor response to an agonist, e.g., acetylcholine. Thus, a partial antagonist can interact with a mAChR $M_1$ receptor and but is not capable of fully inhibiting the response of the mAChR M1 receptor to an agonist, e.g., acetylcholine.

The term "mAChR $M_1$ negative allosteric modulator" refers to any exogenously administered compound or agent that binds an allosteric site that directly or indirectly inhibits the activity of the mAChR $M_1$ receptor in the presence of acetylcholine, or another agonist, in an animal, in particular a mammal, for example a human. For example, while not intended to be limiting towards the present disclosure, a selective muscarinic $M_1$ negative allosteric modulator can preferentially bind to the muscarinic $M_1$ receptor and decrease muscarinic $M_1$ signaling by acting as a non-competitive antagonist. In one aspect, a mAChR $M_1$ receptor negative allosteric modulator decreases the activity of the mAChR $M_1$ receptor in a cell in the presence of extracellular acetylcholine.

In embodiments, "selective" or "selectivity" or the like in reference to a compound or agent refers to the compound's or agent's ability to cause an increase or decrease in activity of a particular molecular target (e.g., protein, enzyme, etc.) preferentially over one or more different molecular targets (e.g., a compound having selectivity toward muscarinic acetylcholine $M_1$ receptor (mAChR $M_1$) would preferentially inhibit mAChR $M_1$ over other muscarinic receptors). In embodiments, a "muscarinic acetylcholine $M_1$ receptor selective compound" or "mAChR $M_1$-selective compound" refers to a compound (e.g., compounds described herein) having selectivity towards muscarinic acetylcholine $M_1$ receptor (mAChR $M_1$). In embodiments, the compound (e.g., compound described herein) is about 5-fold, 10-fold, 20-fold, 30-fold, 40-fold, 50-fold, or about 100-fold more selective for muscarinic acetylcholine $M_1$ receptor (mAChR $M_1$) over one or more of the mAChR $M_2$, $M_3$, $M_4$, or $M_5$ receptors. In embodiments, the compound (e.g., compound described herein) is at least 5-fold, 10-fold, 20-fold, 30-fold, 40-fold, 50-fold, or at least 100-fold more selective for muscarinic acetylcholine $M_1$ receptor (mAChR $M_1$) over one or more of the mAChR $M_2$, $M_3$, $M_4$, or $M_5$ receptors.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the subject is a human.

As used herein, "treatment" or "treating" or "palliating" or "ameliorating" are used interchangeably herein. These terms refer to an approach for obtaining beneficial or desired results including but not limited to therapeutic benefit and/or prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

As used herein, "$EC_{50}$" is intended to refer to the concentration of a substance (e.g., a compound or a drug) that is required for 50% activation or enhancement of a biological process, or component of a process, including a protein, subunit, organelle, ribonucleoprotein, etc. For example, $EC_{50}$ can refer to the concentration of agonist that provokes a response halfway between the baseline and maximum response in an in vitro assay. In some embodiments, in vitro assay systems utilize a cell line that either expresses endogenously a target of interest or has been transfected with a suitable expression vector that directs expression of a recombinant form of the target.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. For example, $IC_{50}$ refers to the half maximal (50%) inhibitory concentration (IC) of a substance as determined in a suitable assay. For example, an $IC_{50}$ for mAChR $M_1$ receptor can be determined in an in vitro assay system.

II. Compounds

This disclosure provides compounds which are antagonists of the muscarinic acetylcholine $M_1$ receptor (mAChR $M_1$). These compounds, and compositions comprising these compounds, are useful for the treatment or prevention of neurological disorders. In some embodiments, the compounds described herein are useful for treating multiple sclerosis.

In one aspect is provided a compound of Formula (IA) or (IB):

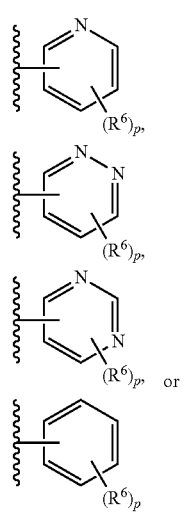

Formula (IA)

Formula (IB)

wherein:

Y is a —CH$_2$—, —CH$_2$CH$_2$—, or —CH$_2$OCH$_2$—;

$R^1$ is

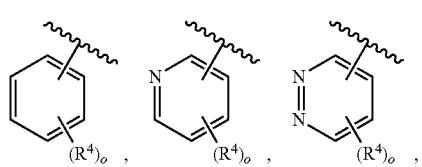

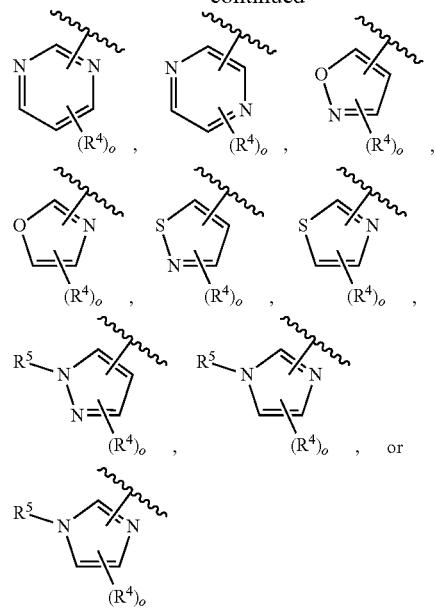

each $R^2$ is independently selected from hydrogen, deuterium, or $C_{1-6}$ alkyl;

$R^3$ is

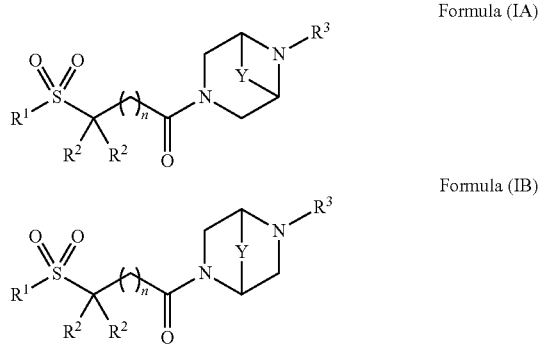

each $R^4$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^5$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each $R^6$ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3;

or a pharmaceutically acceptable salt or solvate thereof, provided that the aforementioned combinations do not violate the rules of valency known to those skilled in the art.

In one aspect is provided a compound of Formula (IIA) or (IIB):

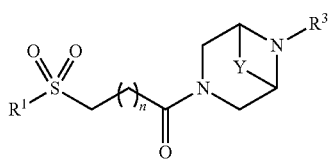

Formula (IIA)

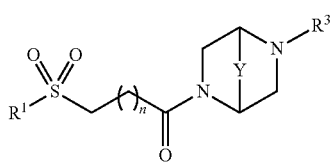

Formula (IIB)

wherein:

Y is a —CH$_2$—, —CH$_2$CH$_2$—, or —CH$_2$OCH$_2$—;

R$^1$ is

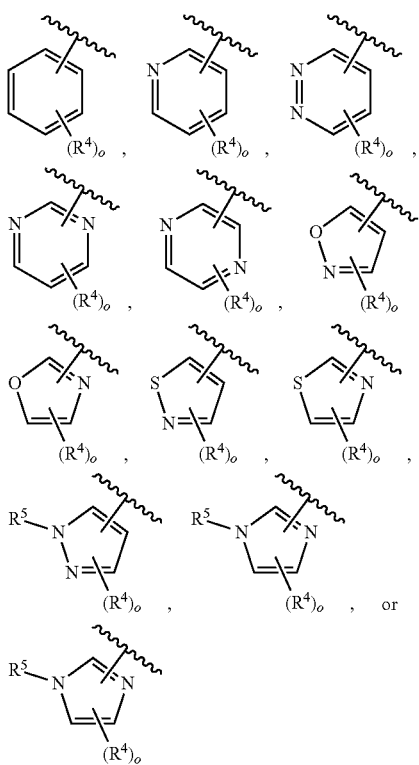

R$^3$ is

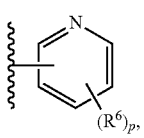

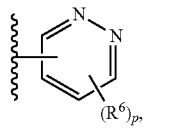

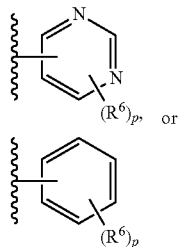

-continued each R$^4$ is independently selected from hydroxyl, halogen, cyano, C$_{1-6}$ alkyl, C$_{1-6}$ alkoxy, C$_{1-6}$ haloalkyl, C$_{1-6}$ haloalkoxy, C$_{3-6}$ cycloalkyl, C$_{3-6}$ cycloalkoxy, C$_{3-6}$ halocycloalkyl, C$_{3-6}$ halocycloalkoxy, C$_{1-6}$ alkylhydroxyl, or heterocycloalkyl;

R$^5$ is hydrogen, C$_{1-6}$ alkyl, C$_{1-6}$ haloalkyl, C$_{3-6}$ cycloalkyl, C$_{3-6}$ halocycloalkyl, heterocycloalkyl, aryl, or heteroaryl;

each R$^6$ is independently selected from halogen, cyano, C$_{1-6}$ alkyl, C$_{3-6}$ cycloalkyl, C$_{1-6}$ alkoxy, C$_{1-6}$ haloalkyl, C$_{3-6}$ halocycloalkyl, or C$_{1-6}$ haloalkoxy;

n is 1 or 2;

o is 0, 1, or 2; and p is 0, 1, 2, or 3;

or a pharmaceutically acceptable salt or solvate thereof, provided that the aforementioned combinations do not violate the rules of valency known to those skilled in the art.

In another aspect is provided a compound of Formula (III):

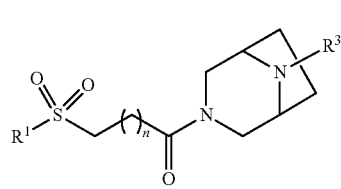

Formula (III)

wherein:

R$^1$ is

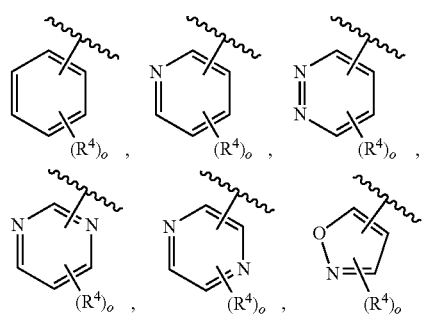

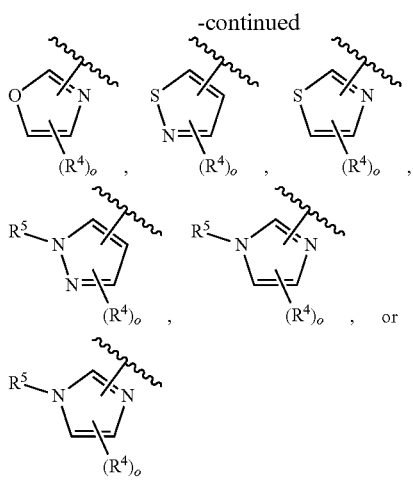

R³ is

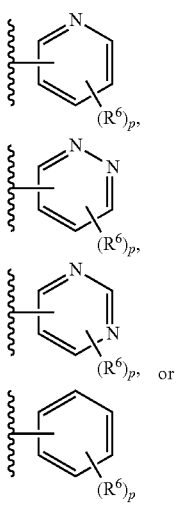

each R⁴ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

R⁵ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each R⁶ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3;

or a pharmaceutically acceptable salt or solvate thereof, provided that the aforementioned combinations do not violate the rules of valency known to those skilled in the art.

In some embodiments of a compound of Formula (IA), (IB), (IIA), (IIB), or (III), or a pharmaceutically acceptable salt or solvate thereof, R¹ is

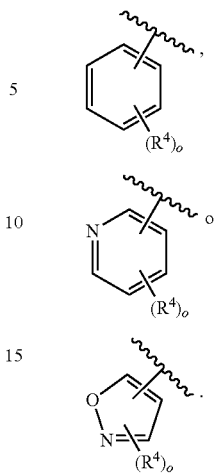

In some embodiments, R¹ is

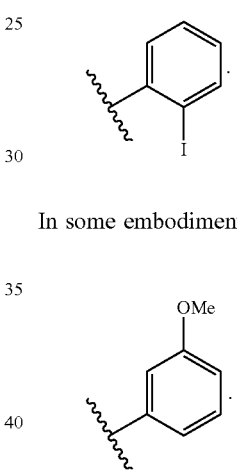

In some embodiments, R¹ is

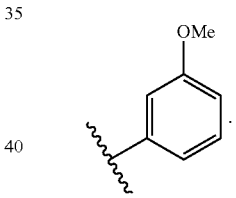

In some embodiments, R¹ is

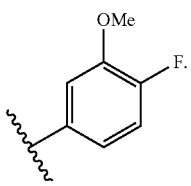 [SMILES: *c1ccc(F)c(OC)c1]

In some embodiments, R¹ is

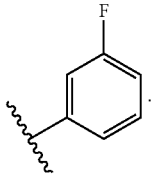

In some embodiments, R¹ is
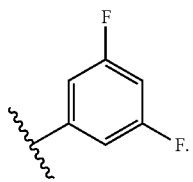 [SMILES: *c1cc(F)cc(F)c1]
In some embodiments, R¹ is
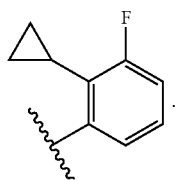 [SMILES: *c1cccc(F)c1C1CC1]
In some embodiments, R¹ is
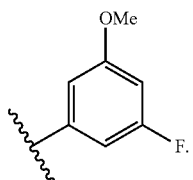 [SMILES: *c1cc(F)cc(OC)c1]
In some embodiments, R¹ is
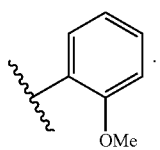
In some embodiments, R¹ is
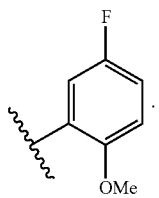 [SMILES: *c1cc(F)ccc1OC]
In some embodiments, R¹ is
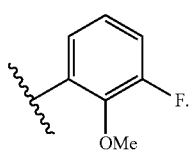
In some embodiments, R¹ is
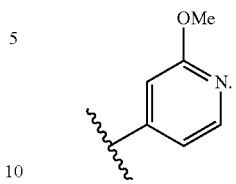
In some embodiments, R¹ is
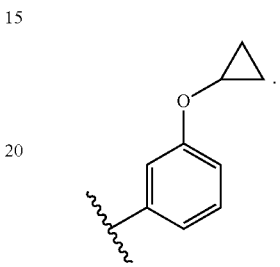
In some embodiments, R¹ is
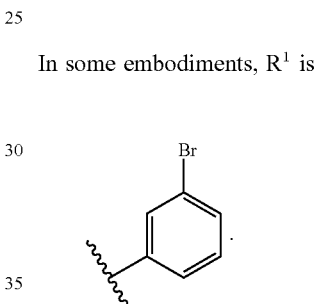
In some embodiments, R¹ is
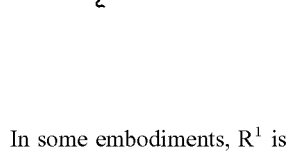
In some embodiments, R¹ is
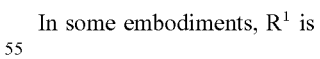
In some embodiments, R¹ is
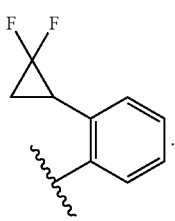

In some embodiments, R¹ is
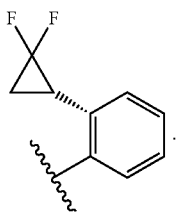
In some embodiments, R¹ is
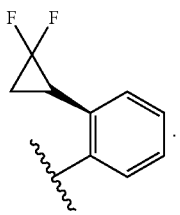
In some embodiments, R¹ is
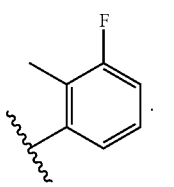
In some embodiments, R¹ is
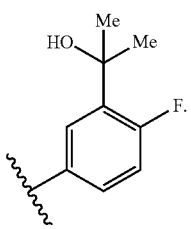 [SMILES: *c1ccc(F)c(C(C)(C)O)c1]
In some embodiments, R¹ is
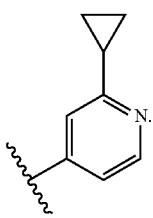 [SMILES: *c1ccnc(C2CC2)c1]
In some embodiments, R¹ is
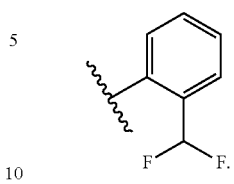
In some embodiments, R¹ is
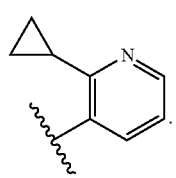 [SMILES: *c1cccnc1C1CC1]
In some embodiments, R¹ is
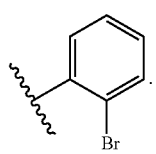
In some embodiments, R¹ is
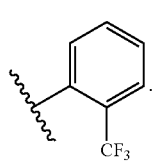
In some embodiments, R¹ is
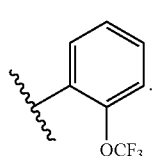
In some embodiments, R¹ is
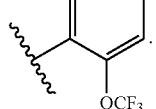

In some embodiments, $R^1$ is

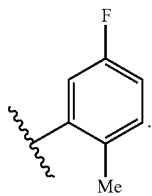

In some embodiments, $R^1$ is

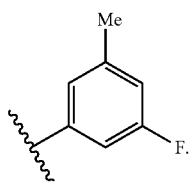 [SMILES: *c1cc(C)cc(F)c1]

In some embodiments, $R^1$ is

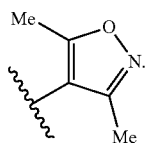 [SMILES: *c1c(C)noc1C]

In some embodiments of a compound of Formula (IA), (IB), (IIA), (IIB), or (III), or a pharmaceutically acceptable salt or solvate thereof, $R^3$ is

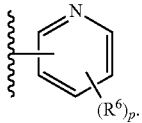

In some embodiments, $R^3$ is

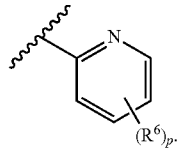

In some embodiments, $R^3$ is

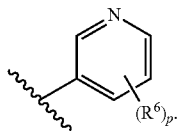

In some embodiments, $R^3$ is

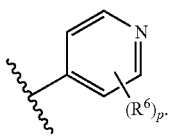

In some embodiments, $R^3$ is

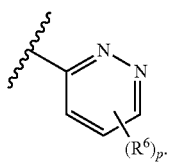

In some embodiments, $R^3$ is

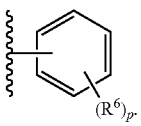

In some embodiments of a compound of Formula (IA), (IB), (IIA), (IIB), or (III), or a pharmaceutically acceptable salt or solvate thereof, $R^6$ is selected from halogen, cyano, $C_{1-6}$ alkyl, or $C_{1-6}$ haloalkyl. In some embodiments, $R^6$ is selected from fluorine, cyano, methyl, or trifluoromethyl.

In some embodiments of a compound of Formula (IA), (IB), (IIA), (IIB), or (III), or a pharmaceutically acceptable salt or solvate thereof, p is 0 to 1, 0 to 2, 1 to 2, 1 to 3, or 2 to 3. In some embodiments, p is 0. In some embodiments, p is 1. In some embodiments, p is 2. In some embodiments, p is 3.

In some embodiments of a compound of Formula (IA), (IB), (IIA), (IIB), or (III), or a pharmaceutically acceptable salt or solvate thereof, $R^3$ is

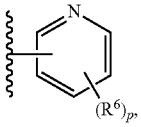

p is 1, and $R^6$ is selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy. In some embodiments, $R^3$ is

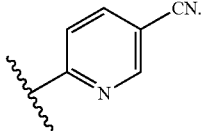 [SMILES: *c1ccc(C#N)cn1]

In some embodiments, $R^3$ is

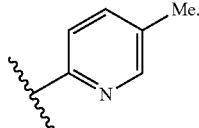 [SMILES: *c1ccc(C)cn1]

In some embodiments, $R^3$ is

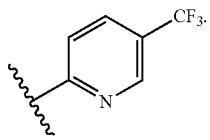 [SMILES: *c1ccc(C(F)(F)F)cn1]

In some embodiments, $R^3$ is

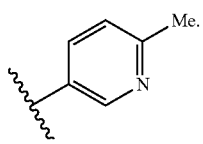 [SMILES: *c1ccc(C)nc1]

In some embodiments of a compound of Formula (IA), (IB), (IIA), (IIB), or (III), or a pharmaceutically acceptable salt or solvate thereof of, $R^3$ is

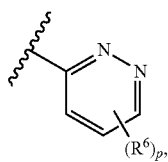

p is 1, and $R^6$ is selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy. In some embodiments, $R^6$

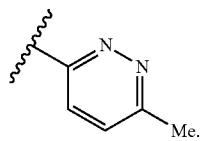 [SMILES: *c1ccc(C)nn1]

In some embodiments, $R^6$

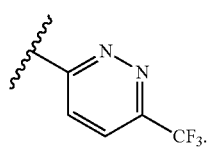

In some embodiments of a compound of Formula (IA), (IB), (IIA), (IIB), or (III), or a pharmaceutically acceptable salt or solvate thereof, $R^3$ is

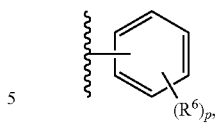

p is 2, $R^6$ is selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy. In some embodiments, $R^3$ is

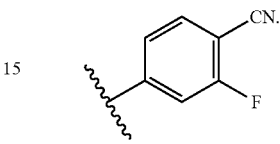

In some embodiments, $R^3$ is

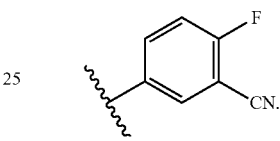

Any combination of the groups described above or below for the various variables is contemplated herein. Throughout the specification, groups and substituents thereof are chosen by one skilled in the field to provide stable moieties and compounds.

In some embodiments is a compound selected from:

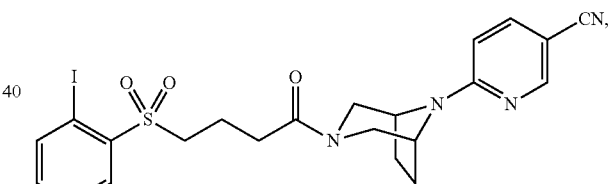

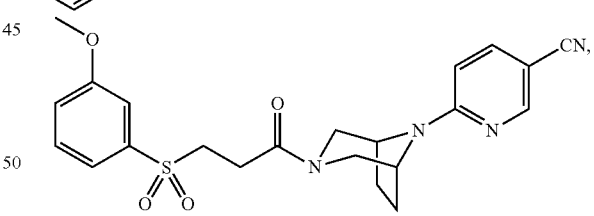

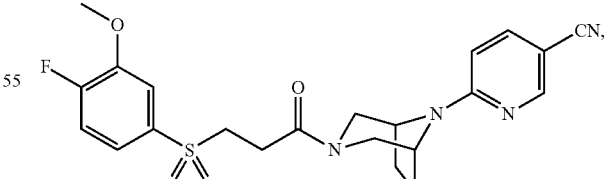

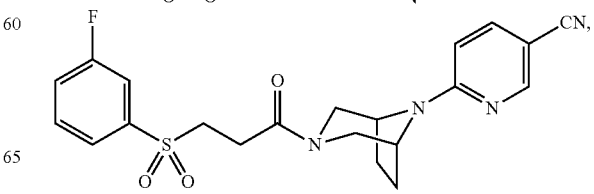

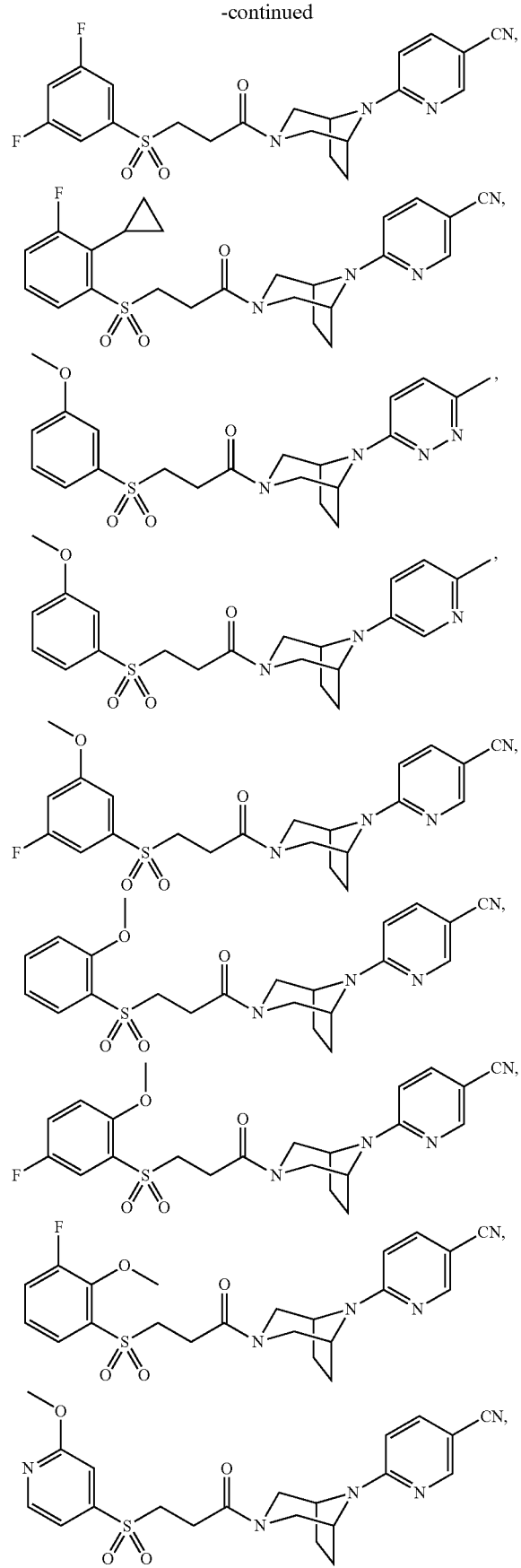
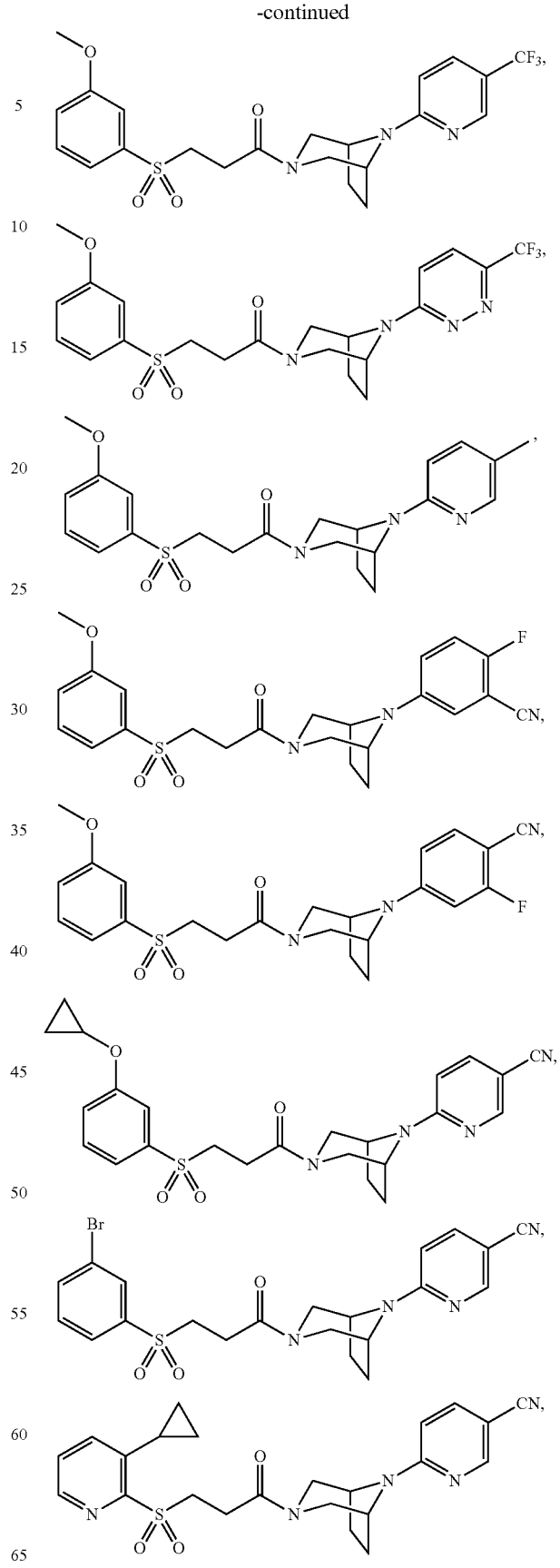

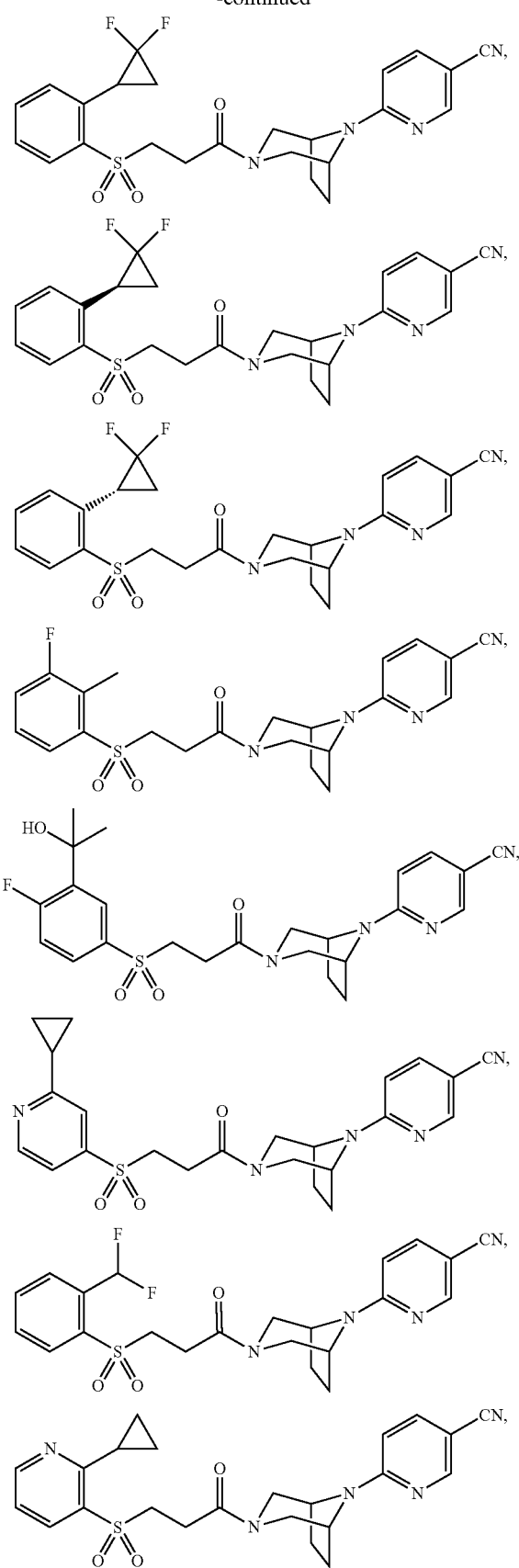
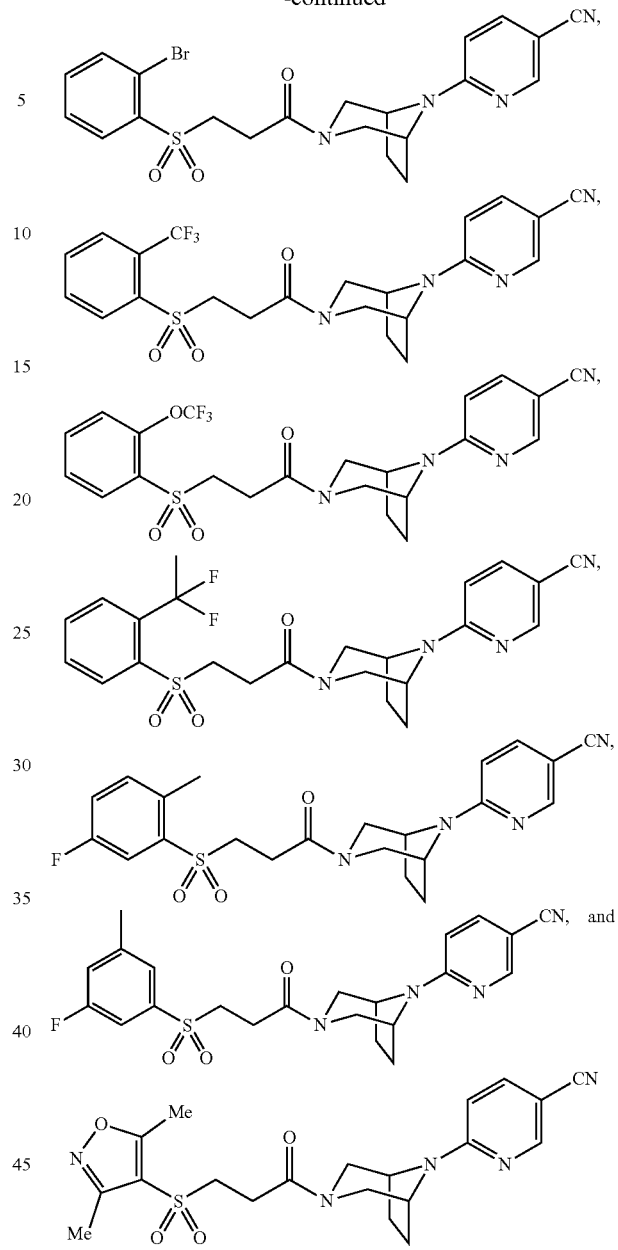

or a pharmaceutically acceptable salt or solvate thereof.

In embodiments, the compound is useful as a comparator compound. In embodiments, the comparator compound can be used to assess the activity of a test compound in an assay (e.g., an assay as described herein, for example in the examples section, figures, or tables).

In embodiments, the compound is a compound described herein (e.g., in the Compounds section, Examples Section, Methods Section, or in a claim, table, or figure).

III. Further Forms of the Compounds

Isomers

The compounds described herein include all possible tautomers within the formulas described herein. Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

In some situations, the compounds described herein possess one or more chiral centers and each center exists in the (R)-configuration, or (S)-configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

Labeled Compounds

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium (2H), tritium (3H), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present disclosure, whether radioactive or not, are encompassed within the scope of the present disclosure.

In certain embodiments, the compounds disclosed herein have some or all of the 1H atoms replaced with 2H atoms. The methods of synthesis for deuterium-containing compounds are known in the art. In some embodiments deuterium substituted compounds are synthesized using various methods such as described in: Dean, D. C.; "Recent Advances in the Synthesis and Applications of Radiolabeled Compounds for Drug Discovery and Development," *Curr. Pharm. Des.*, 2000, 6(10); George W.; Varma, R. S., "The Synthesis of Radiolabeled Compounds via Organometallic Intermediates," *Tetrahedron*, 1989, 45(21), 6601-21; and Evans, E. A., "Synthesis of radiolabeled compounds," *J. Radioanal. Chem.*, 1981, 64(1-2), 9-32.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The present disclosure provides for methods of treating diseases by administering such solvates. The present disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The present disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present disclosure. The amino acid residues include but are not limited to the naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemi succinates, dimethylaminoacetates and phosphoryloxymethyloxycarbonyls, as outlined in Fleisher, D. et al., "Improved oral drug delivery: solubility limitations overcome by the use of prodrugs," *Advanced Drug Delivery Reviews*, 1996, 19, 115-130.

Amine derived prodrugs include, but are not limited to the following groups and combinations of groups:

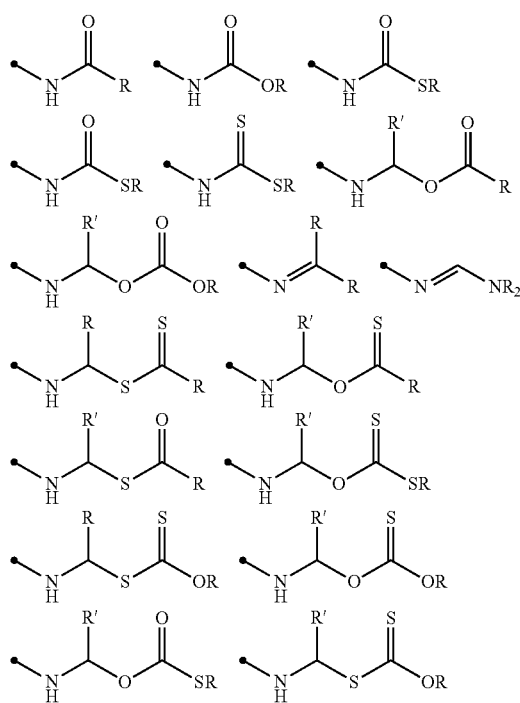

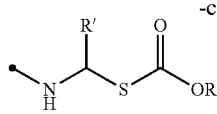

as well as sulfonamides and phosphonamides.

IV. Pharmaceutical Compositions

In certain embodiments, the compound of Formula (IA), (IB), (IIA), (IIB), or (III) as described herein is administered as a pure chemical. In some embodiments, the compound of Formula (IA), (IB), (IIA), (IIB), or (III) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Gennaro, A. R., "Remington: The Science and Practice of Pharmacy," 21$^{st}$ ed., Easton: Lippincott Williams & Wilkins, 2005.

Accordingly, provided herein is a pharmaceutical composition comprising at least one compound of Formula (IA), (IB), (IIA), (IIB), or (III) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (IA), or a pharmaceutically acceptable salt thereof.

One embodiment provides a pharmaceutical composition comprising a pharmaceutically acceptable excipient and a compound of Formula (IB), or a pharmaceutically acceptable salt thereof.

One embodiment provides a pharmaceutical composition comprising a pharmaceutically acceptable excipient and a compound of Formula (IIA), or a pharmaceutically acceptable salt thereof.

One embodiment provides a pharmaceutical composition comprising a pharmaceutically acceptable excipient and a compound of Formula (IIB), or a pharmaceutically acceptable salt thereof.

One embodiment provides a pharmaceutical composition comprising a pharmaceutically acceptable excipient and a compound of Formula (III), or a pharmaceutically acceptable salt thereof.

In certain embodiments, the compound of Formula (IA), (IB), (IIA), (IIB), or (III) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These pharmaceutical compositions include those suitable for oral, rectal, topical, buccal, parenteral (e.g., subcutaneous, intramuscular, intradermal, or intravenous), vaginal, ophthalmic, or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid pre-formulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (e.g., Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (IA), (IB), (IIA), (IIB), or (III) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Disclosed compounds are administered to subjects or patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

V. Methods of Using the Compounds and Compositions

Antagonists of mAChR $M_1$

The muscarinic acetylcholine receptor $M_1$ (mAChR $M_1$) is found in both the central and peripheral nervous systems, particularly in the cerebral cortex and sympathetic ganglia. Notably, $M_1$ is expressed on oligodendrocyte precursor cells (OPCs) in the central nervous system. Over time, OPCs will differentiate into myelin-producing oligodendrocytes. Myelin is indispensable for action potential conduction along the axon and its loss has been attributed to neurodegenerative disorders, specifically multiple sclerosis. In some embodiments, selective mAChR $M_1$ antagonists accelerate OPC differentiation into oligodendrocytes. In some embodiments, selective mAChR $M_1$ antagonists are useful in the treatment of demyelinating disorders, such as multiple sclerosis. In some embodiments, selective mAChR $M_1$ antagonists are useful in treating epileptic disorders and certain movement disorders, including Parkinson's disease, dystonia, and fragile X syndrome.

In one aspect, the compounds disclosed herein are selective antagonists of the muscarinic acetylcholine $M_1$ receptor (mAChR $M_1$). In some embodiments, the compounds disclosed herein are selective antagonists of the muscarinic acetylcholine $M_1$ receptor (mAChR $M_1$) over one or more of the mAChR $M_2$, $M_3$, $M_4$, or $M_5$ receptors. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_2$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_3$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_4$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_5$. In some embodiments, a compound disclosed herein exhibits an $IC_{50}$ for the mAChR $M_1$ response which is about 5-fold less, about 10-fold less, about 20-fold less, about 30-fold less, about 50-fold less, about 100-fold less, or >100-fold less than that for mAChR $M_2$, $M_3$, $M_4$, or $M_5$, or combinations thereof.

Treatment Methods

The compounds disclosed herein are useful for treating, preventing, ameliorating, controlling or reducing the risk of a variety of disorders wherein the patient or subject would benefit from antagonism of the muscarinic acetylcholine $M_1$ receptor.

In one aspect, a treatment can include selective $M_1$ receptor antagonism to an extent effective to affect cholinergic activity. Thus, disorders for which the compounds disclosed herein are useful can be associated with cholinergic activity, for example cholinergic hyperfunction. In some embodiments, provided herein is a method of treating or preventing a disorder in a subject comprising the step of administering to the subject a compound disclosed herein, or a pharmaceutically acceptable salt or solvate thereof, or a pharmaceutical composition described herein in a dosage and amount effective to treat the disorder in the subject.

Provided herein is a method for the treatment of one or more disorders, for which muscarinic acetylcholine receptor inhibition is predicted to be beneficial, in a subject comprising the step of administering to the subject a compound disclosed herein, or a pharmaceutically acceptable salt or solvate thereof, or a pharmaceutical composition described herein in a dosage and amount effective to treat the disorder in the subject.

In some embodiments provided herein is a method of treating a neurodegenerative disorder in a subject in need thereof, comprising administering to subject a therapeutically effective amount of a compound of Formula (IA), (IB), (IIA), (IIB), or (III), or a pharmaceutically acceptable salt or solvate thereof.

In some embodiments provided herein is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is peripheral neuropathy. In some embodiments is a method of treating neuropathy in a subject in need thereof, comprising administering to the subject a therapeutically effective amount of a compound of Formula (IA), (IB), (IIA), (IIB), or (III), or a pharmaceutically acceptable salt or solvate thereof, wherein the neuropathy is diabetic neuropathy.

In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the central nervous system. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is multiple sclerosis. In some embodiments is a method of treating a demyelinating disease in a subject in need thereof, comprising administering to the subject a therapeutically effective amount of a compound of Formula (IA), (IB), (IIA), (IIB), or (III), or a pharmaceutically acceptable salt or solvate thereof, wherein the demyelinating disease is a demyelinating disease of the peripheral nervous system.

In some embodiments is a method of modulating muscarinic acetylcholine receptor $M_1$ activity in a subject comprising administering to the subject a compound of Formula (IA), (IB), (IIA), (IIB), or (III), or a pharmaceutically acceptable salt or solvate thereof. In some embodiments, the compound of Formula (IA), (IB), (IIA), (IIB), or (III), or a pharmaceutically acceptable salt or solvate thereof acts as a selective $M_1$ antagonist.

VI. Combination Therapy

Also contemplated herein are combination therapies, for example, co-administering a disclosed compound and an additional active agent, as part of a specific treatment regimen intended to provide the beneficial effect from the co-action of these therapeutic agents. In some embodiments, a compound described herein is administered in combination with one or more immunomodulatory agents. In some embodiments, a compound described herein is administered in combination with one or more immunomodulatory agents, wherein the immunomodulatory agents are selected from an IFN-β1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or other S1P1 functional modulator; a dimethyl fumarate or other NRF2 functional modulator; an antibody to the alpha subunit of the IL-2 receptor of T cells (CD25) or daclizumab; an antibody against CD52 or alemtuzumab; an antibody against CD20 or ocrelizumab; and an inhibitor of a dihydroorotate dehydrogenase or teriflunomide. In some embodiments, the immunomodulatory agent is an IFN-β1 molecule. In some embodiments, the immunomodulatory agent is a corticosteroid. In some embodiments, the immunomodulatory agent is a polymer of glutamic acid, lysine, alanine and tyrosine or glatiramer. In some embodiments, the immunomodulatory agent is an antibody or fragment thereof against alpha-4 integrin or natalizumab. In some embodiments, the immunomodulatory agent is an anthracenedione molecule or mitoxantrone. In some embodiments, the immunomodulatory agent is a fingolimod or other S1P1 functional modulator. In some embodiments, the immunomodulatory agent is a dimethyl fumarate or other NRF2 functional modulator. In some embodiments, the immunomodulatory agent is an antibody to the alpha subunit of the IL-2 receptor of T cells (CD25) or daclizumab. In some embodiments, the immunomodulatory agent is an antibody against CD52 or alemtuzumab. In some embodiments, the immunomodulatory agent is an antibody against CD20 or ocrelizumab. In some embodiments, the immunomodulatory agent is an inhibitor of a dihydroorotate dehydrogenase or teriflunomide.

The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

VII. Embodiments

Embodiment P1. A compound, or a pharmaceutically acceptable salt or solvate thereof, having the structure of Formula (IA) or (IB):

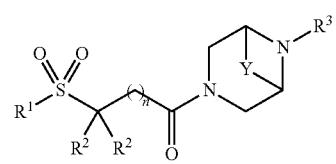

Formula (IA)

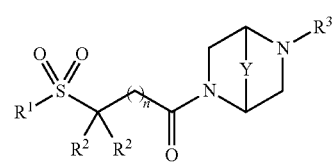

Formula (IB)

wherein:

Y is —$CH_2$—, —$CH_2CH_2$—, or —$CH_2OCH_2$—;

$R^1$ is

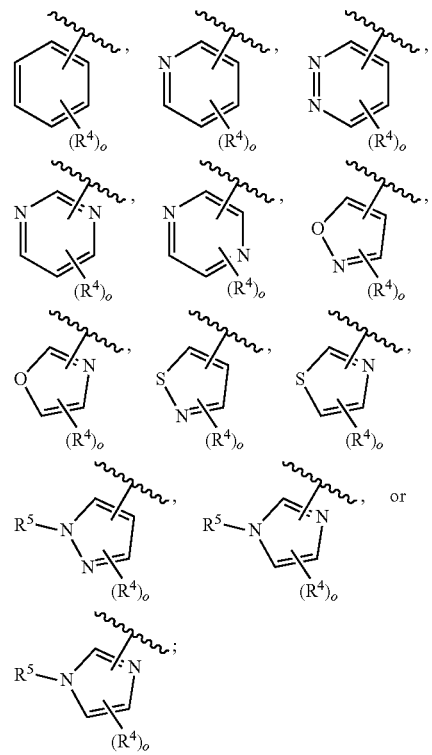

each $R^2$ is independently selected from hydrogen, deuterium, or $C_{1-6}$ alkyl;

$R^3$ is

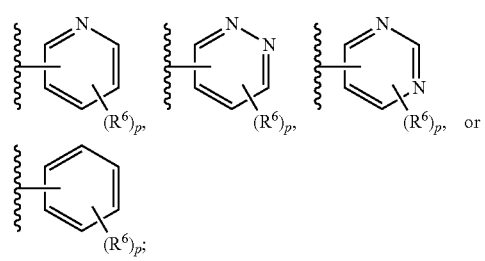

each $R^4$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^5$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each $R^6$ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3.

Embodiment P2. The compound of embodiment P1, or a pharmaceutically acceptable salt or solvate thereof, having the structure of Formula (IIA) or (IIB):

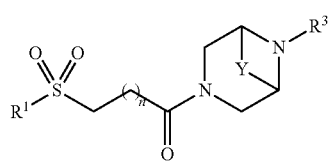

Formula (IIA)

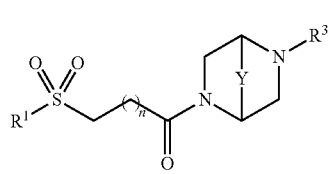

Formula (IIB)

wherein:

Y is —$CH_2$—, —$CH_2CH_2$—, or —$CH_2OCH_2$—;

$R^1$ is

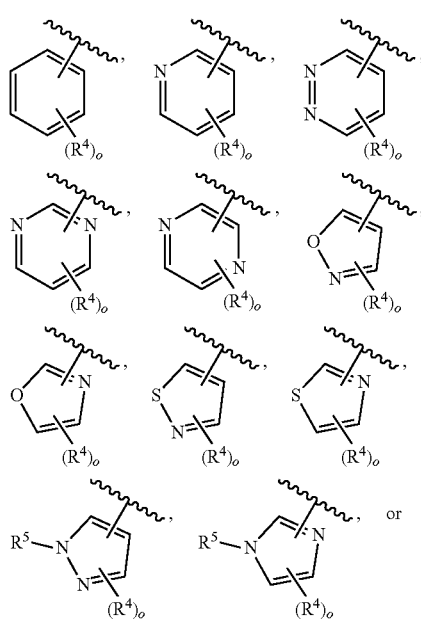

$R^3$ is

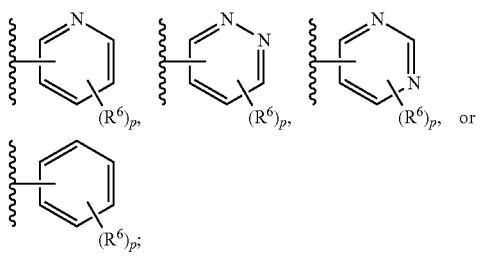

each $R^4$ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

$R^5$ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each $R^6$ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3.

Embodiment P3. The compound of embodiment P1, or a pharmaceutically acceptable salt or solvate thereof, having the structure of Formula (III):

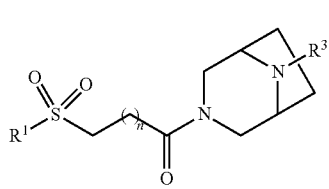

Formula (III)

wherein:

$R^1$ is

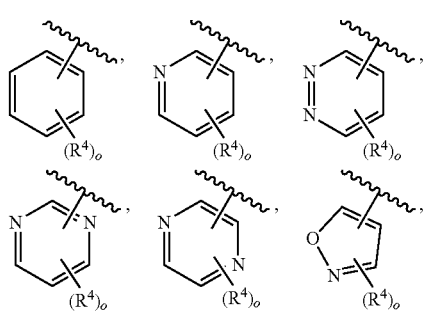

-continued

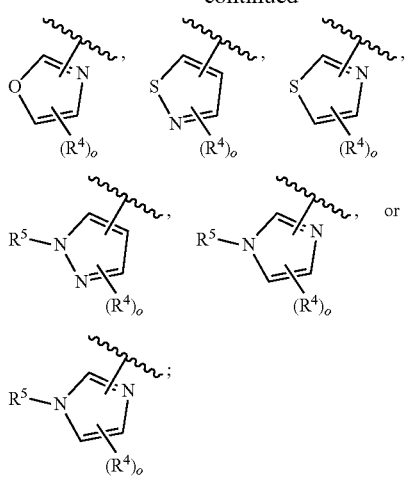

R³ is

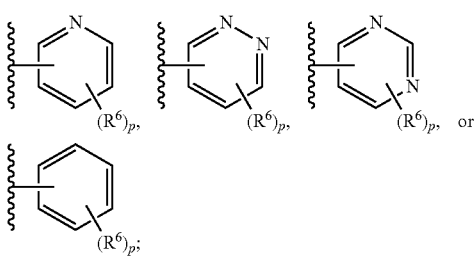

each R⁴ is independently selected from hydroxyl, halogen, cyano, $C_{1-6}$ alkyl, $C_{1-6}$ alkoxy, $C_{1-6}$ haloalkyl, $C_{1-6}$ haloalkoxy, $C_{3-6}$ cycloalkyl, $C_{3-6}$ cycloalkoxy, $C_{3-6}$ halocycloalkyl, $C_{3-6}$ halocycloalkoxy, $C_{1-6}$ alkylhydroxyl, or heterocycloalkyl;

R⁵ is hydrogen, $C_{1-6}$ alkyl, $C_{1-6}$ haloalkyl, $C_{3-6}$ cycloalkyl, $C_{3-6}$ halocycloalkyl, heterocycloalkyl, aryl, or heteroaryl;

each R⁶ is independently selected from halogen, cyano, $C_{1-6}$ alkyl, $C_{3-6}$ cycloalkyl, $C_{1-6}$ alkoxy, $C_{1-6}$ haloalkyl, $C_{3-6}$ halocycloalkyl, or $C_{1-6}$ haloalkoxy;

n is 1 or 2;

o is 0, 1, or 2; and p is 0, 1, 2, or 3.

Embodiment P4. The compound of any one of embodiments P1-P3, or a pharmaceutically acceptable salt thereof, wherein R¹ is

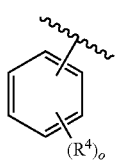

Embodiment P5. The compound of embodiment P4, or a pharmaceutically acceptable salt or solvate thereof, wherein R¹ is

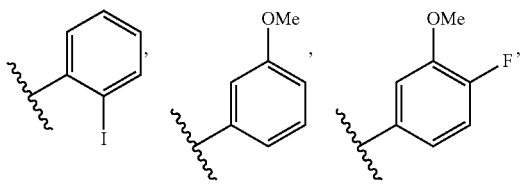
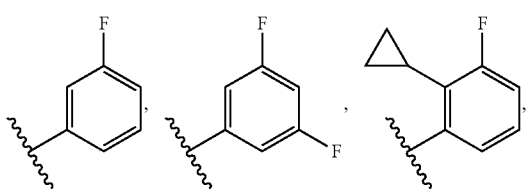
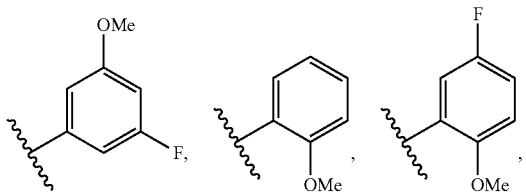
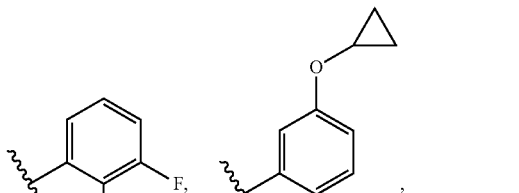
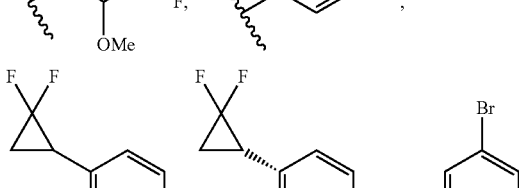
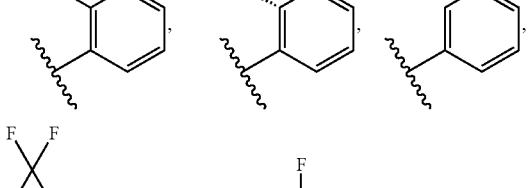
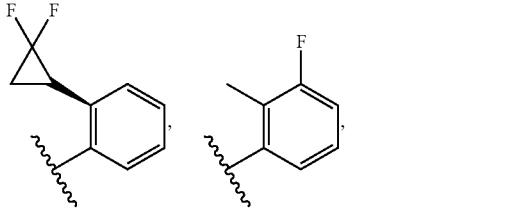
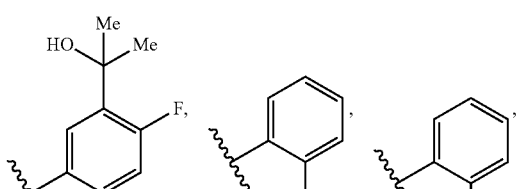
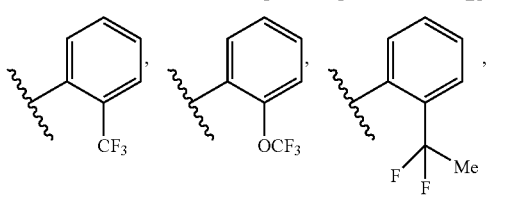

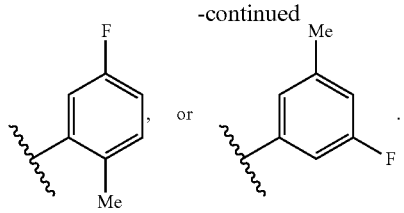

Embodiment P6. The compound of any one of embodiments P1-P3, or a pharmaceutically acceptable salt or solvate thereof, wherein $R^1$ is

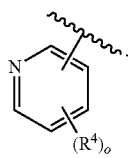

Embodiment P7. The compound of embodiment P6 or a pharmaceutically acceptable salt or solvate thereof, wherein $R^1$ is

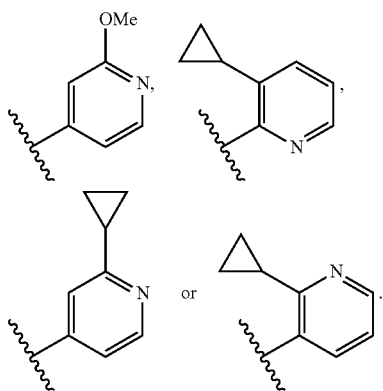

Embodiment P8. The compound of any one of embodiments P1-P3, or a pharmaceutically acceptable salt or solvate thereof, wherein $R^1$ is

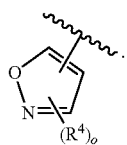

Embodiment P9. The compound of embodiment P8 or a pharmaceutically acceptable salt or solvate thereof, wherein $R^1$ is

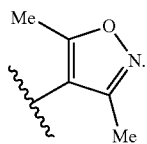

Embodiment P10. The compound of any one of embodiments P1-P9, or a a pharmaceutically acceptable salt or solvate thereof, wherein $R^3$ is

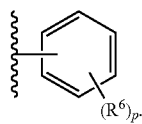

Embodiment P11. The compound of embodiment P10, wherein $R^3$ is

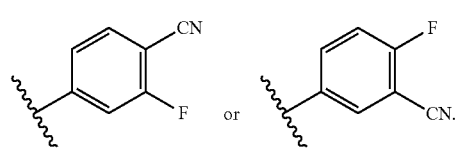 [SMILES: *c1ccc(C#N)c(F)c1 ; *c1ccc(F)c(C#N)c1]

Embodiment P12. The compound of any one of embodiments P1-P9, or a a pharmaceutically acceptable salt or solvate thereof, wherein $R^3$ is

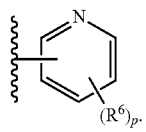

Embodiment P13. The compound of embodiment P12, or a a pharmaceutically acceptable salt or solvate thereof, wherein $R^3$ is

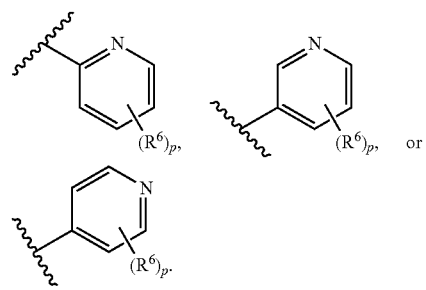

Embodiment P14. The compound of embodiment P13, wherein embodiments, $R^3$ is

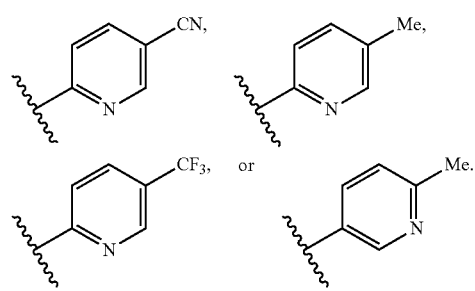

Embodiment P15. The compound of any one of embodiments P1-P9, or a a pharmaceutically acceptable salt or solvate thereof, wherein R³ is

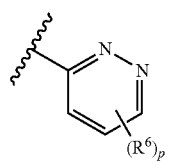

Embodiment P16. The compound of embodiment P15, wherein embodiments, R³ is

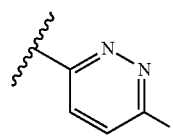 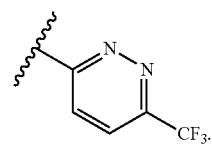

Embodiment P17. The compound of any one of embodiments P1-P16, wherein n is 1.

Embodiment P18. The compound of any one of embodiments P1-P16, wherein n is 2.

Embodiment P19. A compound selected from:

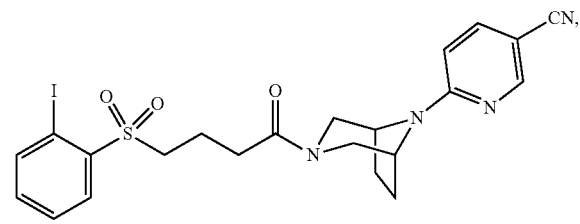

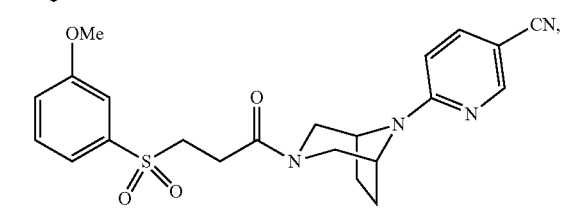

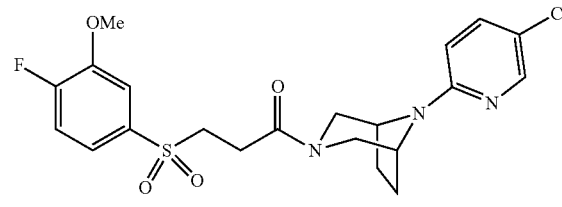

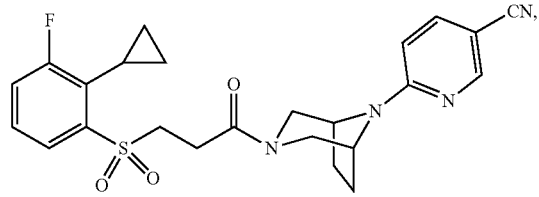

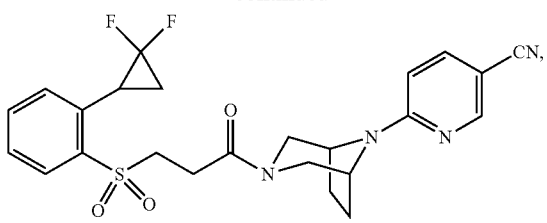

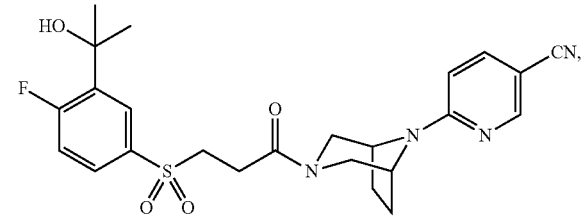

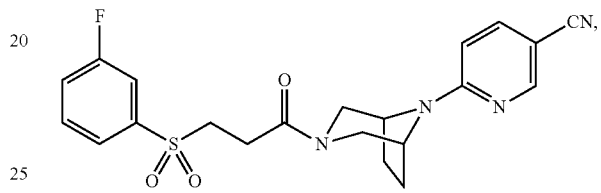

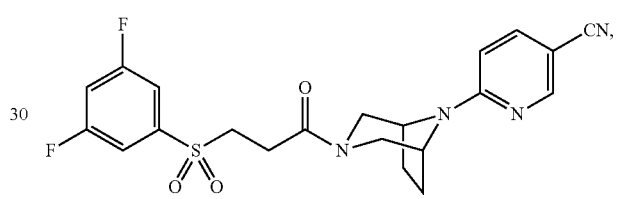

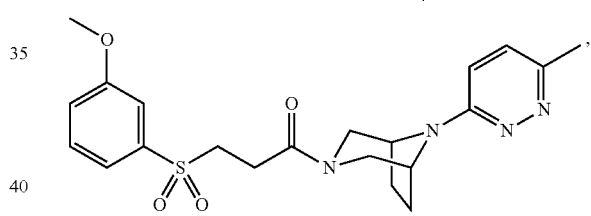

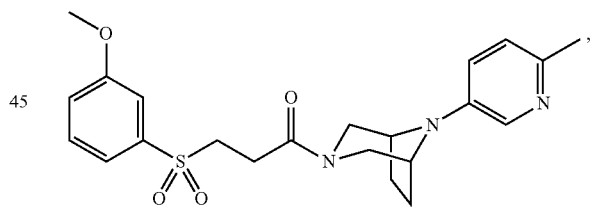

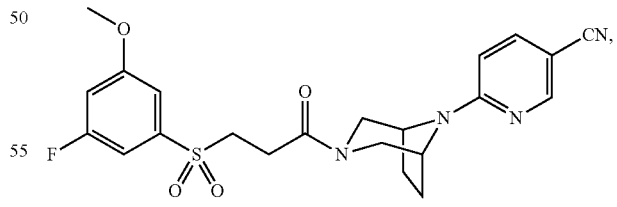

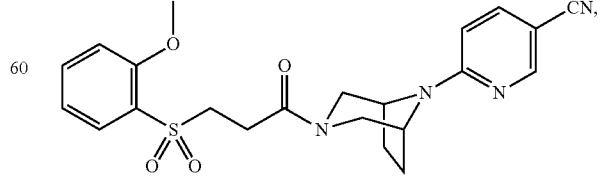

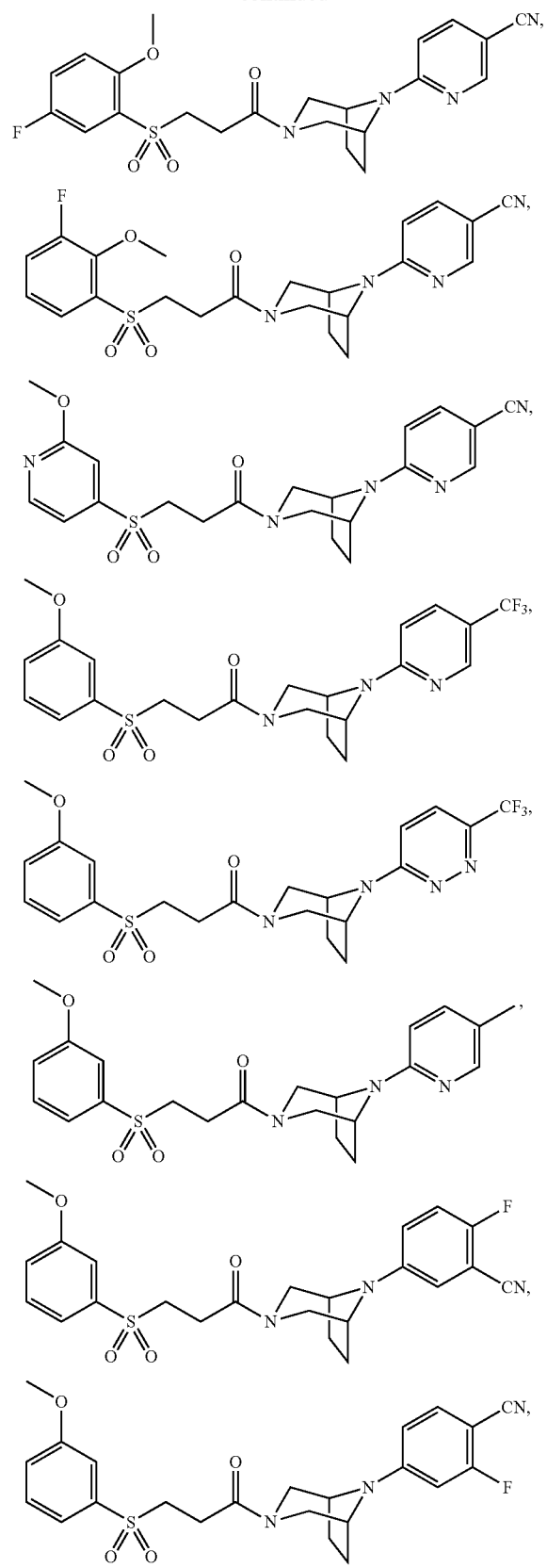
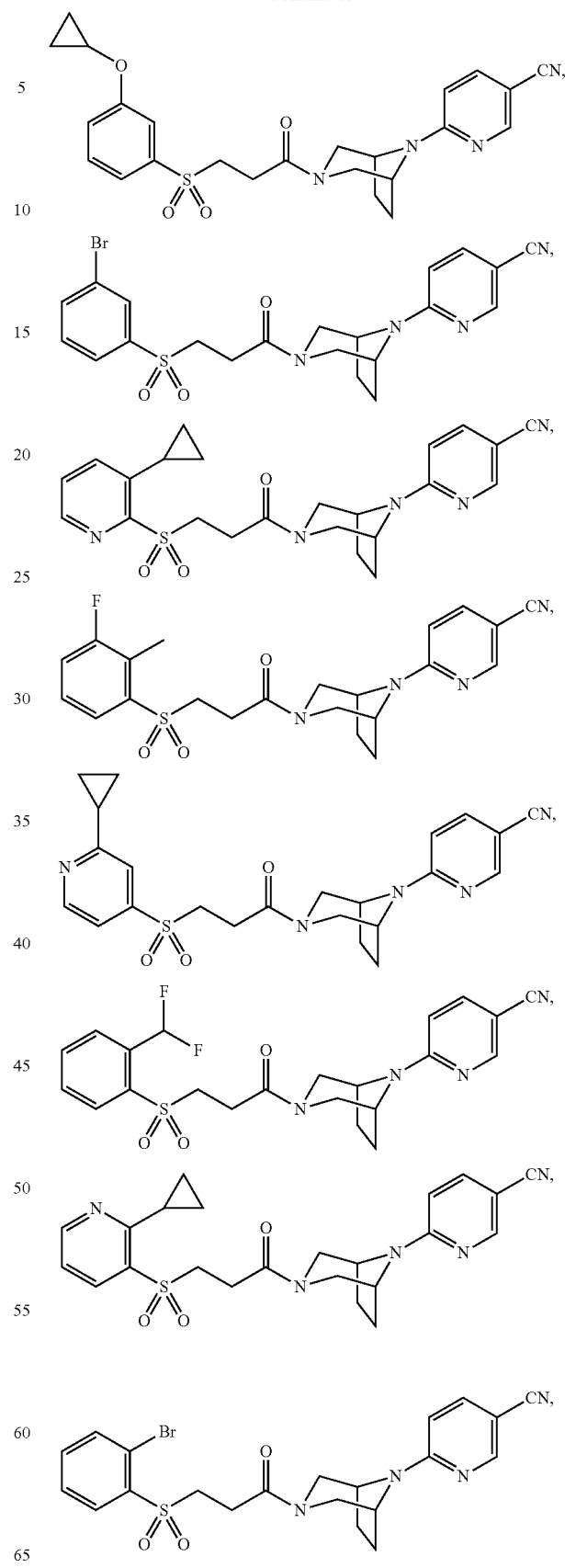

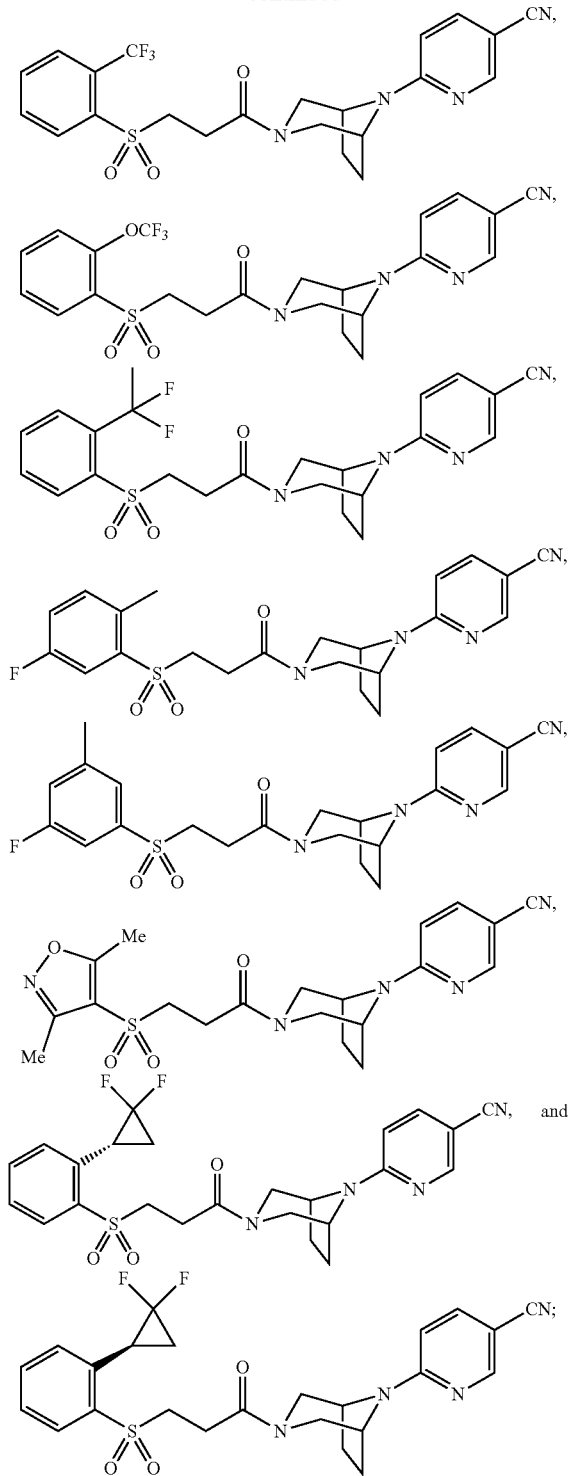

or a pharmaceutically acceptable salt thereof.

Embodiment P20. A pharmaceutical composition comprising a compound of any one of embodiments P1-P19, or a pharmaceutically acceptable salt or solvate thereof, and at least one pharmaceutically acceptable excipient.

Embodiment P21. A method of treating a neurodegenerative disorder in a subject in need thereof, comprising administering to the subject a therapeutically effective amount of a compound of any one of embodiments P1-P19, or a pharmaceutically acceptable salt or solvate thereof.

Embodiment P22. A method of treating a demyelinating disease in a subject in need thereof, comprising administering to the subject a therapeutically effective amount of a compound of any one of embodiments P1-P19, or a pharmaceutically acceptable salt or solvate thereof.

Embodiment P23. The method of embodiment P22, wherein the demyelinating disease is a demyelinating disease of the central nervous system.

Embodiment P24. The method of embodiment P23, wherein the disease is multiple sclerosis.

Embodiment P25. The method of embodiment P22, wherein the demyelinating disease is a demyelinating disease of the peripheral nervous system.

Embodiment P26. A method of treating a neuropathic disease, optionally a peripheral neuropathy, in a subject in need thereof, comprising administering to the subject a therapeutically effective amount of a compound of any one of embodiments P1-P19, or a pharmaceutically acceptable salt or solvate thereof.

Embodiment P27. The method of embodiment P26, wherein the neuropathic disease disease is diabetic neuropathy.

Embodiment P28. The method of any one of embodiments P21-P27, further comprising the administration of one or more immunomodulatory agents.

Embodiment P29. The method of embodiment P28, wherein the one or more immunomodulatory agents are selected from: an IFN-β1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other S1P1 functional modulator; a dimethyl fumarate or other NRF2 functional modulator; an antibody to the alpha subunit of the IL-2 receptor of T cells (CD25) or daclizumab; an antibody against CD52 or alemtuzumab; an antibody against CD20 or ocrelizumab; and an inhibitor of a dihydroorotate dehydrogenase or teriflunomide.

Embodiment P30. A method of modulating muscarinic acetylcholine receptor $M_1$ activity in a subject comprising administering to the subject a compound of any one of embodiments P1-P19, or a pharmaceutically acceptable salt or solvate thereof.

Embodiment P31. The method of embodiment P30, wherein the compound acts as a selective M1 antagonist.

EXAMPLES

The following examples are provided merely as illustrative of various embodiments and shall not be construed to limit the disclosure in any way.

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, WI, including Sigma Chemical and Fluka), Apin Chemicals Ltd. (Milton Park, UK), Ark Pharm, Inc. (Libertyville, IL), Avocado Research (Lancashire, U.K.), BDH Inc. (Toronto, Canada), Bionet (Cornwall, U.K.), Chemservice Inc. (West Chester, PA), Combi-blocks (San Diego, CA), Crescent Chemical Co. (Hauppauge, NY), eMolecules (San Diego, CA), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Matrix Scientific, (Columbia, SC), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Ryan Scientific, Inc. (Mount Pleasant, SC), Spectrum Chemicals (Gardena, CA), Sundia Meditech, (Shanghai, China), TCI America (Portland, OR), Trans World Chemicals, Inc. (Rockville, MD), and WuXi (Shanghai, China).

Suitable reference books and treatises that detail the synthesis of reactants useful in the preparation of compounds described herein, or provide references to articles that describe the preparation, include for example, "Synthetic Organic Chemistry," New York: John Wiley & Sons, Inc., 1982; Sandler S. R. et al., "Organic Functional Group Preparations," $2^{nd}$ ed., New York: Academic Press, 1983; House, H. O., "Modern Synthetic Reactions," $2^{nd}$ ed., Menlo Park: W. A. Benjamin, Inc., 1972; Gilchrist, T. L., "Heterocyclic Chemistry," $2^{nd}$ ed., New York: Wiley, 1992; March, J., "Advanced Organic Chemistry: Reactions, Mechanisms and Structure," $4^{th}$ ed., New York: Wiley, 1992. Additional suitable reference books and treatises that detail the synthesis of reactants useful in the preparation of compounds described herein, or provide references to articles that describe the preparation, include for example, Fuhrhop, J., Penzlin, G., "Organic Synthesis: Concepts, Methods, Starting Materials," $2^{nd}$ ed., New York: Wiley, 1994; Hoffman, R. V., "Organic Chemistry, An Intermediate Text," Oxford: Oxford University Press, 1996; Larock, R. C., "Comprehensive Organic Transformations: A Guide to Functional Group Preparations," $2^{nd}$ ed., New York: Wiley, 1999; Otera, J., "Modern Carbonyl Chemistry," New York: Wiley, 2000; Solomons, T. W. G., "Organic Chemistry," $7^{th}$ ed., New York: Wiley, 2000; Stowell, J. C., "Intermediate Organic Chemistry," $2^{nd}$ ed., New York: Wiley, 1993; "Industrial Organic Chemicals: Starting Materials and Intermediates: An Ullmann's Encyclopedia," New York: Wiley, in 8 volumes; "Organic Reactions," New York: Wiley, in over 55 volumes; and "Chemistry of Functional Groups," New York: Wiley, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is Stahl, P. H., Wermuth, C. G., "Handbook of Pharmaceutical Salts," Zurich: Verlag Helvetica Chimica Acta, 2002.

List of Abbreviations

As used above, and throughout the description of the present disclosure, the following abbreviations, unless otherwise indicated, shall be understood to have the following meanings:

ACN or MeCN acetonitrile
aq aqueous
Bn benzyl
Bu butyl
BOC or Boc tert-butyl carbamate
BrettPhos 2-(dicyclohexylphosphino)-3,6-dimethoxy-2'4'6'-triisopropyl-1,1'-biphenyl
BSA bovine serum albumin
CDI 1,1'-carbonyldiimidazole
CHO Chinese hamster ovary
Cy cyclohexyl
dba dibenzylideneacetone
DAST diethylaminosulfur trifluoride
DCC N,N'-dicyclohexylcarbodiimide
DCE dichloroethane ($C_1CH_2CH_2C_1$)
DCM dichloromethane ($CH_2Cl_2$)
DIPEA or DIEA diisopropylethylamine
DMAP 4-(N,N-dimethylamino)pyridine
DME 1,2-dimethoxyethane
DMF N,N-dimethylformamide
DMA N,N-dimethylacetamide
DMSO dimethylsulfoxide
EDC N-(3-dimethylaminopropyl)-N'-ethylcarbodiimide
equiv equivalent(s)
Et ethyl
EtOH ethanol
EtOAc ethyl acetate
FBS fetal bovine serum
h hour(s)
HATU 1-[bis(dimethylamino)methylene]-1H-1,2,3-triazolo[4,5-b]pyridinium 3-oxide hexafluorophosphate
HOBT Hydroxybenzotriazole
HEPES 4-(2-hydroxyethyl)-1-piperazineethanesulfonic acid
Hex hexanes
HPLC high performance liquid chromatography
LAH lithium aluminum hydride
LCMS or LC-MS liquid chromatography-mass spectrometry
LG leaving group
M molar
mCPBA meta-chloroperoxybenzoic acid
Me methyl
MeOH methanol
min minute(s)
MS mass spectroscopy
NMM N-methylmorpholine
NMP N-methyl-2-pyrrolidone
NMR nuclear magnetic resonance
Oxone Potassium peroxymonosulfate
$Pd_2(dba)_3$ Tris(dibenzylideneacetone)dipalladium(0)
$Pd(PPh_3)_4$ palladium tetrakistriphenyl phosphine
Pd/C palladium on carbon
PG protecting group
PMB para-methoxybenzyl
RT room temperature
sec seconds
T3P propylphosphonic anhydride
TBAF tetrabutylammonium fluoride
TEA triethylamine
TFA trifluoroacetic acid
THF tetrahydrofuran
TLC thin layer chromatography
XantPhos 4,5-bis(diphenylphosphino)-9,9-dimethylxanthene General Synthetic Scheme Compounds of Formula (IA) or (IB) of the present disclosure may be prepared, for example, from a carboxylic acid (2) and amine (1a) or (1b), or its corresponding salt, in the presence of an appropriate coupling reagent such as HATU, EDC, T3P, or the like, and an appropriate base such as TEA, DIEA, or the like (Scheme 1).

Scheme 1

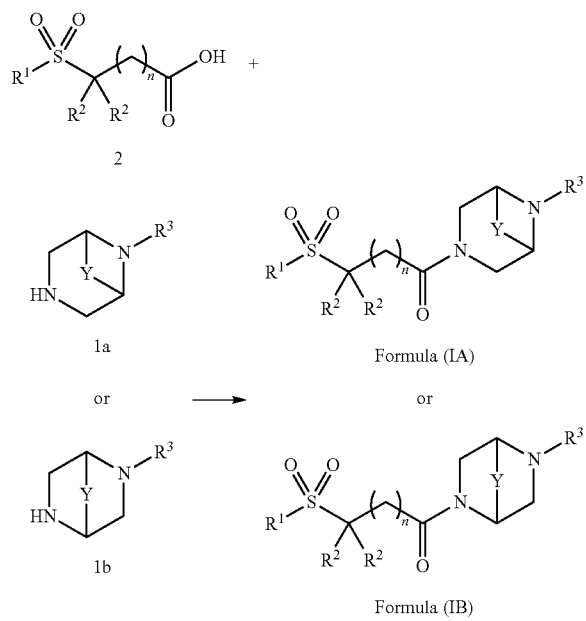

Intermediate Amine: Preparation of 6-(3,8-Diazabicyclo[3.2.1]Octan-8-yl)nicotinonitrile

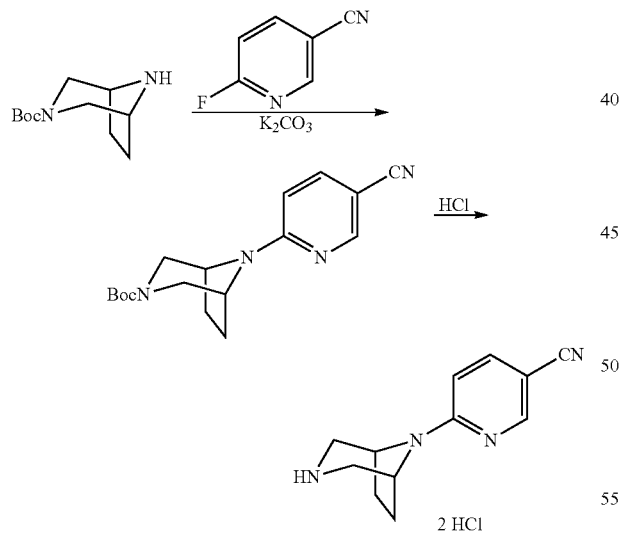

Step 1: In a dried round-bottom flask equipped with a magnetic stirrer and a reflux condenser was dissolved tert-butyl 3,8-diazabicyclo[3.2.1]octane-3-carboxylate (1 equiv) and 5-cyano-2-fluoropyridine (1.2 equiv) in acetonitrile (0.45 M). To this was then added potassium carbonate (2 equiv) in one rapid portion and the resulting suspension was stirred at reflux for 3 h. The reaction suspension was then cooled to RT and filtered. The insoluble was rinsed further with acetonitrile and the filtrate was concentrated in vacuo.

The resulting residue was then partitioned between EtOAc and water. The organic layer was separated and washed further with water (2×) and brine. The combined aqueous washes were backextracted with EtOAc (2×). The EtOAc extracts were then combined, dried over MgSO$_4$, filtered and the filtrate concentrated in vacuo. The resulting oil, which solidified upon standing, was taken up in warm EtOAc and then added an equal volume of hexanes. Upon cooling to RT, slow precipitation of white crystalline solid was observed. This solid impurity was removed via filtration and discarded. The filtrate was then concentrated in vacuo and the crude product thus obtained was purified further by way of column chromatography (SiO$_2$, gradient elution: Hex→1:1 (v/v) Hex: EtOAc) to afford tert-butyl 8-(5-cyanopyridin-2-yl)-3,8-diazabicyclo[3.2.1]octane-3-carboxylate as a white, crystalline solid (94% yield). LCMS: m/z=315.1 [M+H]$^+$.

Step 2: In a dried round-bottom flask equipped with a magnetic stirrer was dissolved tert-butyl 8-(5-cyanopyridin-2-yl)-3,8-diazabicyclo[3.2.1]octane-3-carboxylate (1 equiv) from the previous step in dichloromethane (0.42 M). To this was then added at 0° C. HCl (4 equiv, 4 M solution in dioxane, Sigma-Aldrich) in three portions over a period of 30 min. The resulting suspension was stirred at 0° C. for 1 h and then allowed to warm slowly to RT over 16 h. The reaction mixture was added tert-butyl methyl ether and the resulting thick suspension was vigorously stirred at RT for 1 h. Finally, the suspension was filtered, washed further with tert-butyl methyl ether and air-dried to afford the title compound as a white crystalline solid (96% yield). LCMS: m/z=215.1 [M+H]$^+$.

Example 1: Preparation of 6-(3-(4-((2-iodophenyl)sulfonyl)butanoyl)-3,8-diazabicyclo[3.2.1]octan-8-yl)nicotinonitrile

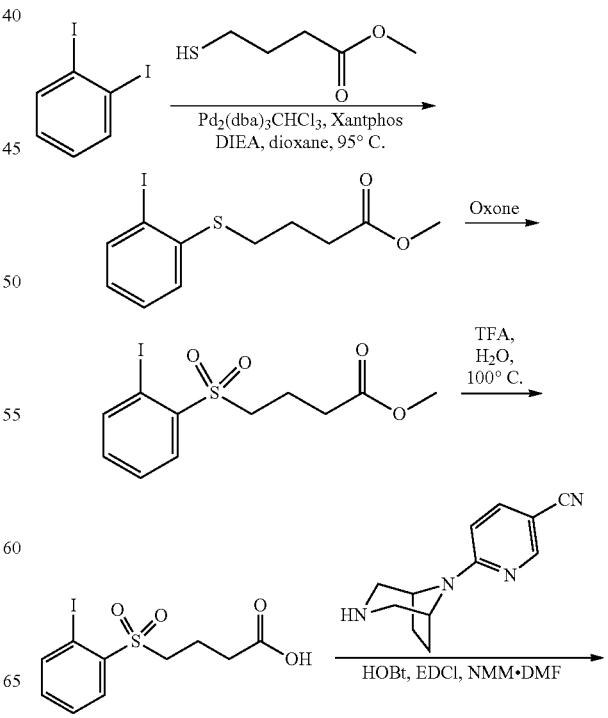

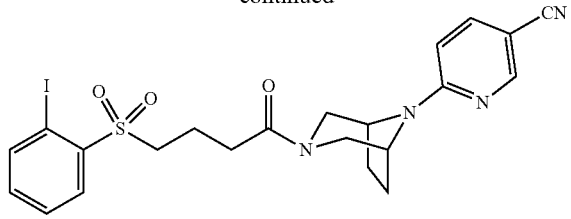

Step 1: In a sealable reaction tube purged and maintained with an inert atmosphere of nitrogen, was combined 1,2-diiodobenzene (2 equiv), methyl 4-sulfanylbutanoate (1 equiv), $Pd_2(dba)_3CHCl_3$ (0.1 equiv), XantPhos (0.2 equiv), and DIEA (2 equiv) in dioxane (0.32 M). The resulting solution was stirred for 12 h at 95° C. in an oil bath. The solids were filtered out and the filtrate was concentrated in vacuo. The resulting residue was applied onto a silica gel column and eluted with 15:85 (v/v) ethyl acetate:petroleum ether. Methyl 4-[(2-iodophenyl)sulfanyl]butanoate thus obtained was isolated as a yellow green oil (86% yield). LCMS: m/z=337 [M+H]$^+$.

Step 2: In a round-bottom flask was combined methyl 4-[(2-iodophenyl)sulfanyl]butanoate (1 equiv) and Oxone (2 equiv) in a 5:2 (v/v) solution of MeOH and $H_2O$ (0.14 M). The resulting solution was stirred for 3 h at 35° C. before it was extracted with dichloromethane. The organic layer was washed with saturated aq. $NaHSO_3$ (2×) and concentrated in vacuo. The resulting residue was applied onto a silica gel column and eluted with 20:80 (v/v) ethyl acetate:petroleum ether. Methyl 4-((2-iodophenyl)sulfonyl)butanoate thus obtained was isolated as as a yellow green oil (42% yield). LCMS: m/z=369 [M+H]$^+$.

Step 3: In a round-bottom flask was combined methyl 4-((2-iodophenyl)sulfonyl)butanoate (1 equiv) and TFA (48 equiv) in $H_2O$ (0.27 M). The resulting solution was stirred for 1.5 h at 100° C. in an oil bath. The resulting mixture was concentrated in vacuo to afford 4-(2-iodobenzenesulfonyl)butanoic acid as a yellow oil (69% yield). LCMS: m/z=355 [M+H]$^+$.

Step 4: In a sealable reaction tube was dissolved 4-(2-iodobenzenesulfonyl)butanoic acid (1.2 equiv), HOBt (1.2 equiv), EDCI (1.2 equiv), NMM (5 equiv), and Intermediate amine (1 equiv) in DMF (0.062 M). The resulting solution was stirred for 1 h at 25° C. The crude product was purified by HPLC to afford the title compound as an off-white solid (43% yield). LCMS: m/z=551.1 [M+H]$^+$. $^1$H NMR (300 MHz, Methanol-$d_4$) δ 8.41 (dd, J=2.3, 0.7 Hz, 1H), 8.20 (dd, J=7.8, 1.1 Hz, 1H), 8.16 (dd, J=7.9, 1.6 Hz, 1H), 7.76 (dd, J=9.0, 2.3 Hz, 1H), 7.65 (td, J=7.9, 1.2 Hz, 1H), 7.37 (td, J=7.7, 1.7 Hz, 1H), 6.84 (dd, J=9.0, 0.6 Hz, 1H), 4.71 (br s, 2H), 4.21 (d, J=12.9 Hz, 1H), 3.62-3.54 (m, 3H), 3.35-3.30 (m, 1H), 2.90 (d, J=13.2 Hz, 1H), 2.72-2.56 (m, 1H), 2.53-2.36 (m, 1H), 2.04-1.94 (m, 4H), 1.83-1.70 (m, 2H).

Example 2: Synthesis of 6-(3-(3-((3-methoxyphenyl)sulfonyl)propanoyl)-3,8-diazabicyclo[3.2.1]octan-8-yl)nicotinonitrile

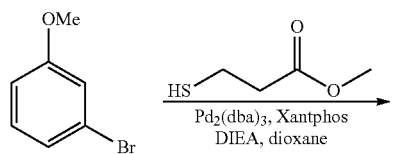

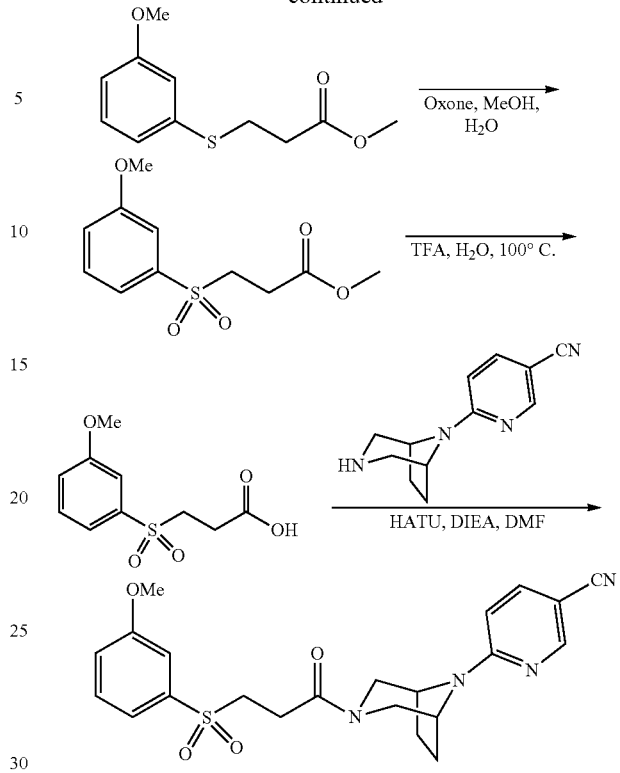

Step 1: In a sealable reaction tube purged and maintained with an inert atmosphere of nitrogen was combined 1-bromo-3-methoxybenzene (1 equiv), methyl 3-mercaptopropionate (1.5 equiv), $Pd_2(dba)_3$ (0.1 equiv), Xantphos (0.2 equiv) and DIEA (2.5 equiv) in dioxane (0.53 M). The resulting solution was stirred for 2 h at 110° C. in an oil bath. The solids were filtered out and the filtrate was concentrated in vacuo. The resulting residue was applied onto a silica gel column and eluted with 15:85 (v/v) ethyl acetate:petroleum ether. Methyl 3-[(3-methoxyphenyl)sulfanyl]propanoate thus obtained was isolated as a yellow oil. LCMS: m/z=227.1 [M+H]$^+$.

Step 2: In a round-bottom flask was combined methyl 3-[(3-methoxyphenyl)sulfanyl]propanoate (1 equiv) and Oxone (2 equiv) in a 5:2 (v/v) solution of MeOH and $H_2O$ (0.13 M). The resulting solution was stirred for 2 h at room temperature and extracted with ethyl acetate. The combined organic extracts were concentrated in vacuo and the resulting residue was applied onto a silica gel column. Elution with 20:80 (v/v) ethyl acetate: petroleum ether afforded methyl 3-(3-methoxybenzenesulfonyl)propanoate as a light yellow oil (58% yield). LCMS: m/z=259.1 [M+H]$^+$.

Step 3: In a round-bottom flask was combined methyl 3-(3-methoxybenzenesulfonyl)propanoate (1 equiv) and TFA (56 equiv) in $H_2O$ (0.23 M). The resulting solution was stirred for 2 h at 100° C. in an oil bath. The resulting mixture was concentrated in vacuo and purified by Flash-Prep-HPLC. 3-(3-Methoxybenzenesulfonyl)propanoic acid thus obtained was isolated as a yellow oil (56% yield). LCMS: m/z=245.1 [M+H]$^+$.

Step 4: In a round-bottom flask was combined 3-(3-methoxybenzenesulfonyl)propanoic acid (1 equiv), HATU (1.5 equiv), DIEA (3 equiv) and Intermediate amine (1.2 equiv) in DMF (0.053 M). The resulting solution was stirred for 1 h at room temperature. The crude product was purified by HPLC to afford the title compound as a white solid (41% yield). LCMS: m/z=441.1 [M+H]+. 1H NMR (300 MHz, Methanol-d4) δ 8.44 (dd, J=2.1, 0.6 Hz, 1H), 7.77 (dd, J=9.0, 2.3 Hz, 1H), 7.58-7.49 (m, 2H), 7.45 (t, J=2.1 Hz, 1H), 7.30-7.26 (m, 1H), 6.86 (d, J=9.0 Hz, 1H), 4.77 (br s, 1H), 4.71 (br s, 1H), 4.15 (d, J=7.7 Hz, 1H), 3.89 (s, 3H), 3.73 (d, J=7.7 Hz, 1H), 3.69-3.53 (m, 2H), 3.40-3.32 (m, 1H), 2.92-2.86 (m, 2H), 2.78-2.73 (m, 1H), 2.05-1.75 (m, 4H).

Example 3: Synthesis of 6-(3-(3-((4-fluoro-3-methoxyphenyl)sulfonyl)propanoyl)-3,8-diazabicyclo[3.2.1]octan-8-yl)nicotinonitrile

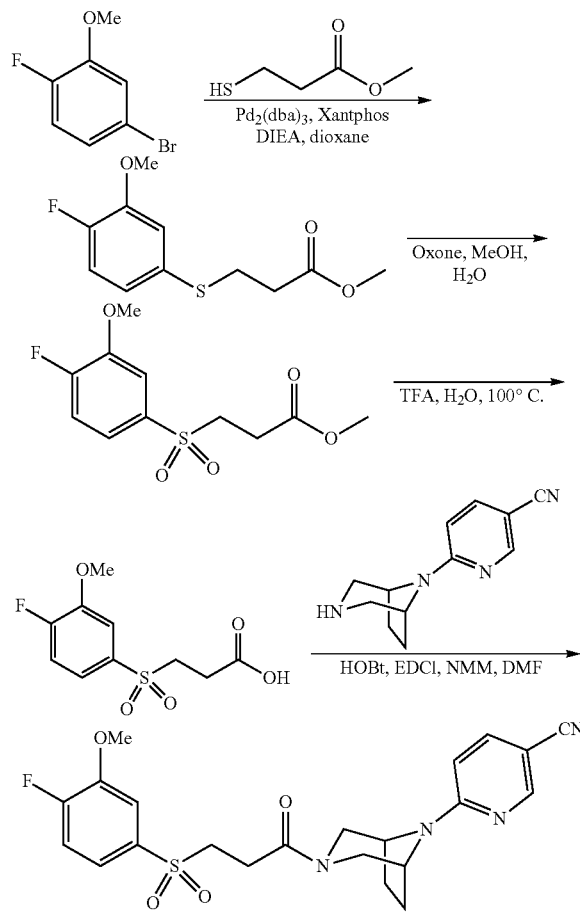

Step 1: In a 3-necked round-bottom flask purged and maintained with an inert atmosphere of nitrogen was combined 4-bromo-1-fluoro-2-methoxybenzene (1 equiv), methyl 3-mercaptopropionate (2 equiv), Pd2(dba)3 (0.1 equiv), Xantphos (0.2 equiv), and DIEA (2 equiv) in dioxane (0.65 M). The resulting solution was stirred for 2 h at 110° C. The solids were filtered out and the filtrate was concentrated in vacuo. The resulting residue was applied onto a silica gel column and eluted with 20:80 (v/v) ethyl acetate: petroleum ether. Methyl 3-[(4-fluoro-3-methoxyphenyl)sulfanyl]propanoate thus obtained was isolated as a yellow oil (92% yield). LCMS: m/z=245 [M+H]+.

Step 2: In a round-bottom flask was dissolved methyl 3-[(4-fluoro-3-methoxyphenyl)sulfanyl]propanoate (1 equiv) in MeOH (0.082 M). To this solution was then added an aqueous solution (0.32 M) of Oxone (2 equiv) dropwise at 0° C. over a period of 5 min. The resulting solution was stirred for 1 h at 25° C. and extracted with ethyl acetate. The combined organic extracts were washed sequentially with water (1x), saturated aqueous NaHSO3 (2×) and brine. After removal of the volatiles in vacuo, the resulting residue was applied onto a silica gel column and eluted with 42:58 (v/v) ethyl acetate:petroleum ether. Methyl 3-(4-fluoro-3-methoxybenzenesulfonyl)propanoate thus obtained was isolated as a yellow solid (88% yield). LCMS: m/z=277 [M+H]+.

Step 3: In a round-bottom flask was combined methyl 3-(4-fluoro-3-methoxybenzenesulfonyl)propanoate (1 equiv) and TFA (25 equiv) in H2O (0.52 M). The resulting solution was stirred for 2.5 h at 100° C. The resulting mixture was concentrated in vacuo to afford 3-(4-fluoro-3-methoxybenzenesulfonyl)propanoic acid as a yellow solid (>99% yield). LCMS: m/z=263 [M+H]+.

Step 4: In a reaction vial was combined 3-(4-fluoro-3-methoxybenzenesulfonyl)propanoic acid (1 equiv), HOBt (1.2 equiv), EDCI (1.2 equiv), NMM (3 equiv) and Intermediate amine (1.2 equiv) in DMF (0.092 M). The resulting solution was stirred for 45 min at 25° C. The crude product was purified by HPLC to afford the title compound as a white solid (44% yield). LCMS: m/z=459.1 [M+H]t 1H NMR (300 MHz, DMSO-d6) δ 8.51 (d, J=1.8 Hz, 1H), 7.89 (dd, J=8.9, 2.3 Hz, 1H), 7.61 (d, J=8.4 Hz, 1H), 7.51-7.48 (m, 2H), 6.92 (d, J=9.0 Hz, 1H), 4.69 (br s, 2H), 4.00 (d, J=11.7 Hz, 1H), 3.93 (s, 3H), 3.64-3.52 (m, 3H), 3.21 (d, J=9.3 Hz, 2H), 2.83-2.70 (m, 2H), 1.89-1.80 (m, 3H), 1.55 (br s, 1H).

Example 4: Synthesis of 6-(3-(3-((2-cyclopropyl-3-fluorophenyl)sulfonyl)-propanoyl)-3,8-diazabicyclo[3.2.1]octan-8-yl)nicotinonitrile

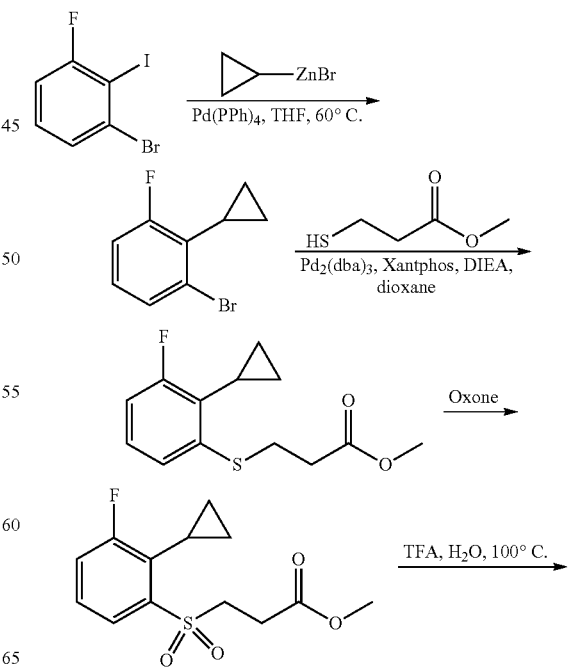

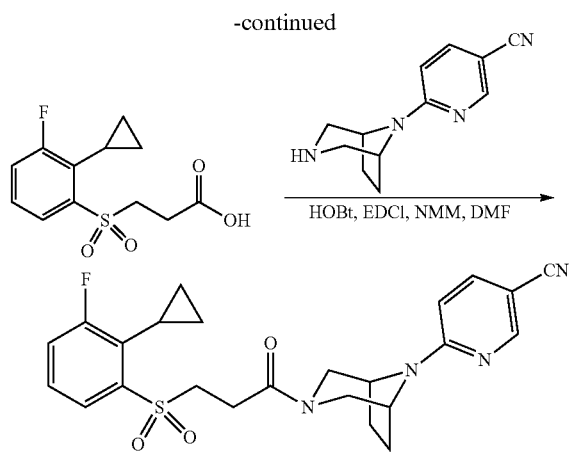

Step 1: In a sealable reaction tube purged and maintained with an inert atmosphere of nitrogen was combined 1-bromo-3-fluoro-2-iodobenzene (1 equiv), bromo(cyclopropyl)zinc (2 equiv), and Pd(PPh$_3$)$_4$ (0.05 equiv) in THF (0.33 M). The resulting solution was stirred for 16 h at 60° C. in an oil bath before it was extracted with ethyl acetate. The combined organic extracts were concentrated in vacuo and the resulting residue was applied onto a silica gel column. Elution with 20:80 (v/v) ethyl acetate:petroleum ether afforded 1-bromo-2-cyclopropyl-3-fluorobenzene as light yellow oil (42% yield). LCMS: m/z=215.1 [M+H]$^+$.

Step 2: In a sealable reaction tube purged and maintained with an inert atmosphere of nitrogen was combined 1-bromo-2-cyclopropyl-3-fluorobenzene (1 equiv), methyl 3-mercaptopropionate (1.2 equiv), Pd$_2$(dba)$_3$ (0.1 equiv), Xantphos (0.2 equiv), and DIEA (3 equiv) in dioxane (0.28 M). The resulting solution was stirred for 2 h at 110° C. in an oil bath. The solids were filtered out and the filtrate was concentrated in vacuo. The resulting residue was applied onto a silica gel column and eluted with 15:85 (v/v) ethyl acetate:petroleum ether. Methyl 3-[(2-cyclopropyl-3-fluorophenyl)sulfanyl]propanoate thus obtained was isolated as a colorless oil (31% yield). LCMS: m/z=255.1 [M+H]$^+$.

Step 3: In a round-bottom flask was combined methyl 3-[(2-cyclopropyl-3-fluorophenyl)sulfanyl]propanoate (1 equiv) and Oxone (2 equiv) in a 1:1 (v/v) solution of MeOH and H$_2$O (0.072 M). The resulting solution was stirred for 1 h at 25° C. and extracted with dichloromethane. The combined organic extracts were concentrated in vacuo and the resulting residue was applied onto a silica gel column. Elution with 20:80 (v/v) ethyl acetate:petroleum ether afforded methyl 3-(2-cyclopropyl-3-fluorobenzenesulfonyl)propanoate as a yellow oil (65% yield). LCMS: m/z=287.1 [M+H]$^+$.

Step 4: In a round-bottom flask was combined methyl 3-(2-cyclopropyl-3-fluorobenzenesulfonyl)propanoate (1 equiv) and TFA (93 equiv) in H$_2$O (0.14 M). The resulting solution was stirred for 2 h at 100° C. in an oil bath. The resulting mixture was concentrated in vacuo and purified by Flash-Prep-HPLC. 3-(2-Cyclopropyl-3-fluorobenzenesulfonyl)propanoic acid thus obtained was isolated as a yellow oil. LCMS: m/z=273.1 [M+H]$^+$.

Step 5: In a round-bottom flask was combined 3-(2-cyclopropyl-3-fluorobenzenesulfonyl)propanoic acid (1 equiv), HOBt (1.2 equiv), EDCI (1.2 equiv), NMM (3 equiv), and Intermediate amine (1.1 equiv) in DMF (0.060M). The resulting solution was stirred for 1 h at 25° C. The crude product was purified by HPLC to afford the title compound as a white solid (39% yield). LCMS: m/z=469.1 [M+H]$^+$. 1H NMR (300 MHz, DMSO-d$_6$) δ 8.52 (d, J=2.0 Hz, 1H), 7.89 (dd, J=9.0, 2.3 Hz, 1H), 7.79-7.76 (m, 1H), 7.50-7.42 (m, 2H), 6.92 (d, J=9.0 Hz, 1H), 4.69 (br s, 2H), 4.00 (d, J=9.0 Hz, 1H), 3.76-3.69 (m, 2H), 3.62 (d, J=8.6 Hz, 1H), 3.23 (d, J=7.4 Hz, 1H), 2.92-2.86 (m, 1H), 2.71 (d, J=9.0 Hz, 1H), 2.62-2.50 (m, 1H), 2.48-2.41 (m, 1H), 1.88-1.81 (m, 3H), 1.56 (br s, 1H), 1.21-1.18 (m, 2H), 1.10-1.06 (m, 2H).

Example 5: Synthesis of 6-(3-(3-((2-(2,2-difluorocyclopropyl)phenyl)-sulfonyl)-propanoyl)-3,8-diazabicyclo[3.2.1]octan-8-yl)nicotinonitrile

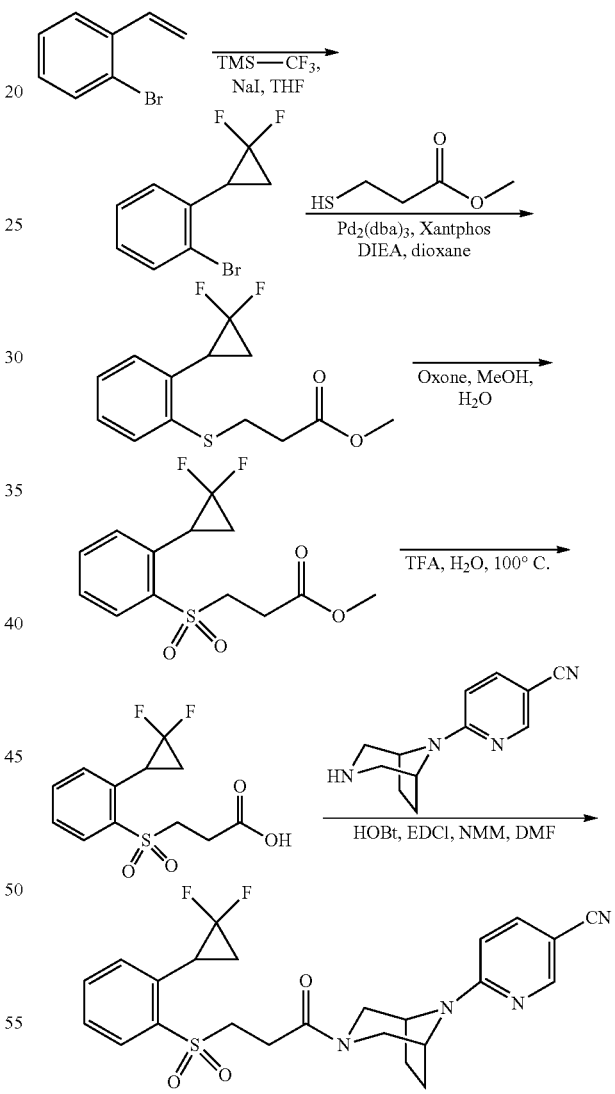

Step 1: In a sealable reaction tube purged and maintained with an inert atmosphere of nitrogen was combined 2-bromostyrene (1 equiv), trifluoromethyltrimethylsilane (4 equiv), and NaI (0.2 equiv) in THF (0.46 M). The resulting solution was stirred for 3 h at 65° C. in an oil bath and then extracted with ethyl acetate. The combined organic extracts were concentrated in vacuo and the resulting residue was applied onto a silica gel column. Elution with 20:80 (v/v)

ethyl acetate:petroleum ether afforded 1-bromo-2-(2,2-difluorocyclopropyl)benzene as a yellow oil (56% yield). GCMS: m/z=232.1 [M+H]$^+$.

Step 2: In a sealable reaction tube purged and maintained with an inert atmosphere of nitrogen was combined 1-bromo-2-(2,2-difluorocyclopropyl)benzene (1 equiv), methyl 3-mercaptopropionate (1.2 equiv), Pd$_2$(dba)$_3$ (0.1 equiv), Xantphos (0.2 equiv), and DIEA (2 equiv) in dioxane (0.26 M). The resulting solution was stirred for 2 h at 110° C. in an oil bath. The solids were filtered out and the filtrate was concentrated in vacuo. The resulting residue was applied onto a silica gel column and eluted with 15:85 (v/v) ethyl acetate:petroleum ether. Methyl 3-[[2-(2,2-difluorocyclopropyl)phenyl]sulfanyl]propanoate thus obtained was isolated as a yellow oil (65% yield). LCMS: m/z=273.1 [M+H]$^+$.

Step 3: In a round-bottom flask was combined methyl 3-[[2-(2,2-difluorocyclopropyl)-phenyl]sulfanyl]propanoate (1 equiv) and Oxone (2 equiv) in a 1:1 (v/v) solution of MeOH and H$_2$O (0.11 M). The resulting solution was stirred for 2 h at 25° C. and extracted with ethyl acetate. The combined organic extracts were concentrated in vacuo and the resulting residue was purified by Flash-Prep-HPLC to afford methyl 3-((2-(2,2-difluorocyclopropyl)phenyl)sulfonyl)propanoate as a yellow oil. LCMS: m/z=305.1 [M+H]$^+$.

Step 4: In a round-bottom flask was combined methyl 3-((2-(2,2-difluoro-cyclopropyl)phenyl)sulfonyl)propanoate (1 equiv) and TFA (57 equiv) in H$_2$O (0.23 M). The resulting solution was stirred for 1 h at 100° C. in an oil bath. The resulting mixture was concentrated in vacuo to afford 3-[2-(2,2-difluorocyclopropyl)benzenesulfonyl]propanoic acid as a light yellow solid (89% yield). LCMS: m/z=291.1 [M+H]$^+$.

Step 5: In a reaction vial was placed 3-[2-(2,2-difluorocyclopropyl)benzenesulfonyl]propanoic acid (1 equiv), HOBt (1.2 equiv), EDCI (1.2 equiv), NMM (5 equiv), and Intermediate amine (1 equiv) in DMF (0.10 M). The resulting solution was stirred for 1 h at room temperature. The crude product was purified by HPLC to afford the title compound as a white solid (40% yield). LCMS: m/z=487.1 [M+H]$^+$. $^1$H NMR (300 MHz, DMSO-d$_6$) δ 8.49 (t, J=2.5 Hz, 1H), 7.98-7.95 (m, 1H), 7.90-7.86 (m, 1H), 7.73-7.71 (m, 1H), 7.58-7.50 (m, 2H), 6.89 (d, J=9.0 Hz, 1H), 4.68 (s, 2H), 3.97 (d, J=8.2 Hz, 1H), 3.64-3.51 (m, 4H), 3.21 (d, J=7.4 Hz, 1H), 2.95-2.75 (m, 1H), 2.74-2.53 (m, 2H), 2.30-2.18 (m, 1H), 2.14-1.95 (m, 1H), 1.99-1.76 (m, 3H), 1.61-1.46 (m, 1H).

Example 6: Synthesis of 6-(3-(3-((4-fluoro-3-(2-hydroxypropan-2-yl)phenyl)-sulfonyl)propanoyl)-3,8-diazabicyclo[3.2.1]octan-8-yl)nicotinonitrile

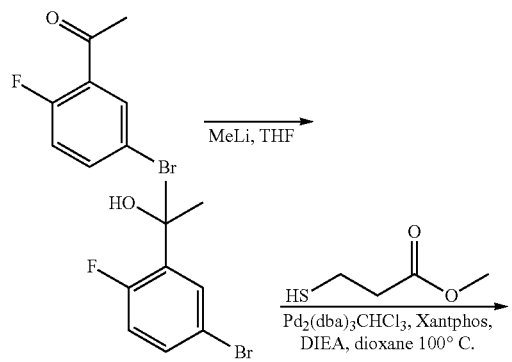

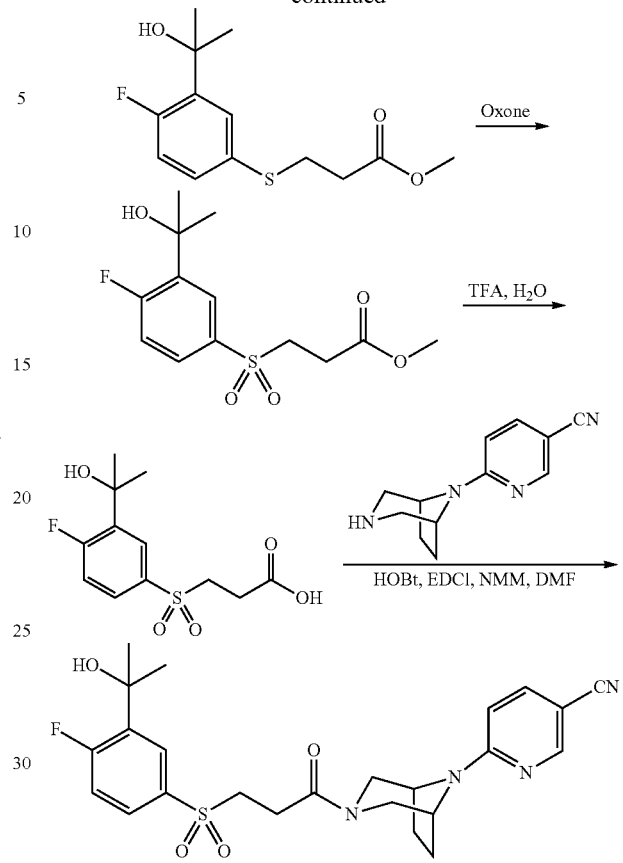

Step 1: In a round-bottom flask was dissolved 1-(5-bromo-2-fluorophenyl)ethanone (1 equiv) in THF (0.58 M). To this solution was then added MeLi (2 equiv, 1.6 M solution in diethyl ether) dropwise over 5 min at −78° C. The resulting mixture was stirred for 1 h at −78° C. followed by 1 h at 0° C. under a nitrogen atmosphere. The reaction was quenched with water at 0° C. and extracted with ethyl acetate. The combined organic layers were washed with water, dried over anhydrous Na$_2$SO$_4$, filtered and the filtrate concentrated in vacuo. The resulting residue was applied onto a silica gel column and eluted with 15:85 (v/v) ethyl acetate:petroleum ether. 2-(5-Bromo-2-fluorophenyl)propan-2-ol thus obtained was isolated as a yellow oil (65% yield). LCMS: m/z=233.2 [M+H]$^+$.

Step 2: In a sealable reaction vial purged and maintained with an inert atmosphere of nitrogen was combined 2-(5-bromo-2-fluorophenyl)propan-2-ol (1 equiv), methyl 3-mercaptopropionate (2 equiv), Pd$_2$(dba)$_3$CHCl$_3$ (0.1 equiv), Xantphos (0.2 equiv), and DIEA (2 equiv) in dioxane (0.38 M). The resulting solution was stirred for 2 h at 100° C. The solids were filtered out and the filtrate was concentrated in vacuo. The resulting residue was applied onto a silica gel column and eluted with 24:76 (v/v) ethyl acetate:petroleum ether to provide methyl 3-[[4-fluoro-3-(2-hydroxypropan-2-yl)phenyl]sulfanyl]propanoate as a yellow oil (97% yield). LCMS: m/z=273 [M+H]$^+$.

Step 3: In a round-bottom flask was dissolved methyl 3-[[4-fluoro-3-(2-hydroxypropan-2-yl)phenyl]sulfanyl]propanoate(1 equiv) in MeOH (0.37 M). To this solution was then added an aqueous solution (0.73 M) of Oxone (2 equiv) dropwise at 0° C. over a period of 5 min. The resulting mixture was stirred for 4 h at 25° C. and then extracted with CH₂Cl₂. The combined organic layers were washed with water, dried over anhydrous Na₂SO₄, filtered and the filtrate concentrated in vacuo. The resulting residue was applied onto a silica gel column and eluted with 43:57 (v/v) ethyl acetate:petroleum ether to provide methyl 3-[4-fluoro-3-(2-hydroxypropan-2-yl)benzenesulfonyl]propanoate as a yellow oil (83% yield). LCMS: m/z=305 [M+H]⁺.

Step 4: In a round-bottom flask was combined methyl 3-[4-fluoro-3-(2-hydroxypropan-2-yl)benzenesulfonyl]propanoate (1 equiv) and TFA (53 equiv) in H₂O (0.25 M). The resulting solution was stirred for 1.5 h at 100° C. The resulting mixture was concentrated in vacuo. to afford 3-[4-fluoro-3-(2-hydroxypropan-2-yl)benzenesulfonyl]propanoic acid as a yellow oil (69% yield). LCMS: m/z=291 [M+H]⁺.

Step 5: Into a reaction vial was combined 3-[4-fluoro-3-(2-hydroxypropan-2-yl)benzenesulfonyl]propanoic acid (1 equiv), HOBt (1.2 equiv), EDCI (1.2 equiv), NMM (5 equiv), and Intermediate amine (1 equiv) in DMF (0.56 M). The mixture was stirred for 45 min at 25° C. The crude product was purified by HPLC to afford the title compound as a white solid (36% yield). LCMS: m/z=487.3 [M+H]⁺. ¹H NMR (300 MHz, Methanol-d₄) δ 8.44 (dd, J=2.3, 0.6 Hz, 1H), 8.26 (dd, J=7.4, 2.5 Hz, 1H), 7.91-7.86 (m, 1H), 7.77 (dd, J=9.0, 2.3 Hz, 1H), 7.32 (dd, J=11.3, 8.5 Hz, 1H), 6.87 (dd, J=8.5, 0.6 Hz, 1H), 4.79 (br s, 1H), 4.71 (br s, 1H), 4.17 (d, J=13.1 Hz, 1H), 3.72 (d, J=12.3 Hz, 1H), 3.60-3.53 (m, 2H), 3.40 (d, J=12.6 Hz, 1H), 2.93-2.88 (m, 2H), 2.77-2.68 (m, 1H), 2.06-1.77 (m, 4H), 1.61 (d, J=3.7 Hz, 6H).

The following examples were prepared by similar procedures as described in Examples 1 to 6.

| Example | Structure | Name | [M + H]+ |
|---|---|---|---|
| 7 | 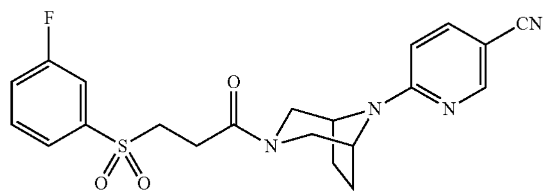 [SMILES: N#Cc1ccc(N2C3CCC2CN(C(=O)CCS(=O)(=O)c2cccc(F)c2)C3)nc1] | 6-{3-[3-(3-fluorobenzenesulfonyl)propanoyl]-3,8-diazabicyclo[3.2.1]octan-8-yl}pyridine-3-carbonitrile | 429.1 |
| 8 | 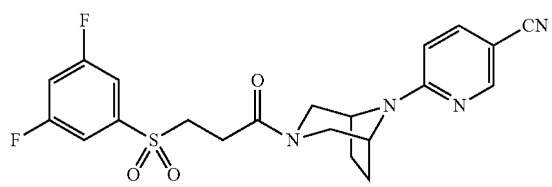 [SMILES: N#Cc1ccc(N2C3CCC2CN(C(=O)CCS(=O)(=O)c2cc(F)cc(F)c2)C3)nc1] | 6-{3-[3-(3,5-difluorobenzenesulfonyl)propanoyl]-3,8-diazabicyclo[3.2.1]octan-8-yl}pyridine-3-carbonitrile | 447.1 |
| 9 | 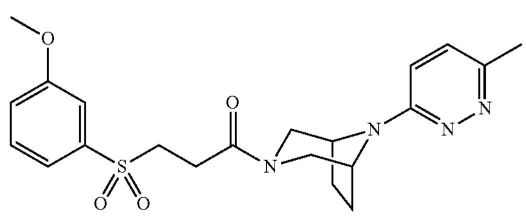 | 3-(3-methoxybenzenesulfonyl)-1-[8-(6-methylpyridazin-3-yl)-3,8-diazabicyclo[3.2.1]octan-3-yl]propan-1-one | 431.1 |
| 10 | 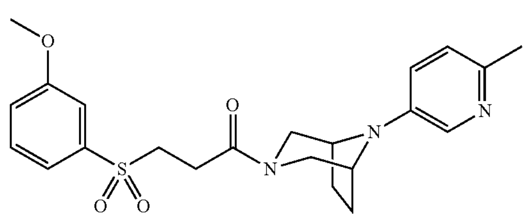 [SMILES: COc1cccc(S(=O)(=O)CCC(=O)N2CC3CCC(C2)N3c2ccc(C)nc2)c1] | 3-(3-methoxybenzenesulfonyl)-1-[8-(6-methylpyridin-3-yl)-3,8-diazabicyclo[3.2.1]octan-3-yl]propan-1-one | 430.1 |
| 11 | 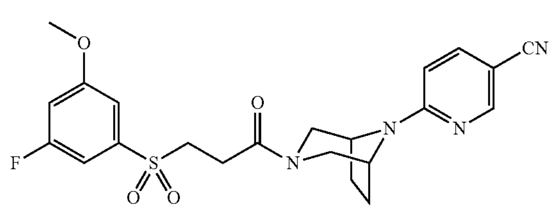 [SMILES: COc1cc(F)cc(S(=O)(=O)CCC(=O)N2CC3CCC(C2)N3c2ccc(C#N)cn2)c1] | 6-{3-[3-(3-fluoro-5-methoxybenzenesulfonyl)propanoyl]-3,8-diazabicyclo[3.2.1]octan-8-yl}pyridine-3-carbonitrile | 459.1 |

| Example | Structure | Name | [M + H]+ |
|---|---|---|---|
| 12 | 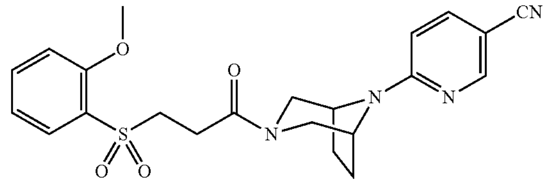 [SMILES: COc1ccccc1S(=O)(=O)CCC(=O)N1CC2CCC(C1)N2c1ccc(C#N)cn1] | 6-{3-[3-(2-methoxybenzenesulfonyl)propanoyl]-3,8-diazabicyclo[3.2.1]octan-8-yl}pyridine-3-carbonitrile | 441.2 |
| 13 | 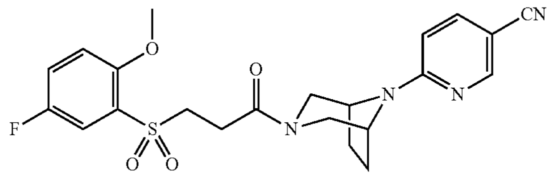 [SMILES: COc1ccc(F)cc1S(=O)(=O)CCC(=O)N1CC2CCC(C1)N2c1ccc(C#N)cn1] | 6-{3-[3-(5-fluoro-2-methoxybenzenesulfonyl)propanoyl]-3,8-diazabicyclo[3.2.1]octan-8-yl}pyridine-3-carbonitrile | 459.1 |
| 14 | 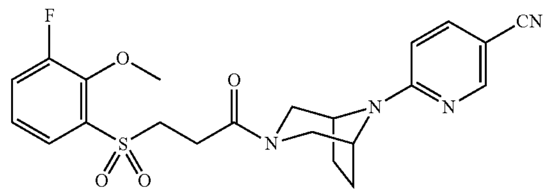 [SMILES: COc1c(F)cccc1S(=O)(=O)CCC(=O)N1CC2CCC(C1)N2c1ccc(C#N)cn1] | 6-{3-[3-(3-fluoro-2-methoxybenzenesulfonyl)propanoyl]-3,8-diazabicyclo[3.2.1]octan-8-yl}pyridine-3-carbonitrile | 459.1 |
| 15 | 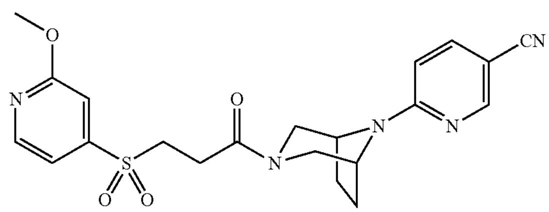 [SMILES: COc1cc(S(=O)(=O)CCC(=O)N2CC3CCC(C2)N3c2ccc(C#N)cn2)ccn1] | 6-(3-{3-[(2-methoxypyridin-4-yl)sulfonyl]propanoyl}-3,8-diazabicyclo[3.2.1]octan-8-yl)pyridine-3-carbonitrile | 442.1 |
| 16 | 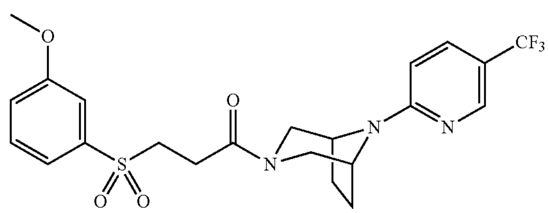 [SMILES: COc1cccc(S(=O)(=O)CCC(=O)N2CC3CCC(C2)N3c2ccc(C(F)(F)F)cn2)c1] | 3-(3-methoxybenzenesulfonyl)-1-{8-[5-(trifluoromethyl)pyridin-2-yl]-3,8-diazabicyclo[3.2.1]octan-3-yl}propan-1-one | 484.1 |
| 17 | 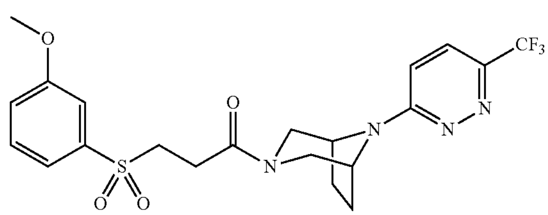 [SMILES: COc1cccc(S(=O)(=O)CCC(=O)N2CC3CCC(C2)N3c2ccc(C(F)(F)F)nn2)c1] | 3-(3-methoxybenzenesulfonyl)-1-{8-[6-(trifluoromethyl)pyridazin-3-yl]-3,8-diazabicyclo[3.2.1]octan-3-yl}propan-1-one | 485.1 |
| 18 | 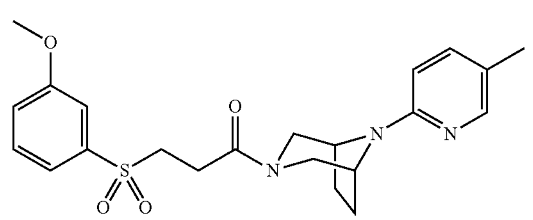 [SMILES: COc1cccc(S(=O)(=O)CCC(=O)N2CC3CCC(C2)N3c2ccc(C)cn2)c1] | 3-(3-methoxybenzenesulfonyl)-1-[8-(5-methylpyridin-2-yl)-3,8-diazabicyclo[3.2.1]octan-3-yl]propan-1-one | 430.1 |

-continued

| Example | Structure | Name | [M + H]+ |
|---|---|---|---|
| 19 | 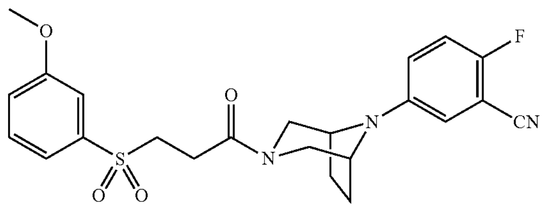 [SMILES: COc1cccc(S(=O)(=O)CCC(=O)N2CC3CCC(C2)N3c2ccc(F)c(C#N)c2)c1] | 2-fluoro-5-{3-[3-(3-methoxybenzenesulfonyl)propanoyl]-3,8-diazabicyclo[3.2.1]octan-8-yl}benzonitrile | 458.1 |
| 20 | 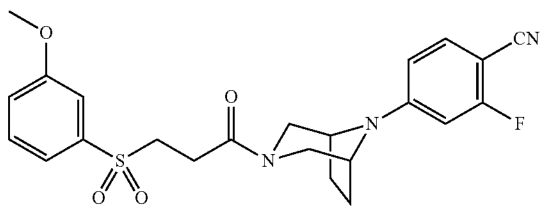 [SMILES: COc1cccc(S(=O)(=O)CCC(=O)N2CC3CCC(C2)N3c2ccc(C#N)c(F)c2)c1] | 2-fluoro-4-{3-[3-(3-methoxybenzenesulfonyl)propanoyl]-3,8-diazabicyclo[3.2.1]octan-8-yl}benzonitrile | 458.1 |
| 21 | 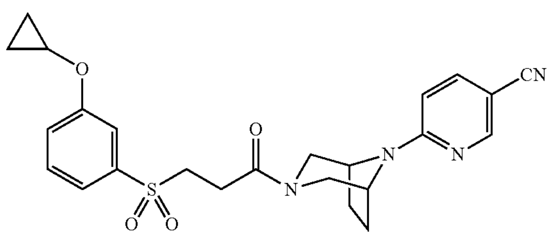 [SMILES: N#Cc1ccc(N2C3CCC2CN(C(=O)CCS(=O)(=O)c2cccc(OC4CC4)c2)C3)nc1] | 6-{3-[3-(3-cyclopropoxybenzenesulfonyl)propanoyl]-3,8-diazabicyclo[3.2.1]octan-8-yl}pyridine-3-carbonitrile | 467.2 |
| 22 | 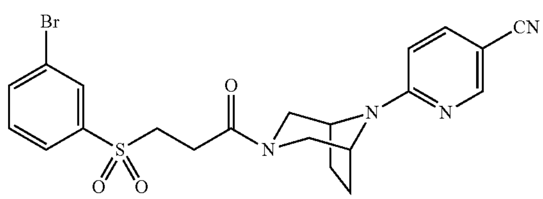 [SMILES: N#Cc1ccc(N2C3CCC2CN(C(=O)CCS(=O)(=O)c2cccc(Br)c2)C3)nc1] | 6-{3-[3-(3-bromobenzenesulfonyl)propanoyl]-3,8-diazabicyclo[3.2.1]octan-8-yl}pyridine-3-carbonitrile | 489.0, 491.0 |
| 23 | 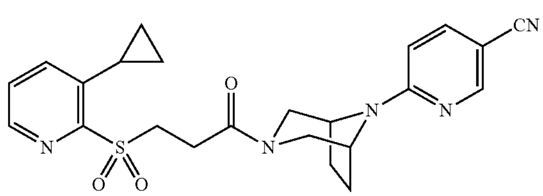 [SMILES: N#Cc1ccc(N2C3CCC2CN(C(=O)CCS(=O)(=O)c2ncccc2C2CC2)C3)nc1] | 6-(3-{3-[(3-cyclopropylpyridin-2-yl)sulfonyl]propanoyl}-3,8-diazabicyclo[3.2.1]octan-8-yl)pyridine-3-carbonitrile | 452.1 |
| 24 | 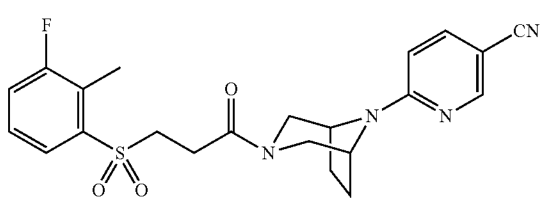 [SMILES: Cc1c(F)cccc1S(=O)(=O)CCC(=O)N1CC2CCC(C1)N2c1ccc(C#N)cn1] | 6-{3-[3-(3-fluoro-2-methylbenzenesulfonyl)propanoyl]-3,8-diazabicyclo[3.2.1]octan-8-yl}pyridine-3-carbonitrile | 443.1 |
| 25 | 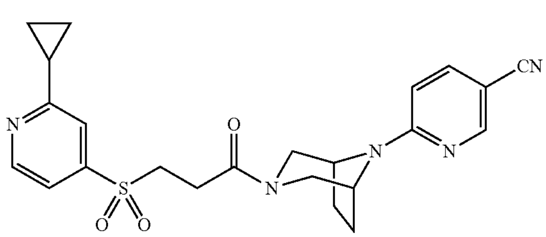 [SMILES: N#Cc1ccc(N2C3CCC2CN(C(=O)CCS(=O)(=O)c2ccnc(C4CC4)c2)C3)nc1] | 6-(3-{3-[(2-cyclopropyl-pyridin-4-yl)sulfonyl]propanoyl}-3,8-diazabicyclo[3.2.1]octan-8-yl)pyridine-3-carbonitrile | 452.2 |

-continued

| Example | Structure | Name | [M + H]+ |
|---|---|---|---|
| 26 | 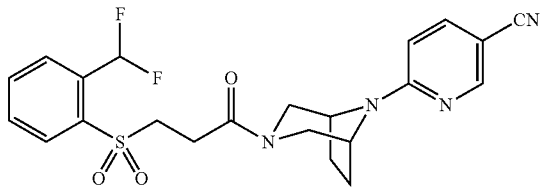 [SMILES: N#Cc1ccc(N2C3CCC2CN(C(=O)CCS(=O)(=O)c2ccccc2C(F)F)C3)nc1] | 6-(3-{3-[2-(difluoromethyl)benzene-sulfonyl]propanoyl}-3,8-diazabicyclo-[3.2.1]octan-8-yl)pyridine-3-carbonitrile | 461.1 |
| 27 | 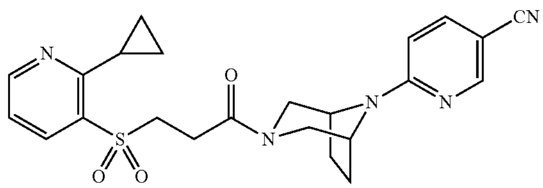 [SMILES: N#Cc1ccc(N2C3CCC2CN(C(=O)CCS(=O)(=O)c2cccnc2C2CC2)C3)nc1] | 6-(3-{3-[(2-cyclopropylpyridin-3-yl)sulfonyl]propanoyl}-3,8-diazabicyclo[3.2.1]octan-8-yl)pyridine-3-carbonitrile | 452.1 |
| 28 | 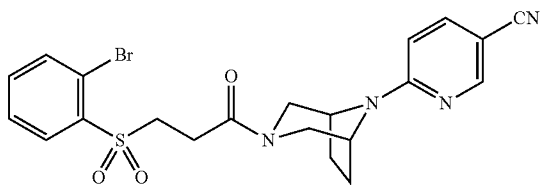 [SMILES: N#Cc1ccc(N2C3CCC2CN(C(=O)CCS(=O)(=O)c2ccccc2Br)C3)nc1] | 6-(3-(3-((2-bromophenyl)sulfonyl)propanoyl)-3,8-diazabicyclo[3.2.1]octan-8-yl)nicotinonitrile | 489.0, 491.0 |
| 29 | 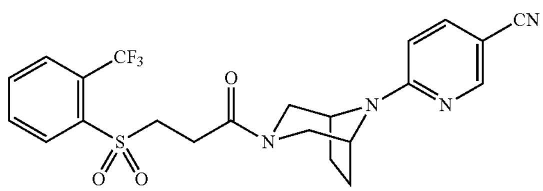 [SMILES: N#Cc1ccc(N2C3CCC2CN(C(=O)CCS(=O)(=O)c2ccccc2C(F)(F)F)C3)nc1] | 6-(3-(3-((2-(trifluoromethyl)phenyl)sulfonyl)propanoyl)-3,8-diazabicyclo[3.2.1]octan-8-yl)nicotinonitrile | 479.1 |
| 30 | 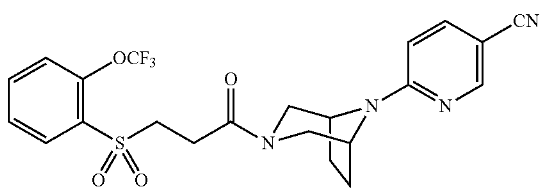 [SMILES: N#Cc1ccc(N2C3CCC2CN(C(=O)CCS(=O)(=O)c2ccccc2OC(F)(F)F)C3)nc1] | 6-(3-(3-((2-(trifluoromethoxy)phenyl)sulfonyl)propanoyl)-3,8-diazabicyclo-[3.2.1]octan-8-yl)nicotinonitrile | 495.2 |
| 31 | 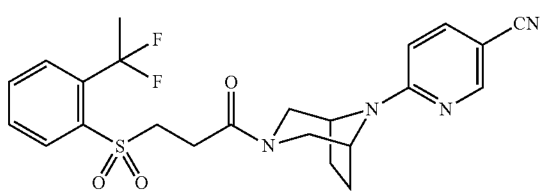 [SMILES: CC(F)(F)c1ccccc1S(=O)(=O)CCC(=O)N1CC2CCC(C1)N2c1ccc(C#N)cn1] | 6-(3-(3-((2-(1,1-difluoroethyl)phenyl)sulfonyl)propanoyl)-3,8-diazabicyclo[3.2.1]octan-8-yl)nicotinonitrile | 475.1 |
| 32 | 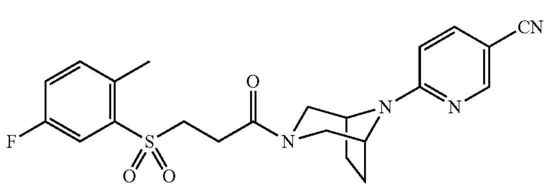 [SMILES: Cc1ccc(F)cc1S(=O)(=O)CCC(=O)N1CC2CCC(C1)N2c1ccc(C#N)cn1] | 6-(3-(3-((5-fluoro-2-methylphenyl)sulfonyl)propanoyl)-3,8-diazabicyclo[3.2.1]octan-8-yl)nicotinonitrile | 443.1 |
| 33 | 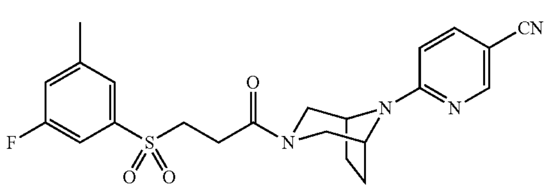 [SMILES: Cc1cc(F)cc(S(=O)(=O)CCC(=O)N2CC3CCC(C2)N3c2ccc(C#N)cn2)c1] | 6-(3-(3-((3-fluoro-5-methylphenyl)sulfonyl)propanoyl)-3,8-diazabicyclo[3.2.1]octan-8-yl)nicotinonitrile | 443.1 |

| Example | Structure | Name | [M + H]+ |
|---|---|---|---|
| 34 | 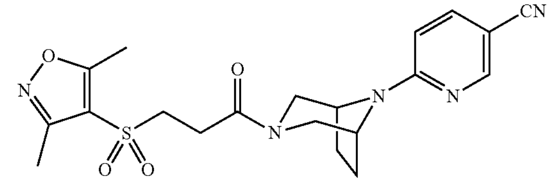 [SMILES: Cc1noc(C)c1S(=O)(=O)CCC(=O)N1CC2CCC(C1)N2c1ccc(C#N)cn1] | 6-(3-{3-[(3,5-dimethyl-1,2-oxazol-4-yl)sulfonyl]propanoyl}-3,8-diazabicyclo[3.2.1]octan-8-yl)pyridine-3-carbonitrile | 430.2 |

Example 35 and 36: Synthesis of 6-(3-(3-((2-((R)-2,2-difluorocyclopropyl)phenyl)-sulfonyl)propanoyl)-3,8-diazabicyclo[3.2.1]octan-8-yl)nicotinonitrile and 643434(2-((S)-2,2-difluorocyclopropyl)phenyl)sulfonyl)propanoyl)-3,8-diazabicyclo[3.2.1]octan-8-yl)nicotinonitrile

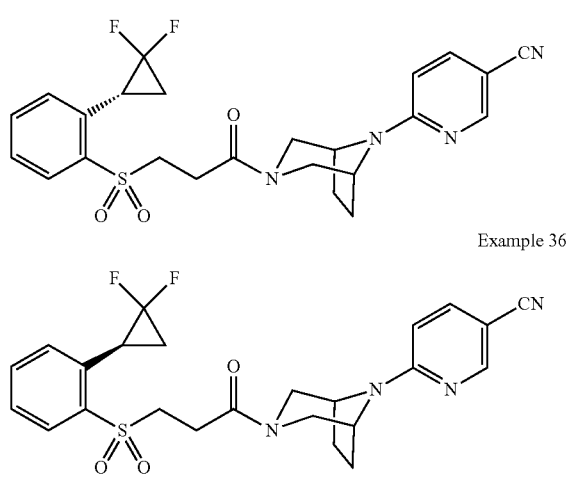

Example 35

Example 36

The racemate from Example 5 was separated by chiral HPLC using CHIRALPAK IE (2*25 cm, 5 um) as the chiral stationary phase, a 2:1:1 (v/v/v) solution of ethanol: hexanes: dichloromethane as the mobile phase, and 10 mM ammonia in methanol as the additive. The absolute stereochemistry of Example 35 (faster eluting peak) and Example 36 (slower eluting peak), both compounds isolated as a white solid, was arbitrarily assigned.

Example 37: In Vitro Functional Assay of Muscarinic Acetylcholine Receptor Activity CHO-K1 cells stably expressing human $M_1$ receptor with aequorin (Perkin Elmer) were grown in F12 media (Gibco) containing 10% FBS (ATCC), 0.4 mg/mL geneticin (Sigma-Aldrich) and 0.25 mg/mL Zeocin (Invitrogen). Cells were grown as per the manufacturer's protocol. For compound testing, cells were grown to confluency and detached gently with Accutase (Sigma-Aldrich) followed by centrifugation for 5 min at 150×g. Cells were then re-suspended in assay buffer (i.e. DMEM/F-12 HEPES without phenol red (Invitrogen) with 0.1% BSA (Sigma-Aldrich)) at a density of $5 \times 10^6$ cells/ml. Under sterile conditions, 5 coelenterazine (Invitrogen) was added to the cells, mixed, then incubated at room temperature protected from light, with gentle agitation, for 4 h.

Primary compound plates were prepared in 100% DMSO in opaque 96-well plates (VWR) and serially diluted in half log increments. Secondary compound plates were prepared at 3×concentration in assay buffer. Compounds were added to white, clear bottom tissue culture treated 96-well plates (Fisher Scientific). Coelenterazine-loaded cells were then added at $5 \times 10^5$ cells/well.

Compounds and cells were incubated at room temperature for 30 min in the dark. Acetylcholine at the $EC_{80}$ concentration was added and calcium flux measured using a FlexStation 3 (Molecular Devices). Sigmoidal dose-response curves were generated by measuring luminescence over 40 sec and calculating the area under the curve. Dose response curves and $IC_{50}$ values were generated using Prism (GraphPad). Compounds were tested at a final concentration range of 100 pM to 10 µM in 0.1% DMSO. Results are shown in Table 1.

TABLE 1

| Example | $M_1$ $IC_{50}$ |
|---|---|
| 1 | A |
| 2 | B |
| 3 | A |
| 4 | A |
| 5 | B |
| 6 | D |
| 7 | B |
| 8 | B |
| 9 | C |
| 10 | D |
| 11 | B |
| 12 | B |
| 13 | B |
| 14 | B |
| 15 | B |
| 16 | C |
| 17 | C |
| 18 | D |
| 19 | C |
| 20 | B |
| 21 | C |
| 22 | C |
| 23 | C |
| 24 | A |
| 25 | C |
| 26 | C |
| 27 | B |
| 28 | C |
| 29 | C |

TABLE 1-continued

| Example | $M_1$ $IC_{50}$ |
|---|---|
| 30 | C |
| 31 | C |
| 32 | C |
| 33 | C |
| 34 | |
| 35 | A |
| 36 | C |

A = $IC_{50}$ of less than 10 nM;
B = $IC_{50}$ less than 100 nM but greater than or equal to 10 nM;
C = $IC_{50}$ less than 1 μM (1,000 nM) but greater than or equal to 100 nM;
D = $IC_{50}$ less than 10 μM (10,000 nM) but greater than or equal to 1 μM (1,000 nM);
E = $IC_{50}$ greater than 1 μM (1,000 nM)

CHO-K1 cells stably expressing human $M_2$, $M_3$ and $M_4$ receptors, respectively, with aequorin (Perkin Elmer) were used to assess a test compound's ability to dose-dependently reverse the $EC_{80}$ acetylcholine response. The $IC_{50}$ of the compounds was calculated from the dose response curve. Results for select compounds are shown in Table 2.

TABLE 2

| Example | $M_2$ $IC_{50}$ | $M_3$ $IC_{50}$ | $M_4$ $IC_{50}$ |
|---|---|---|---|
| 2 | E | C | C |
| 3 | E | C | C |
| 24 | D | C | C |
| 35 | B | C | B |

A = $IC_{50}$ of less than 10 nM;
B = $IC_{50}$ less than 100 nM but greater than or equal to 10 nM;
C = $IC_{50}$ less than 1 μM (1,000 nM) but greater than or equal to 100 nM;
D = $IC_{50}$ less than 10 μM (10,000 nM) but greater than or equal to 1 μM (1,000 nM);
E = $IC_{50}$ greater than 10 μM (10,000 nM)

What is claimed is:

1. A method of treating multiple sclerosis in a subject in need thereof, comprising administering to the subject a therapeutically effective amount of a compound selected from the group consisting of:

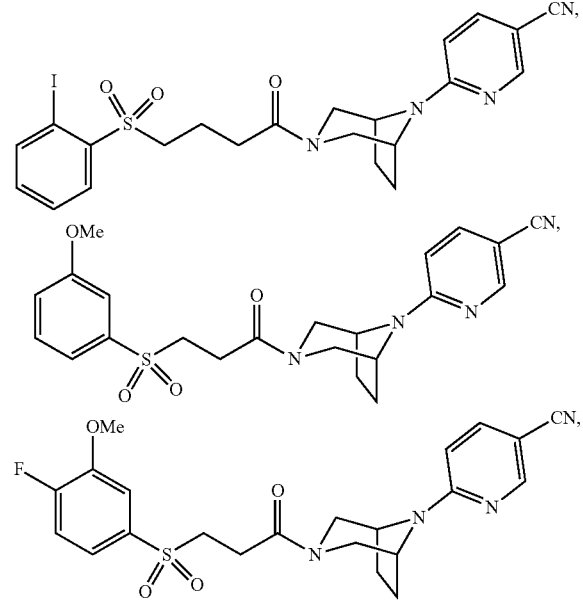

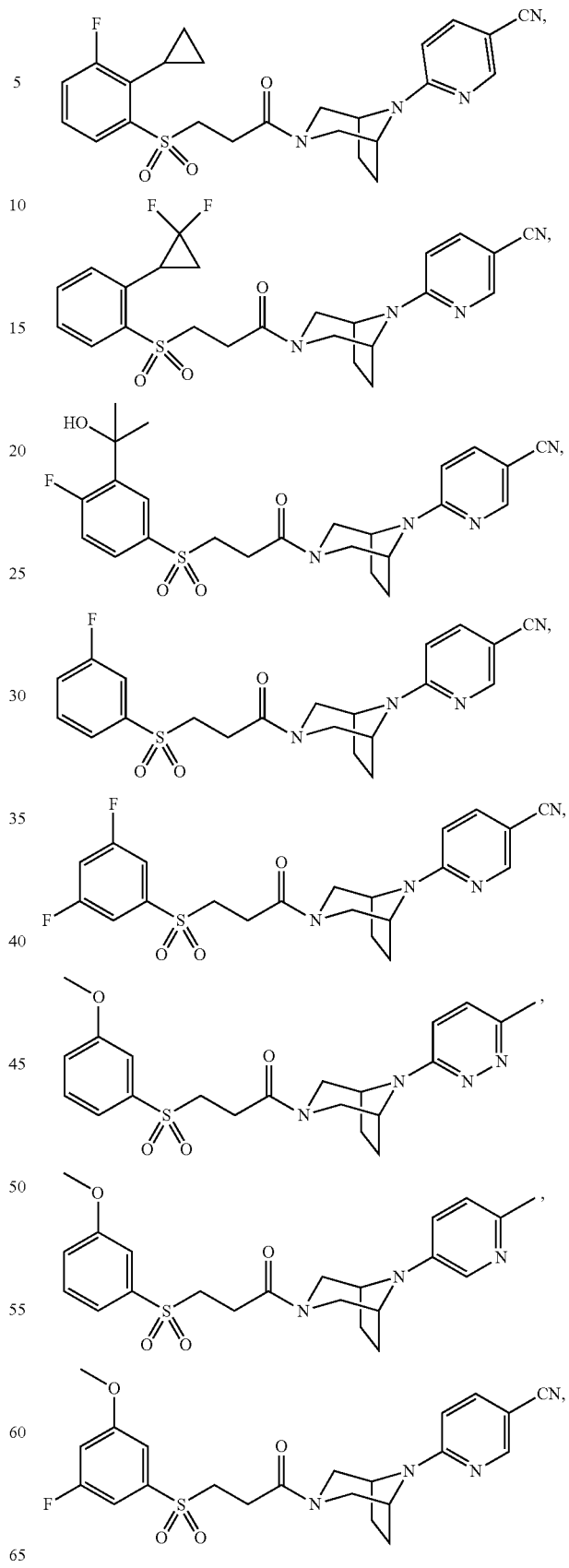

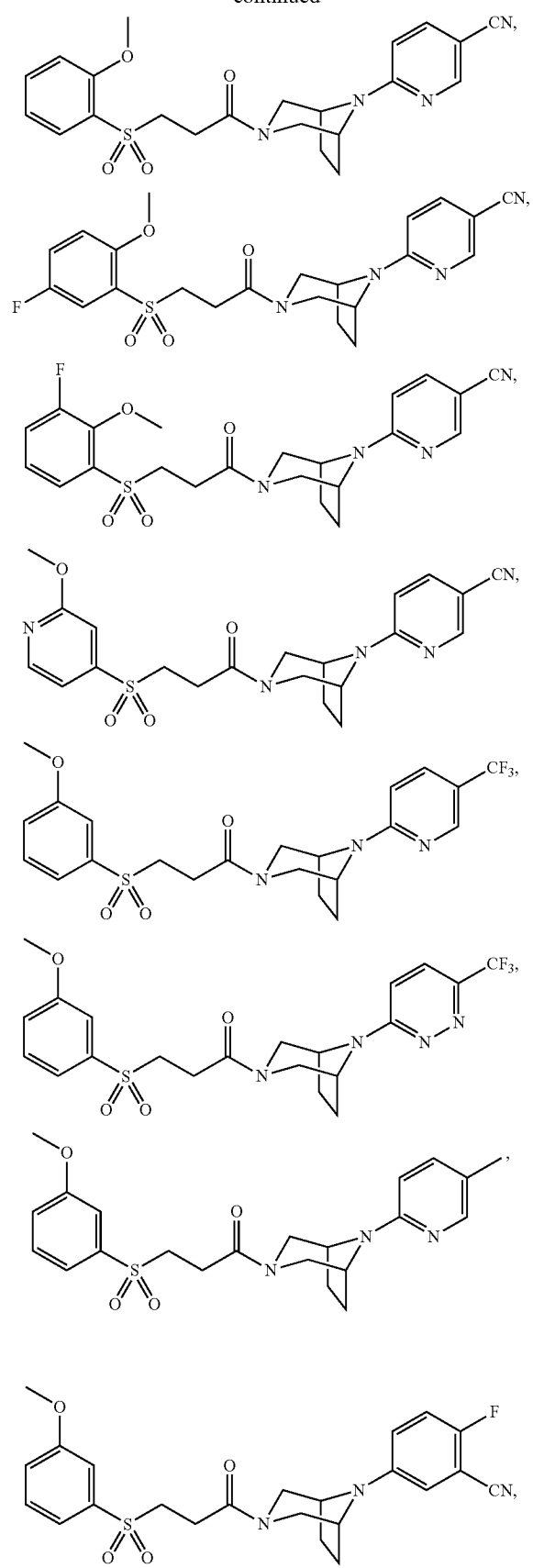
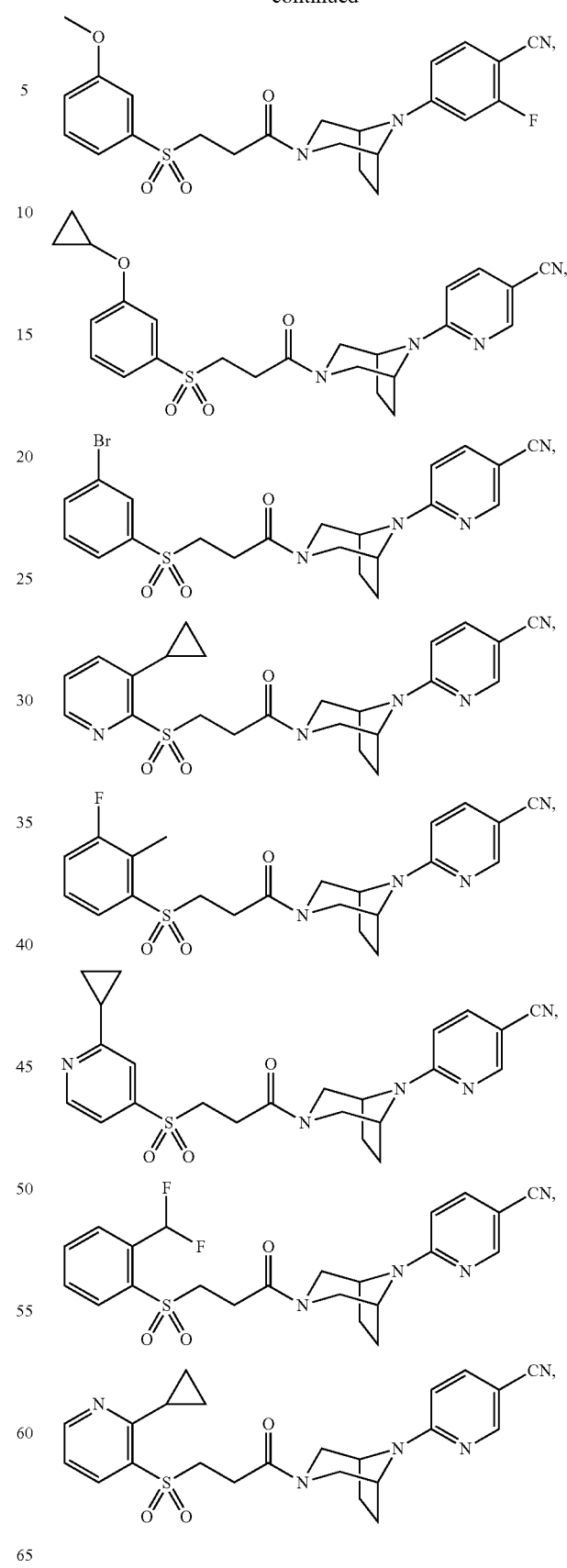

87

-continued

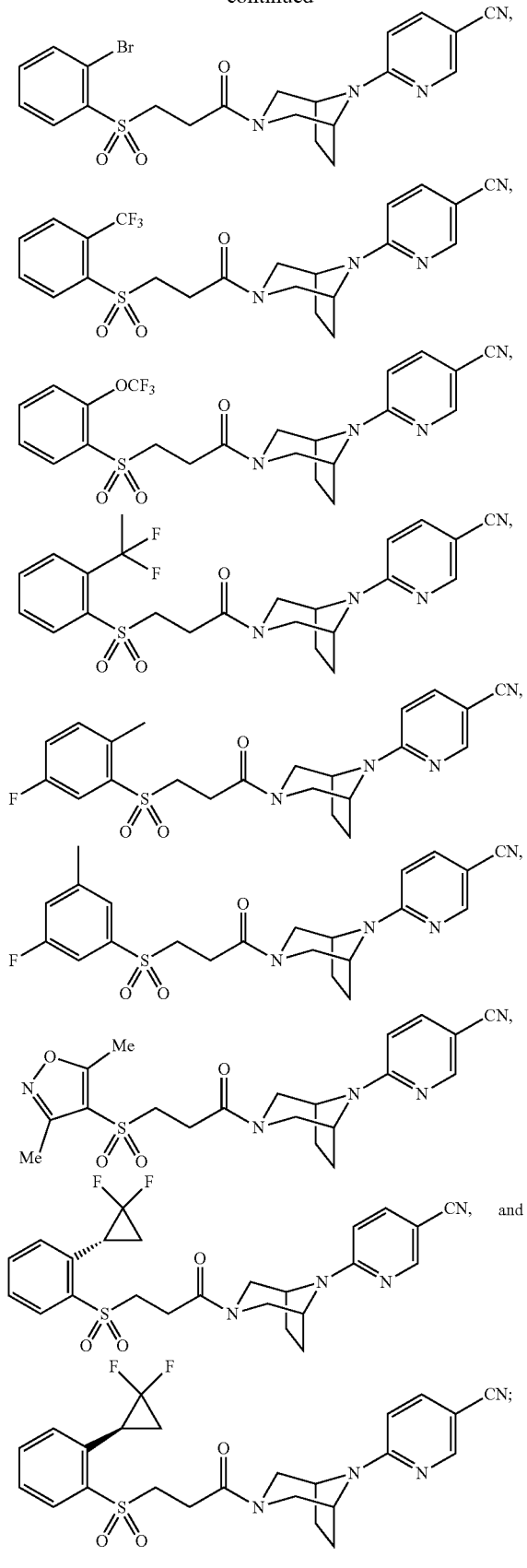

or a pharmaceutically acceptable salt thereof.

2. The method of claim 1, further comprising the administration of one or more immunomodulatory agents.

3. The method of claim 2, wherein the one or more immunomodulatory agents are selected from the group consisting of: an IFN-β 1 molecule; a corticosteroid; a polymer of glutamic acid, lysine, alanine and tyrosine or glatiramer; an antibody or fragment thereof against alpha-4 integrin or natalizumab; an anthracenedione molecule or mitoxantrone; a fingolimod or FTY720 or other S1P1 functional modulator; a dimethyl fumarate or other NRF2 functional modulator; an antibody to the alpha subunit of the IL-2 receptor of T cells (CD25) or daclizumab; an antibody against CD52 or alemtuzumab; an antibody against CD20 or ocrelizumab; and an inhibitor of a dihydroorotate dehydrogenase or teriflunomide.

4. A method of modulating muscarinic acetylcholine receptor M1 activity in a subject, the method comprising administering to the subject a compound a therapeutically effective amount of a compound selected from the group consisting of:

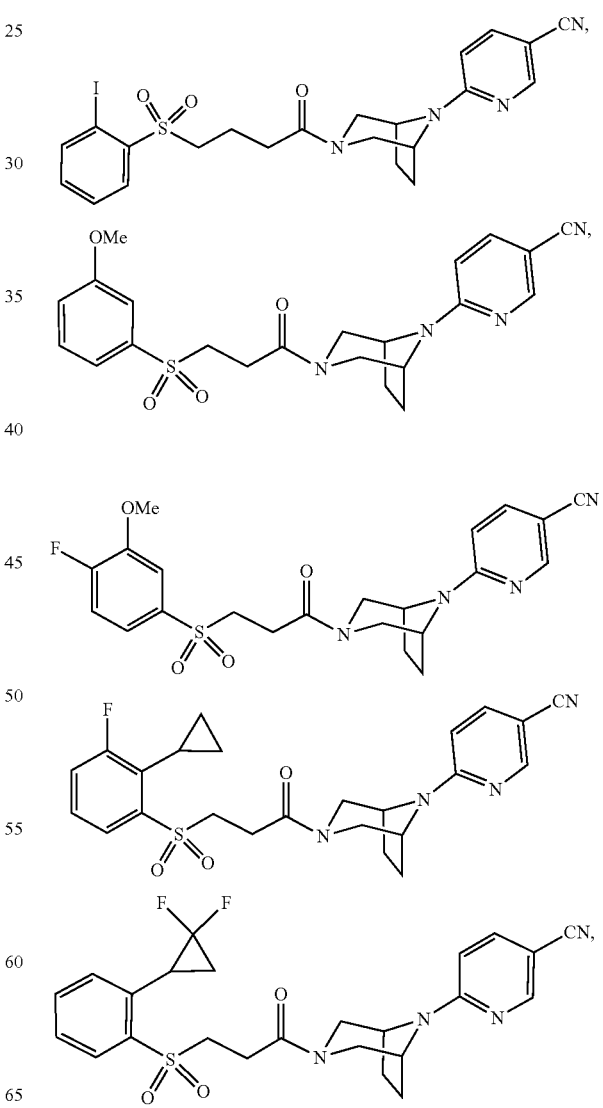

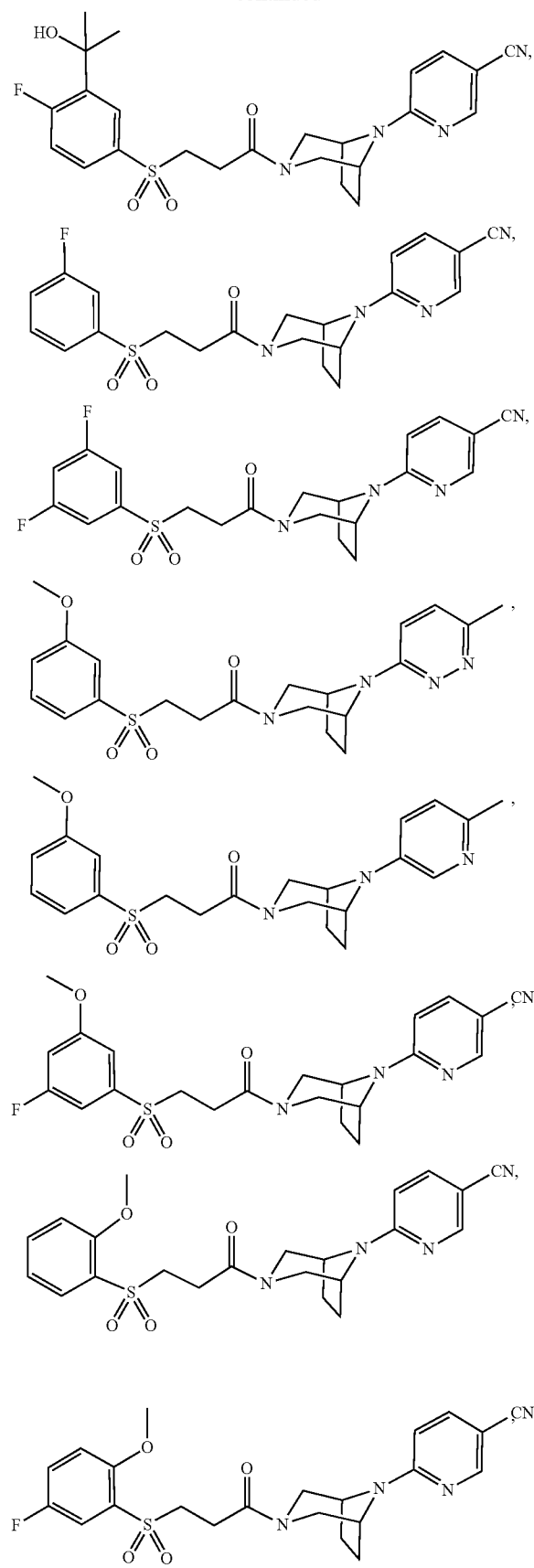
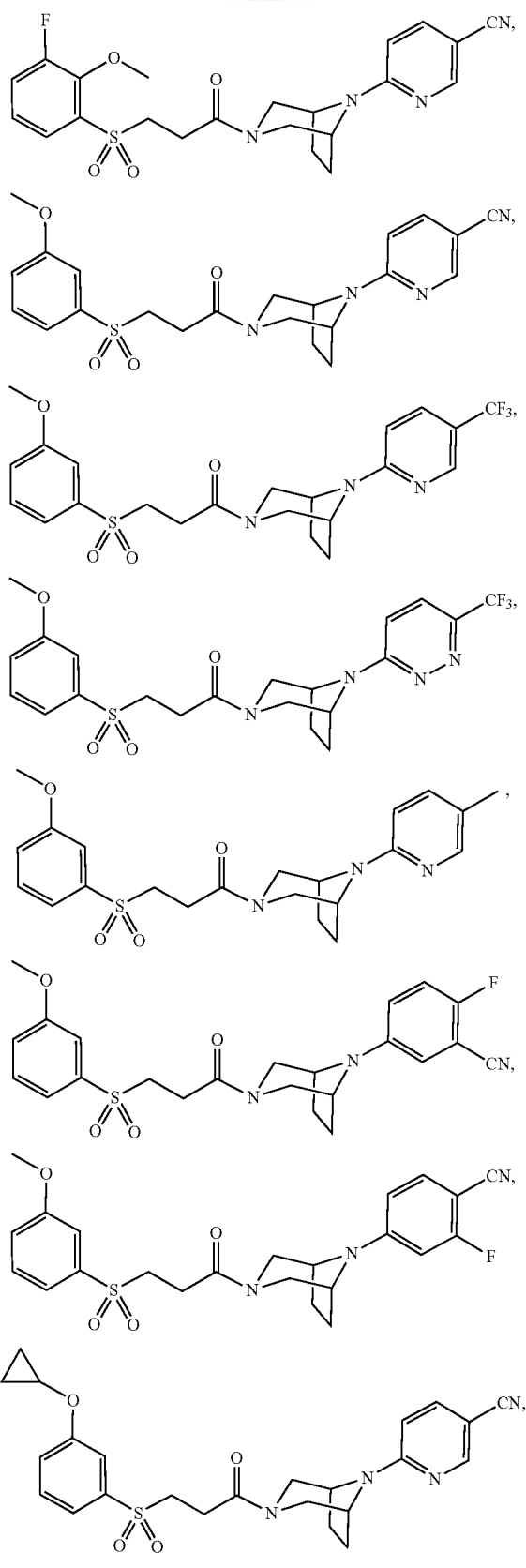

91
-continued
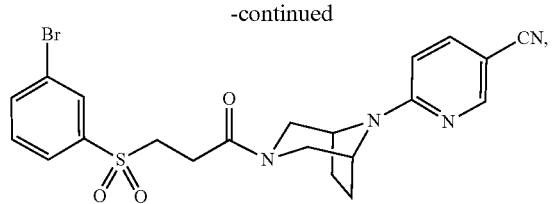
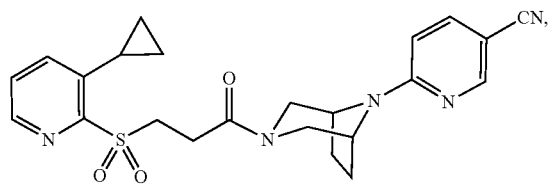
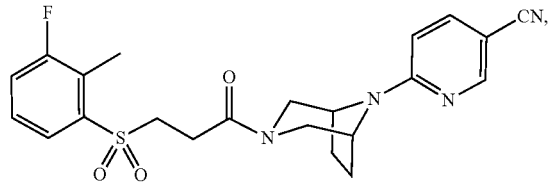
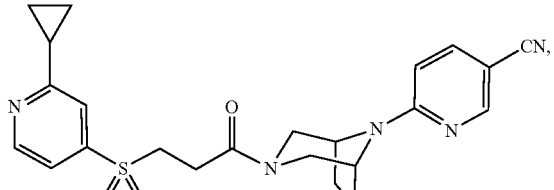
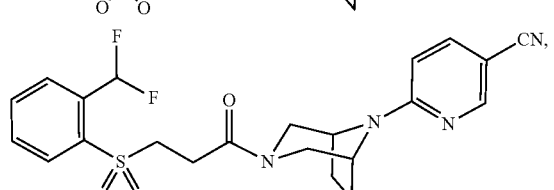
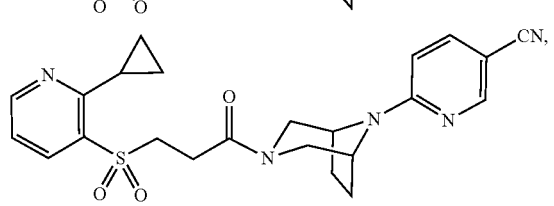
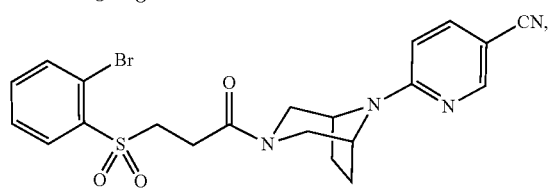
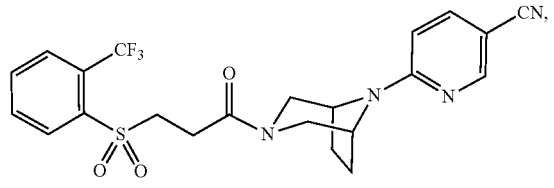
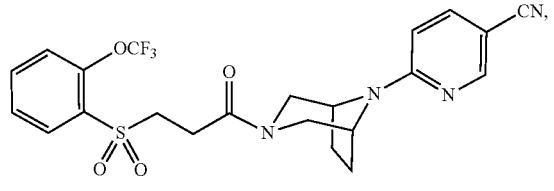
92
-continued
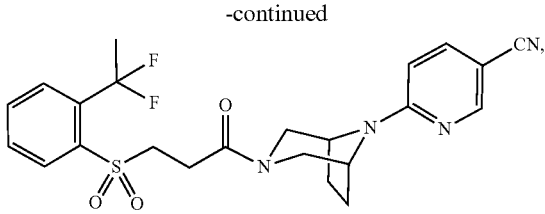
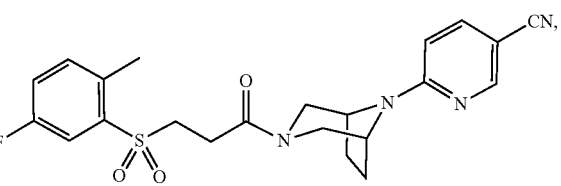
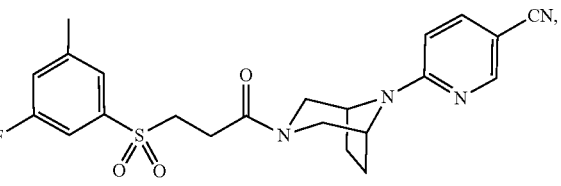
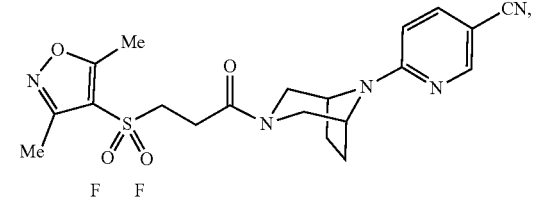
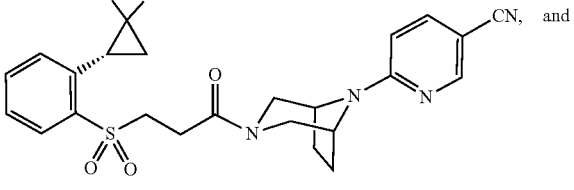
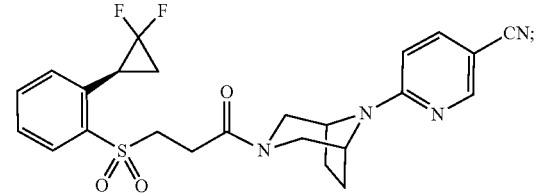
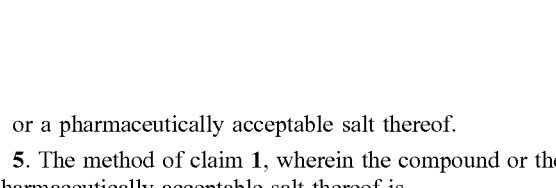
or a pharmaceutically acceptable salt thereof.
5. The method of claim 1, wherein the compound or the pharmaceutically acceptable salt thereof is
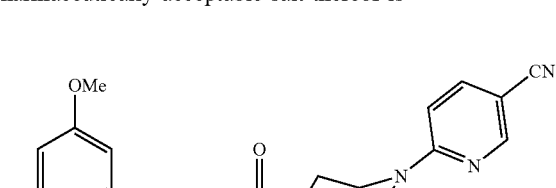
or a pharmaceutically acceptable salt thereof.
6. The method of claim 4, wherein the compound or the pharmaceutically acceptable salt thereof is

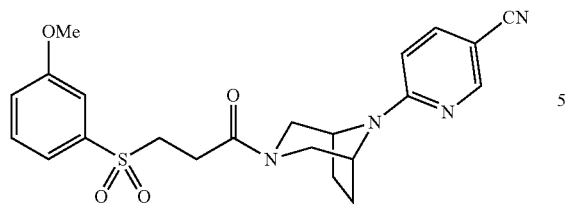
or a pharmaceutically acceptable salt thereof.
* * * * *